United States Patent
Price et al.

(10) Patent No.: US 10,806,630 B2
(45) Date of Patent: *Oct. 20, 2020

(54) INJECTION DEVICE FOR SUBRETINAL DELIVERY OF THERAPEUTIC AGENT

(71) Applicant: ORBIT BIOMEDICAL LIMITED, Stevenage (GB)

(72) Inventors: Daniel W. Price, Loveland, OH (US); Brendan J. Oberkircher, Cincinnati, OH (US); James G. Lee, Raynham, MA (US); Clinton Denlinger, Cincinnati, OH (US); Daniel J. Prenger, Loveland, OH (US); Geoffrey King, Cincinnati, OH (US); Scott Uhland, San Jose, CA (US); Mark C. Tsai, Chalfont, PA (US); Michael F. Keane, Downington, PA (US); Isaac J. Khan, Bridgewater, NJ (US); Benjamin L. Ko, Cincinnati, OH (US); Thomas E. Meyer, Philadelphia, PA (US); Denis P. Turner, San Clemente, CA (US)

(73) Assignee: GYROSCOPE THERAPEUTICS LIMITED, Stevenage (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/861,472

(22) Filed: Apr. 29, 2020

(65) Prior Publication Data

US 2020/0297531 A1    Sep. 24, 2020

Related U.S. Application Data

(63) Continuation of application No. 15/609,457, filed on May 31, 2017.

(Continued)

(51) Int. Cl.
  *A61F 9/00* (2006.01)
  *A61M 25/02* (2006.01)
  (Continued)

(52) U.S. Cl.
  CPC ............ *A61F 9/0026* (2013.01); *A61B 46/23* (2016.02); *A61B 50/30* (2016.02); *A61F 9/0008* (2013.01);
  (Continued)

(58) Field of Classification Search
  CPC ........ A61F 9/00; A61F 9/0008; A61F 9/0017; A61F 9/0026; A61F 2009/0035;
  (Continued)

(56) References Cited

U.S. PATENT DOCUMENTS 2,373,389 A    4/1945  Sidney
2,907,328 A    10/1959 Cohen
(Continued)

FOREIGN PATENT DOCUMENTS

CN    204766762 U    11/2015
DE    20 51 239 A1   5/1971
(Continued)

OTHER PUBLICATIONS

International Search Report and Written Opinion dated Sep. 18, 2017 for International Application No. PCT/US2017/037368, 14 pages.
(Continued)

*Primary Examiner* — Bhisma Mehta
*Assistant Examiner* — Hong-Van N Trinh
(74) *Attorney, Agent, or Firm* — Frost Brown Todd LLC

(57) ABSTRACT

An apparatus includes a pad assembly, an injector assembly, an injector driver, and a fluid source. The pad assembly is sized and configured to be placed on a forehead of a patient. The injector assembly includes a body, a flexible cannula,
(Continued)

and a needle. The body is configured to be removably secured to the pad assembly. The cannula is sized to be inserted through an incision in an eye of a patient. The needle is slidably disposed in the cannula. The injector driver is operable to drive the needle longitudinally relative to the flexible cannula. The fluid source assembly is in fluid communication with the needle.

15 Claims, 54 Drawing Sheets

Related U.S. Application Data

(60) Provisional application No. 62/351,628, filed on Jun. 17, 2016.

(51) Int. Cl.
    *A61B 50/30* (2016.01)
    *A61B 46/23* (2016.01)

(52) U.S. Cl.
    CPC .......... *A61F 9/0017* (2013.01); *A61M 25/02* (2013.01); *A61B 2046/234* (2016.02); *A61B 2050/314* (2016.02); *A61M 2025/0213* (2013.01); *A61M 2025/0266* (2013.01)

(58) Field of Classification Search
    CPC .......... A61F 2009/0043; A61F 9/0052; A61B 50/20; A61B 2050/21; A61M 25/02; A61M 2025/0206; A61M 2025/0213; A61M 2025/022; A61M 2025/0226; A61M 2025/024; A61M 2025/0246; A61M 2025/0253; A61M 2025/026; A61M 2025/0266; A61M 2025/0273; A61M 2025/028; A61M 2209/08; A61M 2209/082; A61M 2209/084; A61M 2209/088; A61M 5/1414; A61M 5/1415; A61M 2005/1416; A61M 5/1417; A61M 5/1418
    See application file for complete search history.

(56) References Cited

U.S. PATENT DOCUMENTS

| 3,288,137 | A | 11/1966 | Lund |
|---|---|---|---|
| 3,664,340 | A | 5/1972 | Morgan |
| 3,738,359 | A | 6/1973 | Lindquist et al. |
| 5,195,538 | A | 3/1993 | Eldridge, Jr. et al. |
| 6,368,315 | B1 | 4/2002 | Gillis et al. |
| 6,824,532 | B2 | 11/2004 | Gillis et al. |
| 7,189,245 | B2 | 3/2007 | Kaplan |
| 7,207,980 | B2 | 4/2007 | Christian et al. |
| 7,413,734 | B2 | 8/2008 | Mistry et al. |
| 8,197,435 | B2 | 6/2012 | Prausnitz et al. |
| 8,425,473 | B2 | 4/2013 | Ho et al. |
| 2005/0143363 | A1 | 6/2005 | de Juan et al. |
| 2006/0257835 | A1 | 11/2006 | Wallaker et al. |
| 2006/0259124 | A1 | 11/2006 | Matsuoka et al. |
| 2008/0058704 | A1 | 3/2008 | Hee et al. |
| 2008/0140006 | A1 | 6/2008 | Eskuri et al. |
| 2010/0036472 | A1 | 2/2010 | Papp |
| 2012/0191064 | A1 | 7/2012 | Conston et al. |
| 2012/0271272 | A1 | 10/2012 | Hammack et al. |
| 2013/0216623 | A1 | 8/2013 | Yamamoto et al. |
| 2013/0245600 | A1 | 9/2013 | Yamamoto et al. |
| 2015/0090255 | A1 | 4/2015 | Gulliver et al. |
| 2015/0209180 | A1 | 7/2015 | Prausnitz et al. |
| 2015/0223977 | A1 | 8/2015 | Oberkircher et al. |
| 2015/0258120 | A1 | 9/2015 | Zarnitsyn et al. |
| 2015/0351958 | A1 | 12/2015 | Contiliano et al. |
| 2015/0351959 | A1 | 12/2015 | Clem et al. |
| 2016/0074211 | A1 | 3/2016 | Ko et al. |
| 2016/0074212 | A1 | 3/2016 | Price et al. |
| 2016/0074217 | A1 | 3/2016 | Price et al. |
| 2016/0081849 | A1 | 3/2016 | Tsai et al. |
| 2016/0106579 | A1 | 4/2016 | Ryan |
| 2017/0095369 | A1 | 4/2017 | Andino et al. |
| 2017/0252209 | A1 | 9/2017 | Gooi et al. |
| 2017/0258988 | A1 | 9/2017 | Meyer et al. |
| 2017/0333416 | A1 | 11/2017 | Zarnitsyn et al. |
| 2017/0360605 | A1 | 12/2017 | Oberkircher et al. |
| 2017/0360607 | A1 | 12/2017 | Price et al. |
| 2018/0042765 | A1 | 2/2018 | Noronha et al. |

FOREIGN PATENT DOCUMENTS

| WO | WO 2013/157960 A1 | 10/2013 |
|---|---|---|
| WO | WO 2017/042584 A1 | 3/2017 |

OTHER PUBLICATIONS

U.S. Appl. No. 62/351,428, filed Jun. 17, 2016.
Chinese Office Action and Search Report dated Apr. 26, 2020 for Application No. 201780037448.2, 11 pages.

INJECTION DEVICE FOR SUBRETINAL DELIVERY OF THERAPEUTIC AGENT

PRIORITY

This application is a continuation of U.S. Non-Provisional Patent Application Ser. No. 15/609,457, entitled "Injection Device for Subretinal Delivery of Therapeutic Agent," filed May 31, 2017, which claims priority to U.S. Provisional Patent Application No. 62/351,628, entitled "Subretinal Injection Device," filed Jun. 17, 2016, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
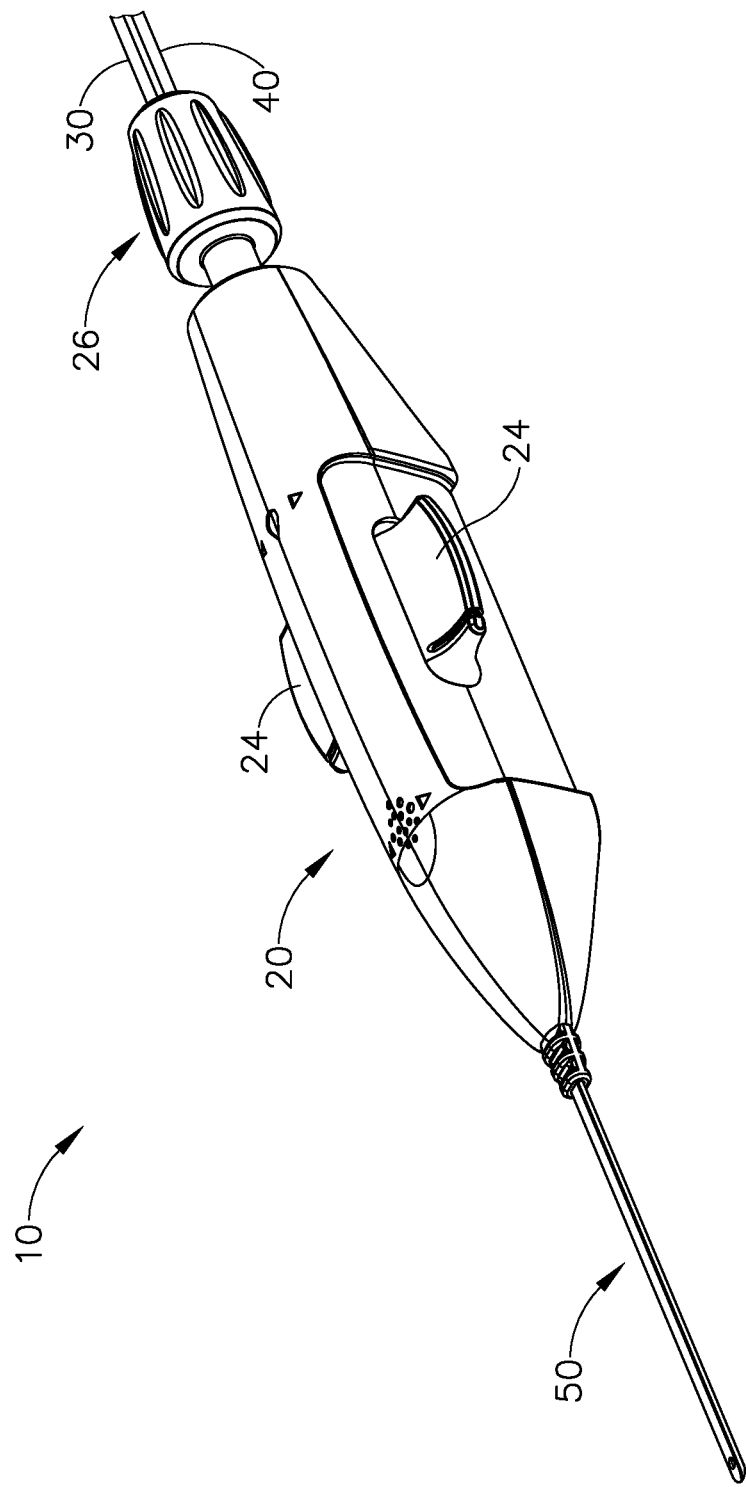
FIG. 1 depicts a perspective view of an exemplary instrument for subretinal administration of a therapeutic agent from a suprachoroidal approach.
Figure 2:
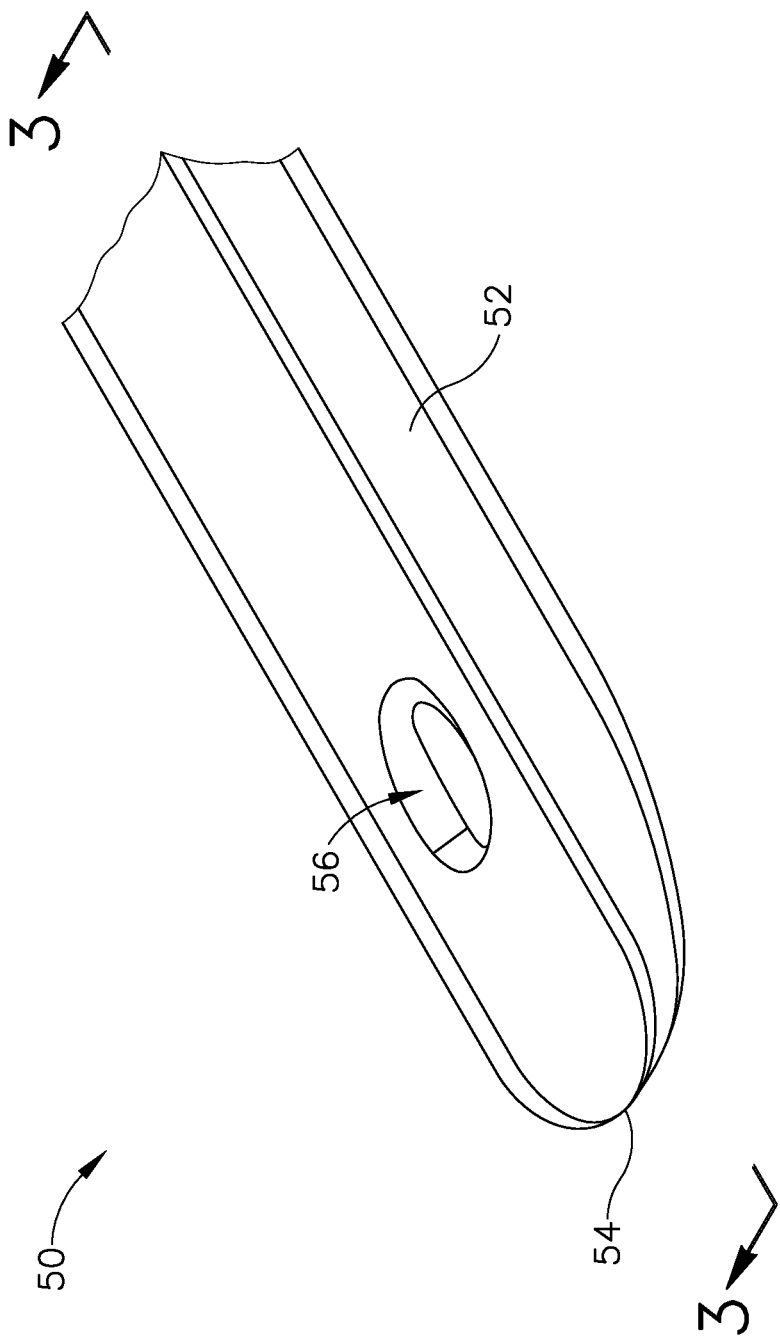
FIG. 2 depicts a perspective view of the distal end of an exemplary cannula that may be incorporated into the instrument of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument for Subretinal Administration of Therapeutic Agent

FIG. 1 shows an exemplary instrument (10) that is configured for use in a procedure for the subretinal administration of a therapeutic agent to an eye of a patient from a suprachoroidal approach. Instrument (10) comprises a body (20) and a flexible cannula (50) extending distally from body (20). Cannula (50) of the present example has a generally rectangular cross section, though any other suitable cross-sectional profile (e.g., elliptical, etc.) may be used. Cannula (50) is generally configured to support a needle (100) that is slidable within cannula (50), as will be described in greater detail below.

In the present example, cannula (50) comprises a flexible material such as Polyether block amide (PEBA), which may be manufactured under the trade name PEBAX. Of course, any other suitable material or combination of materials may be used. Also in the present example, cannula (50) has a cross-sectional profile dimension of approximately 2.0 mm by 0.8 mm, with a length of approximately 80 mm. Alternatively, any other suitable dimensions may be used. As will be described in greater detail below, cannula (50) is flexible enough to conform to specific structures and contours of the patient's eye, yet cannula (50) has sufficient column strength to permit advancement of cannula (50) between the sclera and choroid of patient's eye without buckling. By way of example only, cannula (50) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein.

Figure 3A:
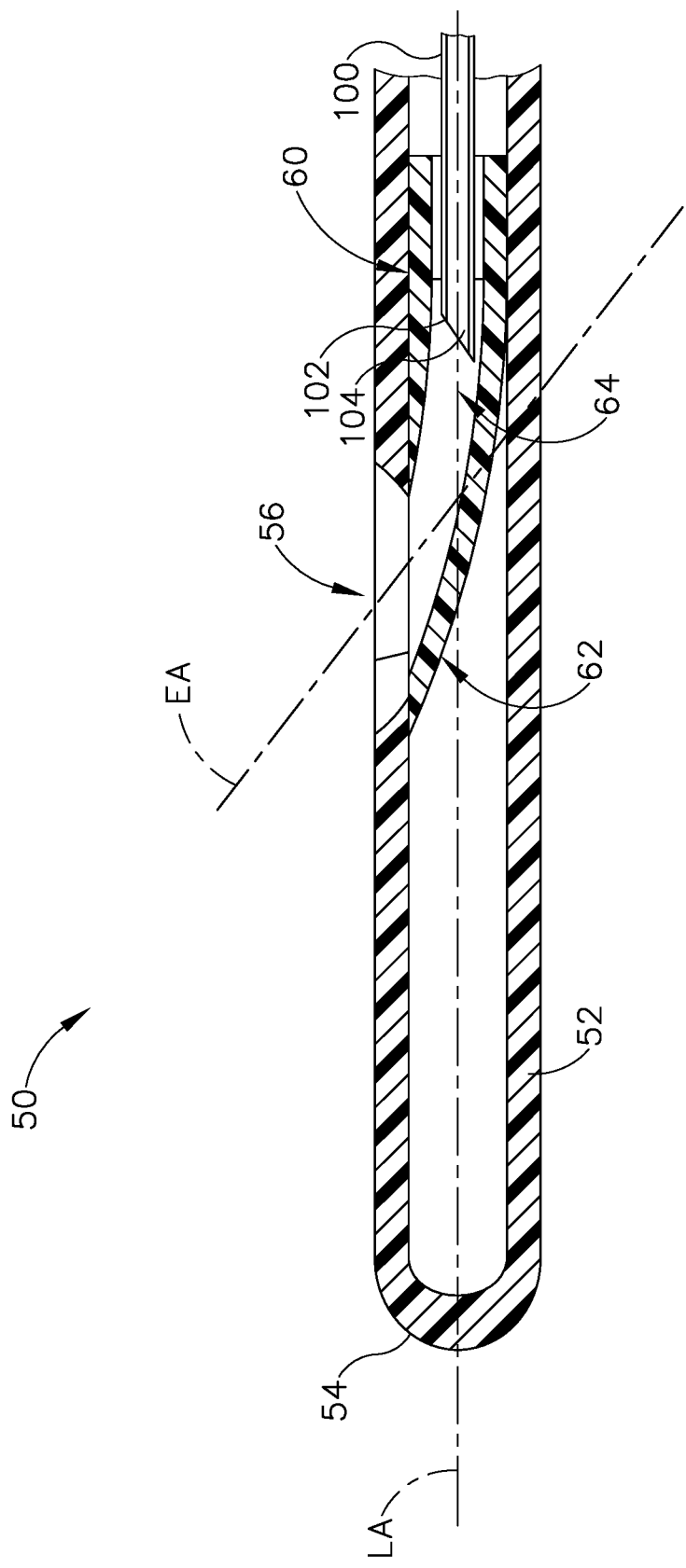
FIG. 3A depicts a cross-sectional side view of the cannula of FIG. 2, with the cross-section taken along line 3-3 of FIG. 2, with a needle in a first longitudinal position.
Figure 3B:
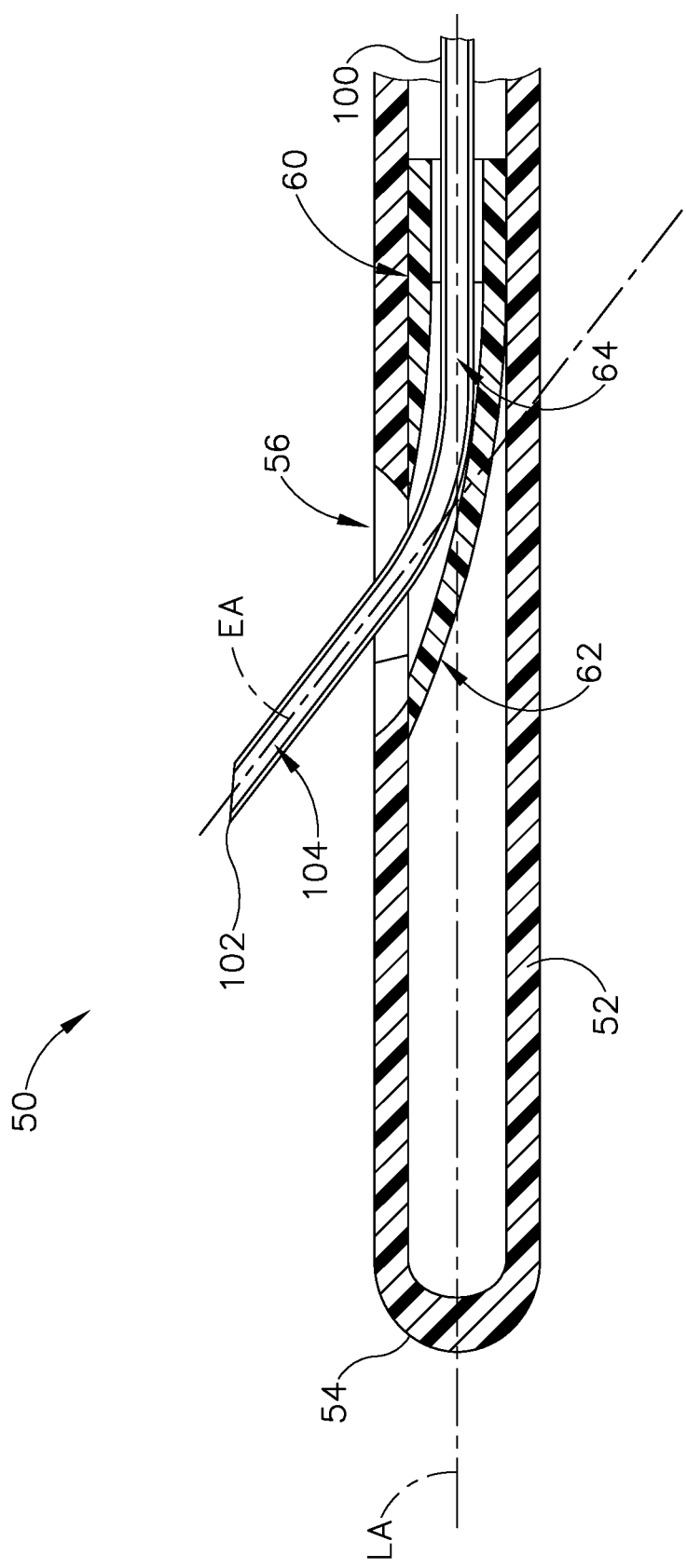
FIG. 3B depicts a cross-sectional side view of the cannula of FIG. 2, with the cross-section taken along line 3-3 of FIG. 2, with the needle in a second longitudinal position.

As can be seen in FIGS. 2-3B and 6, cannula (50) comprises a body (52), a closed distal end (54), and a lateral opening (56) that is located proximal to distal end (54). In the present example, distal end (54) has a rounded configuration. It should be understood that distal end (54) may have any suitable kind of curvature. It should also be understood that distal end (54) may have any other suitable kind of configuration (e.g., beveled, etc.). In the present example, distal end (54) is configured to provide separation between the sclera and choroid layers to enable cannula (50) to be advanced between such layers while not inflicting trauma to the sclera or choroid layers. Also in the present example, the region of body (52) that defines lateral opening (56) is beveled, as best seen in FIGS. 3A-3B. Alternatively, the edge of lateral opening (56) may have any other suitable configuration.

As best seen in FIGS. 3A-3B, a needle guide (60) is disposed within the hollow interior of cannula (50). By way of example only, needle guide (60) may be secured within cannula (50) by a press or interference fit, by adhesives, by mechanical locking mechanisms, and/or in any other suitable fashion. Needle guide (60) includes a curved distal end (62) that leads to lateral opening (56) of cannula (50), such that a lumen (64) of needle guide (60) distally terminates at lateral opening (56). The portion of needle guide (60) that is proximal to distal end (62) is substantially straight. Needle guide (60) may be formed of plastic, stainless steel, and/or any other suitable biocompatible material(s).

Needle (100) of the present example has a sharp distal tip (102) and defines a lumen (104). Distal tip (102) of the present example has a lancet configuration. In some other versions, distal tip (102) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (102) may take will be apparent to those of ordinary skill in the art in view of the teachings herein. Needle (100) of the present example comprises a stainless steel hypodermic needle that is sized to deliver the therapeutic agent while being small enough to minimize incidental trauma as needle (100) penetrates tissue structures of the patient's eye, as will be described in greater detail below. While stainless steel is used in the present example, it should be understood that any other suitable material(s) may be used, including but not limited to nitinol, etc.

By way of example only, needle (100) may be 35 gauge with a 100 μm inner diameter, although other suitable sizes may be used. For instance, the outer diameter of needle (100) may fall within the range of 27 gauge to 45 gauge; or more particularly within the range of 30 gauge to 42 gauge; or more particularly within the range of 32 gauge to 39 gauge. As another merely illustrative example, the inner diameter of needle (100) may fall within the range of approximately 50 µm to approximately 200 µm; or more particularly within the range of approximately 50 µm to approximately 150 µm; or more particularly within the range of approximately 75 µm to approximately 125 µm.

Needle (100) is slidably disposed within lumen (64) of needle guide (60). Needle guide (60) is generally configured to direct needle (100) upwardly along an exit axis (EA) that is obliquely oriented relative to the longitudinal axis (LA) of cannula (50) through lateral opening (56) of cannula (50). This is shown in the sequence depicted in FIGS. 3A-3B, in which FIG. 3A shows needle (100) in a proximal position (where distal tip (102) of needle (100) is fully contained in lumen (64) of needle guide (60)); and FIG. 3B shows needle (100) in a distal position (where distal tip (102) of needle (100) is outside of needle guide (60)). While needle (100) is flexible, needle (100) of the present example is resiliently biased to assume a straight configuration. Thus, as shown in FIG. 3B, the portion of needle (100) that extends outside of cannula (50) and needle guide (60) is substantially straight, extending along exit axis (EA). In particular, at least a substantial length of the portion of needle (100) that extends outside of cannula (50) and needle guide (60) is coaxially aligned with exit axis (EA).

It should be understood that the depiction of exit axis (EA) in FIGS. 3A-3B may be somewhat exaggerated, for illustrative purposes only. In some versions, curved distal end (62) is configured to direct needle (100) along an exit axis (EA) that extends distally from cannula (50) at an angle of approximately 7° to approximately 9° relative to the longitudinal axis (LA) of cannula (50). It should be understood that such an angle may be desirable to deflect needle (100) in a direction to ensure penetration of needle into the choroid and to minimize the possibility of needle (100) continuing beneath the choroid through the suprachoroidal space (as opposed to penetrating through the choroid) and the possibility of retinal perforation. By way of further example only, curved distal portion (88) may urge needle (100) to exit cannula (50) along an exit axis (EA) that is oriented at an angle within the range of approximately 5° to approximately 30° relative to the longitudinal axis (LA) of cannula (50); or more particularly within the range of approximately 5° to approximately 20° relative to the longitudinal axis (LA) of cannula (50); or more particularly within the range of approximately 5° to approximately 10° relative to the longitudinal axis (LA) of cannula (50).

As shown in FIG. 1, instrument (10) of the present example further comprises an actuation knob (26) located at the proximal end of body (20). Actuation knob (26) is rotatable relative to body (20) to thereby selectively translate needle (100) longitudinally relative to cannula (50). In particular, actuation knob (26) is rotatable in a first angular direction to drive needle (100) distally relative to cannula (50); and in a second angular direction to drive needle (100) proximally relative to cannula (50). By way of example only, instrument (10) may provide such functionality through knob (26) in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Alternatively, any other suitable kind of actuation feature(s) may be used to drive needle (100) longitudinally relative to cannula (50).

In the present example, knob (26) is rotatable through a complete range of motion that corresponds to advancement of needle (100) to a position relative to cannula (50) to a predetermined amount of penetration within an eye of a patient. In other words, instrument (10) is configured such that an operator rotates knob (26) until knob (26) can no longer rotate, or until knob (26) begins to slip or "freewheel" in a clutch assembly, to properly position needle (100) within an eye of a patient. In some examples, the predetermined amount of advancement of needle (100) relative to cannula (50) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm.

In addition or in the alternative, instrument (10) may be equipped with certain tactile feedback features to indicate to an operator when needle (100) has been advanced to certain predetermined distances relative to cannula (50). Accordingly, an operator may determine the desired depth of penetration of needle (100) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

As also shown in FIG. 1, a pair of supply tubes (30, 40) extend proximally from actuator knob (26). In the present example, first supply tube (30) is configured to couple with a source of bleb fluid (340) (e.g., BSS); while second supply tube (40) is configured to couple with a source of therapeutic agent (341). It should be understood that each fluid supply tube (30, 40) may include a conventional luer feature and/or other structures permitting fluid supply tubes (30, 40) to be coupled with respective fluid sources. Fluid supply tubes (30, 40) lead to a valve assembly that includes actuation arms (24). Actuation arms (24) are pivotable to selectively change the state of the valve assembly. Based on the pivotal position of actuation arms (24), the valve assembly is operable to selectively pinch or otherwise open/close the supply of fluid from fluid supply tubes (30, 40) to lumen (104) of needle (100). Thus, actuation arms (24) are operable to selectively control the delivery of bleb fluid (340) and therapeutic agent (341) via needle (100). By way of example only, the valve assembly may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein. Other suitable features and configurations that may be used to control fluid delivery via needle (100) will be apparent to those of ordinary skill in the art in view of the teachings herein.

It should be understood that the features and operability of instrument (10) may be varied in numerous ways. In addition, instrument (10) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those of ordinary skill in the art in view of the teachings herein.

II. Exemplary Procedure for Subretinal Administration of Therapeutic Agent

FIGS. 4A-5C show an exemplary procedure for subretinal delivery of therapeutic agent from a suprachoroidal approach using instrument (10) described above. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 4A:
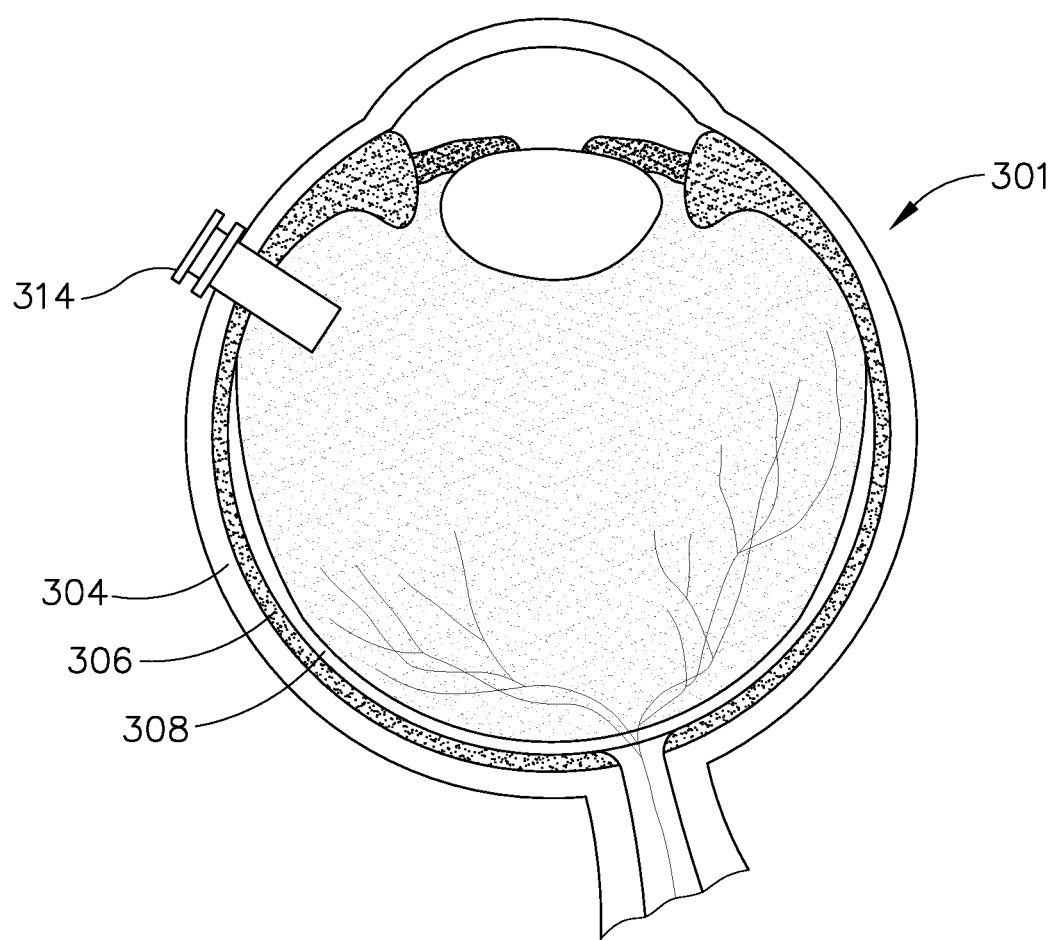
FIG. 4A depicts a cross-sectional view of an eye of a patient, with a chandelier installed in the eye.

In the present example, the procedure begins by an operator immobilizing tissue surrounding a patient's eye (301) (e.g., the eyelids) using a speculum, and/or any other instrument suitable for immobilization. While immobilization described herein with reference to tissue surrounding eye (301), it should be understood that eye (301) itself may remain free to move. Once the tissue surrounding eye (301) has been immobilized, an eye chandelier port (314) is inserted into eye (301), as shown in FIG. 4A, to provide intraocular illumination when the interior of eye (301) is viewed through the pupil. In the present example, eye chandelier port (314) is positioned in the inferior medial quadrant such that a superior temporal quadrant sclerotomy may be performed. Eye chandelier port (314) is positioned to direct light onto the interior of eye (301) to illuminate at least a portion of the retina (e.g., including at least a portion of the macula). As will be understood, such illumination corresponds to an area of eye (301) that is being targeted for delivery of therapeutic agent.

In the present example, only chandelier port (314) is inserted at the stage shown in FIG. 4A, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. Although FIG. 4A shows a particular positioning of eye chandelier port (314), it should be understood that eye chandelier port (314) may have any other positioning as will be apparent to those of ordinary skill in the art in view of the teachings herein.

Figure 4B:
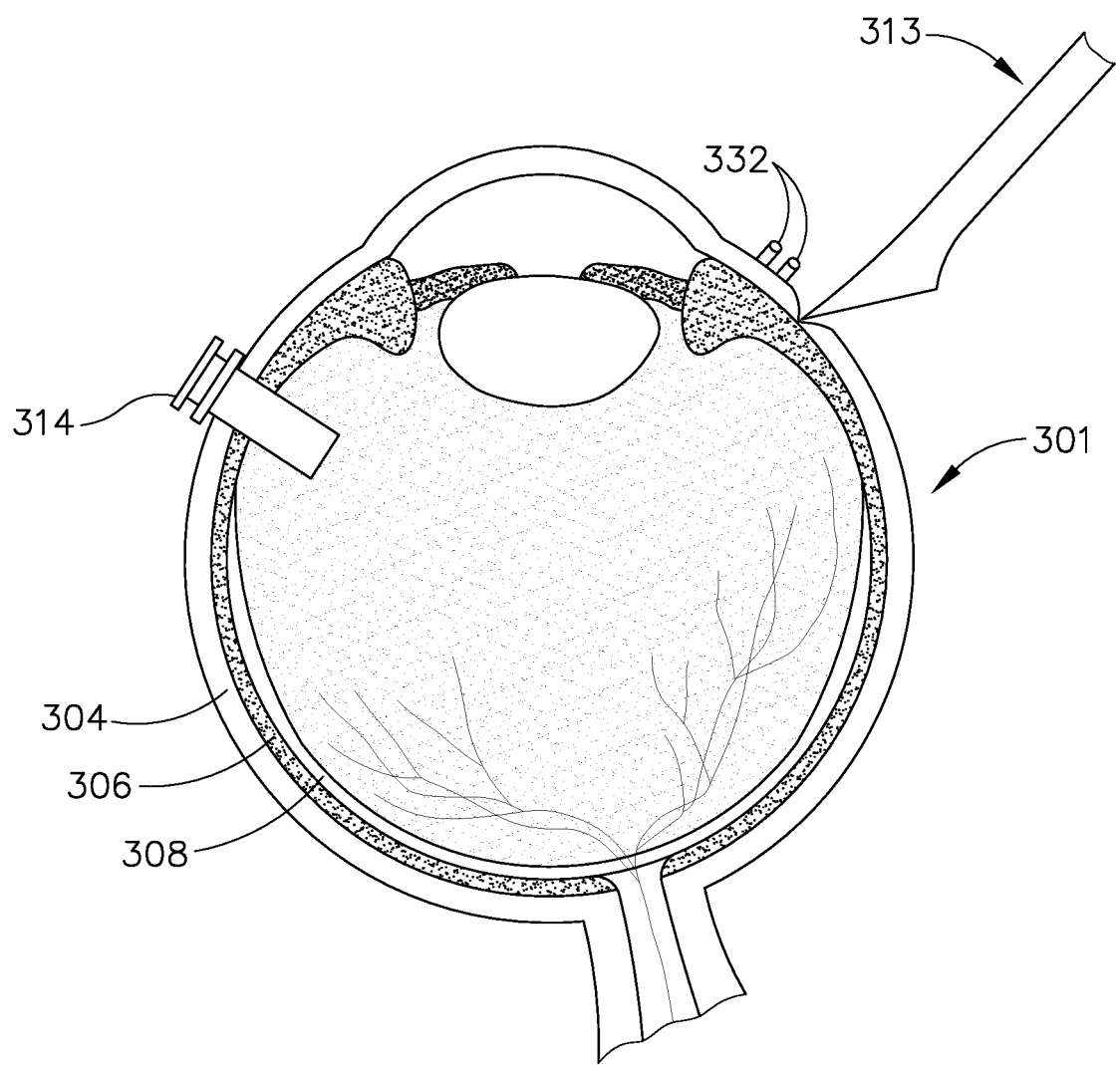
FIG. 4B depicts a cross-sectional view of the eye of FIG. 4A, with a suture loop attached to the eye, and with a sclerotomy being performed.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. A template may then be used to mark eye (301), as described in U.S. Pub. No. 2015/0223977, entitled "Method and Apparatus for Subretinal Administration of Therapeutic Agent," published Aug. 13, 2015, the disclosure of which is incorporated by reference herein. An operator may then use a visual guide created using the template to attach a suture loop assembly (332) and to perform a sclerotomy, as shown in FIG. 4B, using a conventional scalpel (313) or other suitable cutting instrument. The sclerotomy procedure forms a small incision through sclera (304) of eye (301). The sclerotomy is performed with particular care to avoid penetration of the choroid (306). Thus, the sclerotomy procedure provides access to the space between sclera (304) and choroid (306). Once the incision is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 4C:
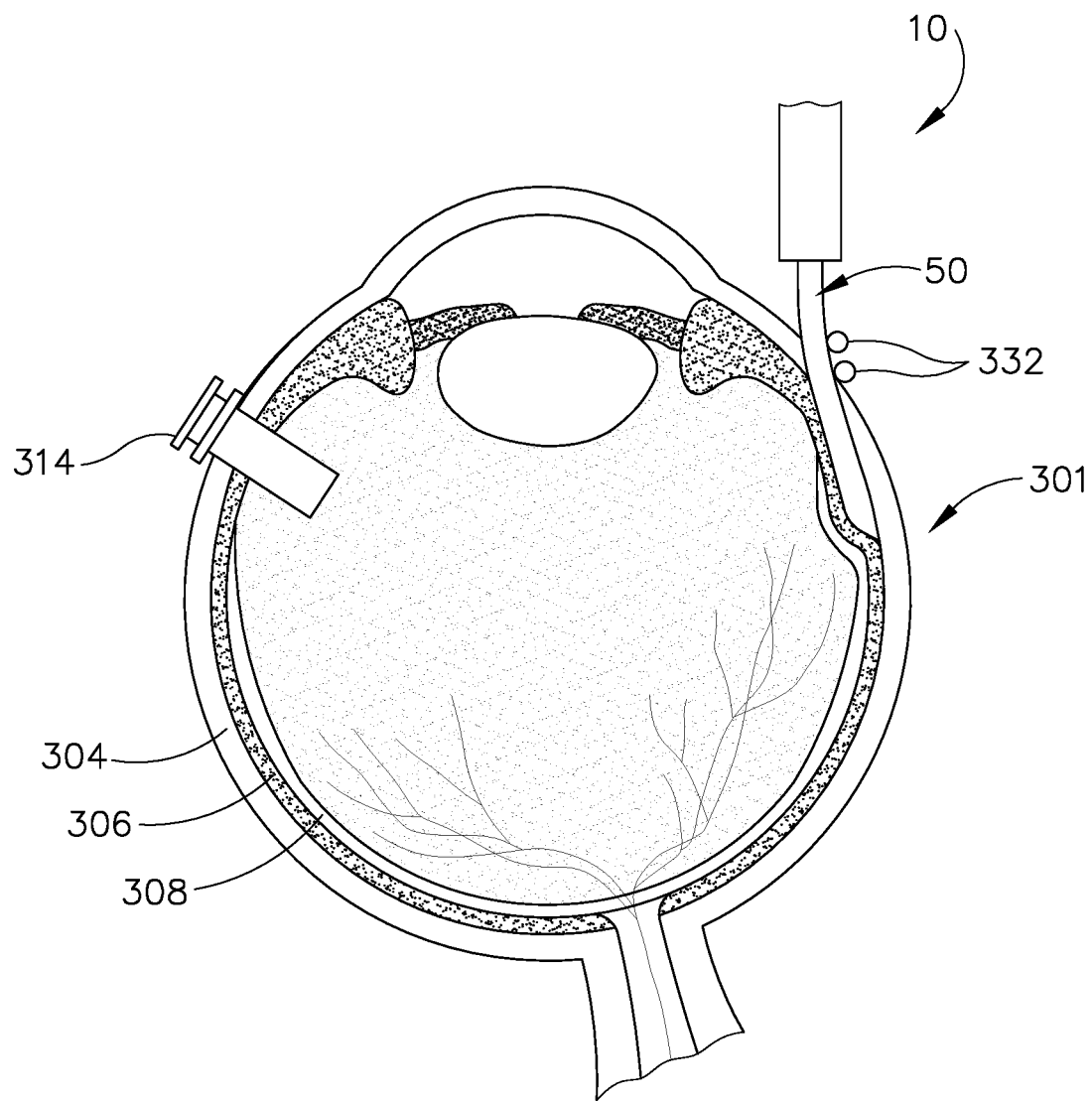
FIG. 4C depicts a cross-sectional view of the eye of FIG. 4A, with the instrument of FIG. 1 being inserted through the sclerotomy opening and in between the sclera and choroid of the eye.

With the sclerotomy procedure performed, an operator may insert cannula (50) of instrument (10) through incision (316) and into the space between sclera (304) and choroid (306). As can be seen in FIG. 4C, cannula (50) is directed through suture loop assembly (332) and into the incision. Suture loop assembly (332) may stabilize cannula (50) during insertion. Additionally, suture loop assembly (332) maintains cannula (50) in a generally tangential orientation relative to the incision. Such tangential orientation may reduce trauma as cannula (50) is guided through the incision. As cannula (50) is inserted into the incision through suture loop assembly (332), an operator may use forceps or other instruments to further guide cannula (50) along an atraumatic path. Of course, use of forceps or other instruments is merely optional, and may be omitted in some examples.

Although not shown, it should be understood that in some examples cannula (50) may include one or more markers on the surface of cannula (50) to indicate various depths of insertion. While merely optional, such markers may be desirable to aid an operator in identifying the proper depth of insertion as cannula (50) is guided along an atraumatic path. For instance, the operator may visually observe the position of such markers in relation to suture loop assembly (332) and/or in relation to the incision in the sclera (304) as an indication of the depth to which cannula (50) is inserted in eye (301). By way of example only, one such marker may correspond to an approximately 6 mm depth of insertion of cannula (50).

Figure 4D:
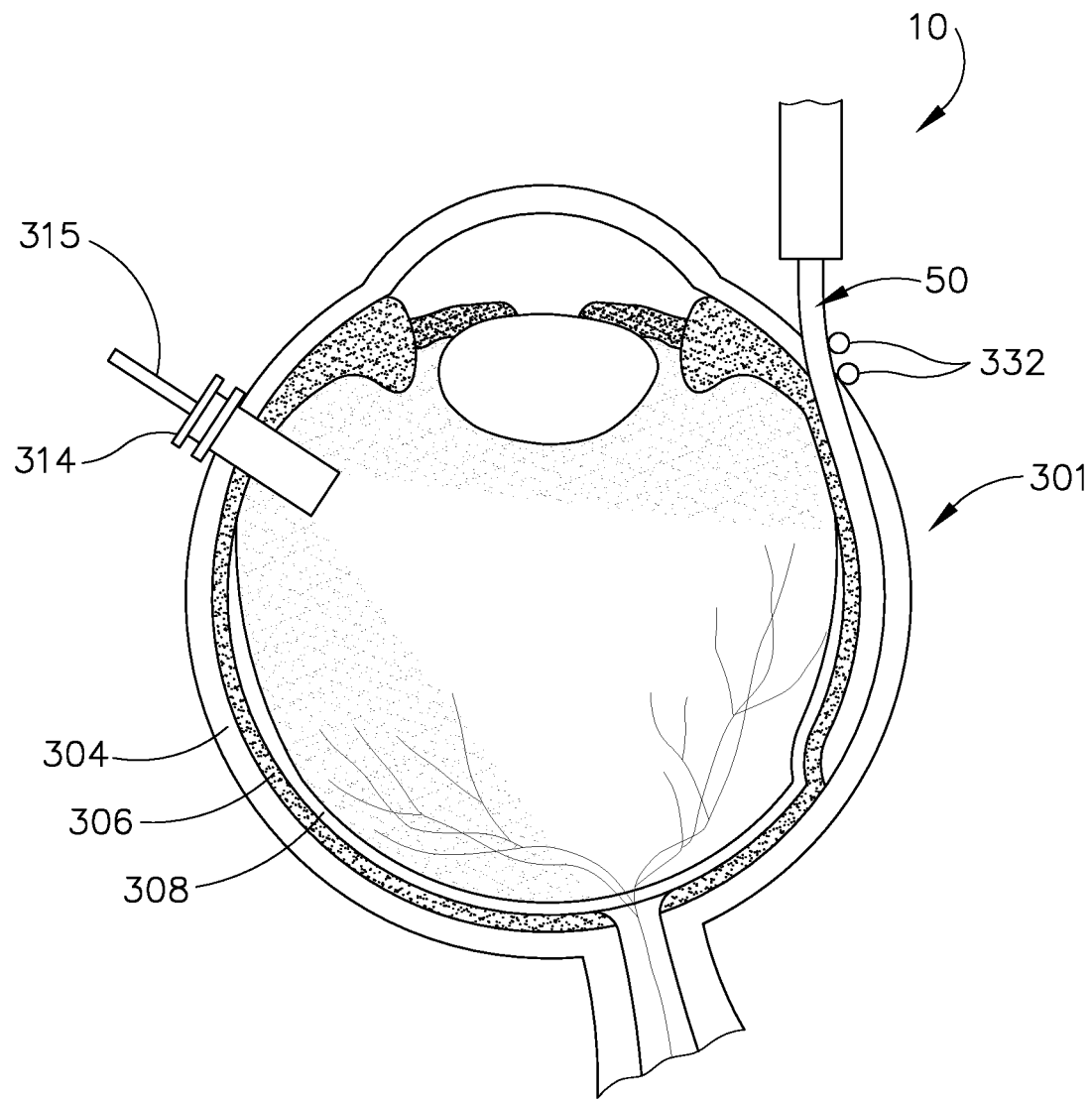
FIG. 4D depicts a cross-sectional view of the eye of FIG. 4A, with the instrument of FIG. 1 under direct visualization at the back of the eye, between the sclera and choroid.

As shown in FIG. 4D, once cannula (50) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (50) may optionally be made at this point to ensure proper positioning relative to the area of geographic atrophy of retina (308). In some instances, the operator may wish to rotate the eye (301), such as by pulling on suture loop assembly (332), to direct the pupil of the eye (301) toward the operator in order to optimize visualization of the interior of the eye (301) via the pupil.

FIGS. 4C-4D show cannula (50) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. By way of example only, the operator may rely on direct visualization through a microscope directed through the pupil of eye (301) as cannula (50) is being advanced through the range of motion shown in FIGS. 4C-4D, with illumination provided through fiber (315) and port (314). Cannula (50) may be at least partially visible through a retina (308) and choroid (306) of eye (301). Visual tracking may be enhanced in versions where an optical fiber is used to emit visible light through the distal end of cannula (50).

Figure 4E:
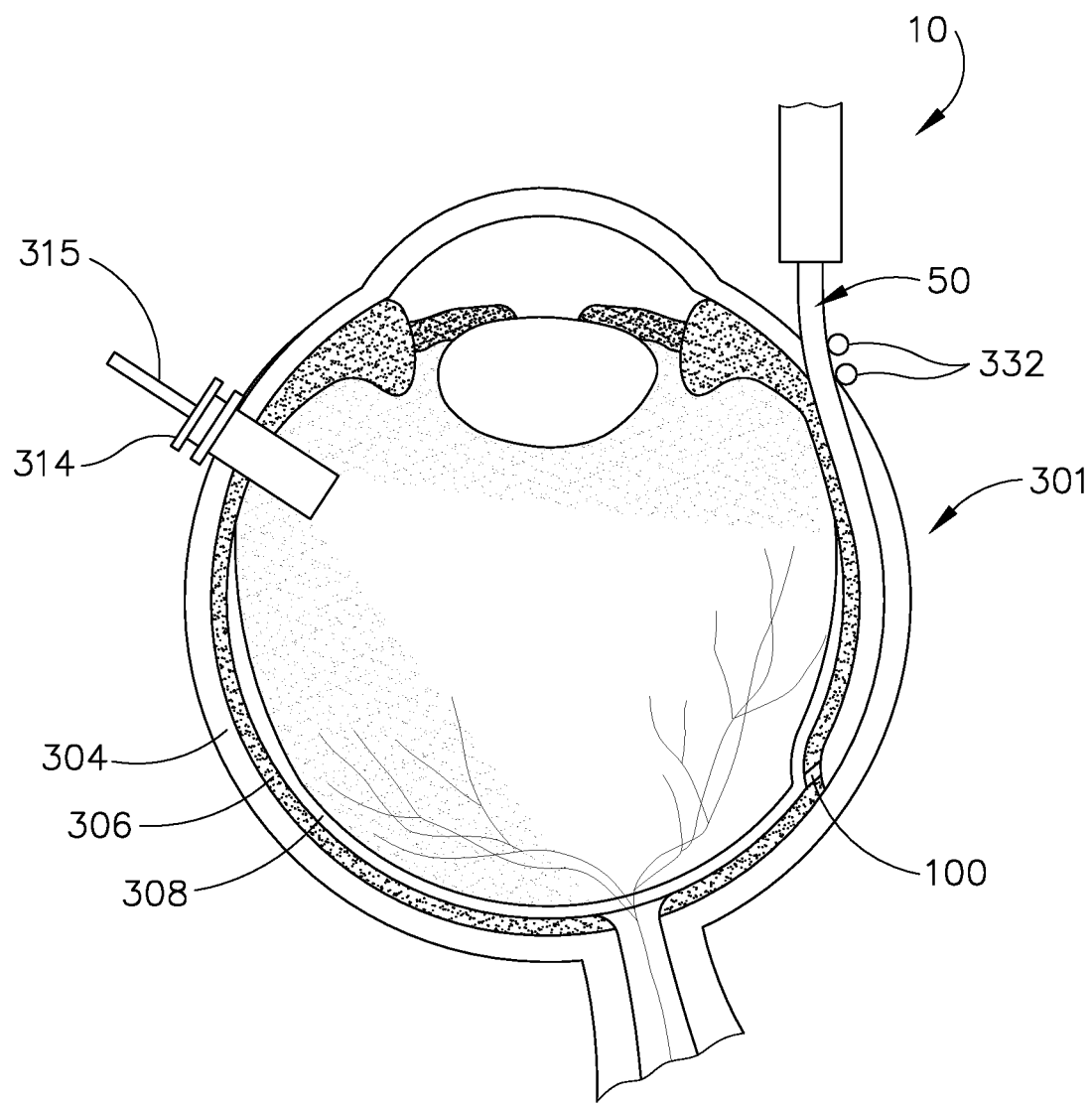
FIG. 4E depicts a cross-sectional view of the eye of FIG. 4A, with the needle of the instrument of FIG. 1 being advanced under direct visualization at the back of the eye, pressing against the outer surface of the choroid causing the choroid to "tent"
Figure 5A:
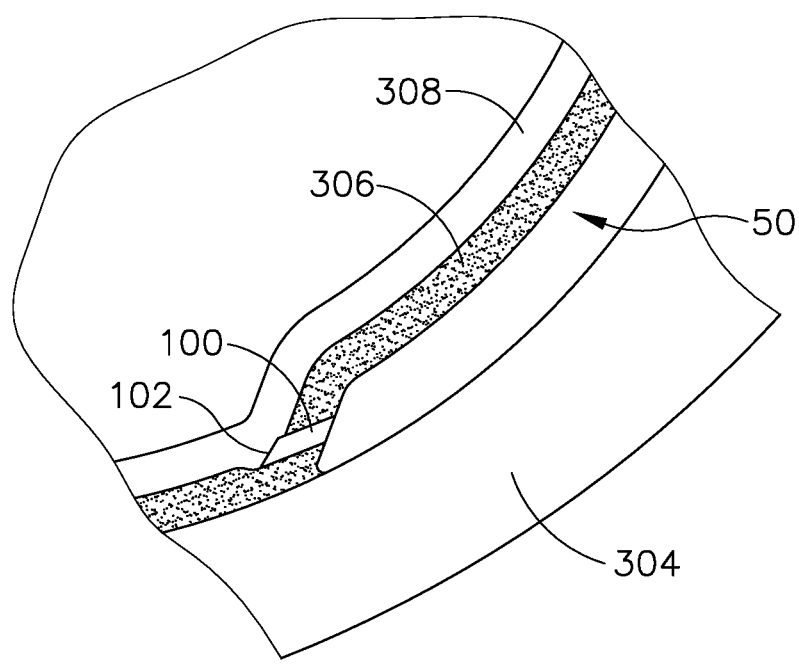
FIG. 5A depicts a detailed cross-sectional view of the eye of FIG. 4A depicted in the state shown in FIG. 4E.

Once cannula (50) has been advanced to the delivery site as shown in FIG. 4D, an operator may advance needle (100) of instrument (10) as described above by actuating knob (26). As can be seen in FIGS. 4E and 5A, needle (100) is advanced relative to cannula (50) such that needle (100) pierces through choroid (306) without penetrating retina (308). Immediately prior to penetrating choroid (306), needle (100) may appear under direct visualization as "tenting" the surface of choroid (306). In other words, needle (100) may deform choroid (306) by pushing upwardly on choroid (306), providing an appearance similar to a tent pole deforming the roof of a tent. Such a visual phenomenon may be used by an operator to identify whether choroid (306) is about to be pierced and the location of any eventual piercing. The particular amount of needle (100) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (100) advancement may be between approximately 0.25 mm and approximately 10 mm; or more particularly between approximately 2 mm and approximately 6 mm.

Figure 4F:
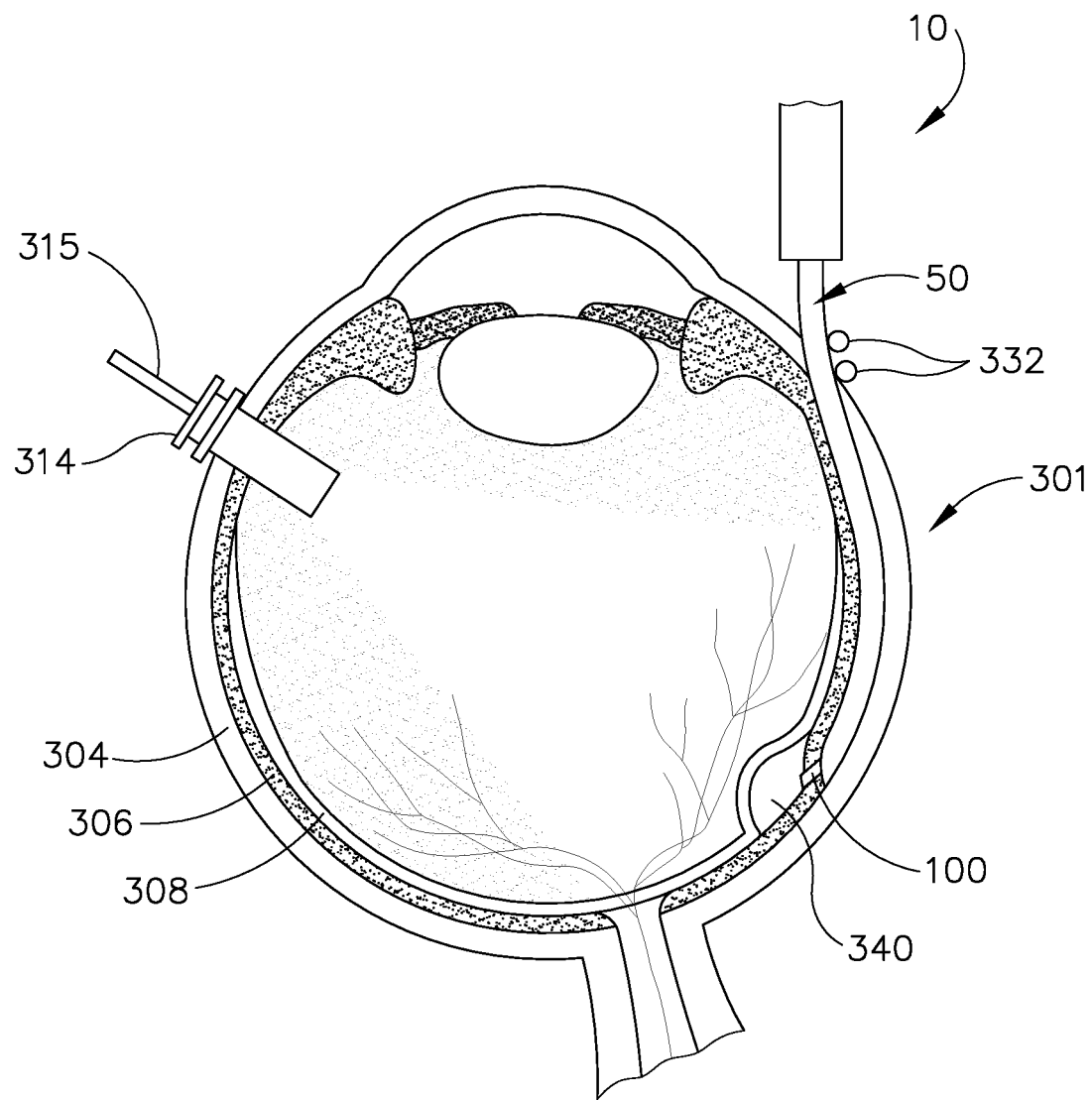
FIG. 4F depicts a cross-sectional view of the eye of FIG. 4A, with the needle dispensing a leading bleb under direct visualization at the back of the eye, the needle between the sclera and choroid, and the leading bleb in the subretinal space between the choroid and a retina.
Figure 5B:
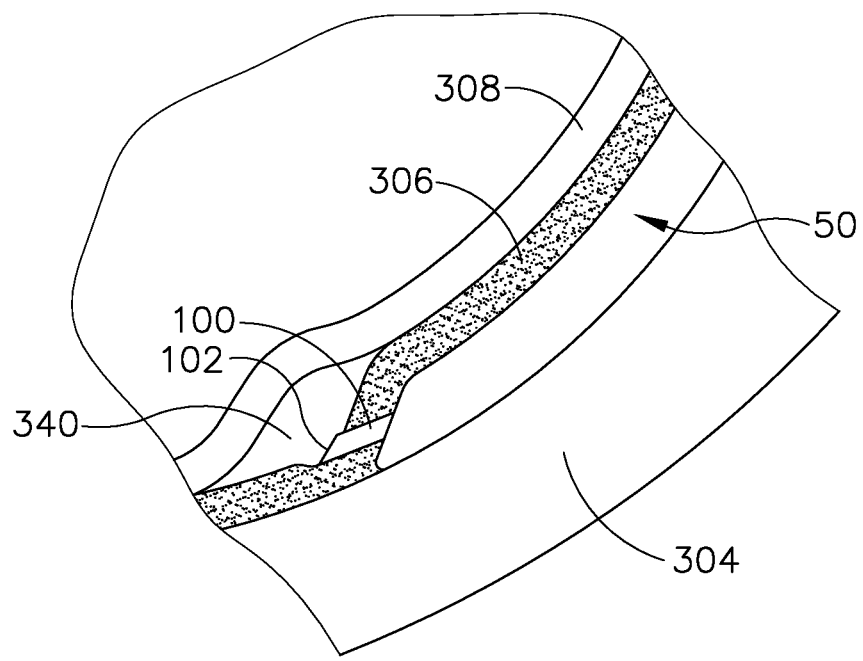
FIG. 5B depicts a detailed cross-sectional view of the eye of FIG. 4A depicted in the state shown in FIG. 4F.

In the present example, after the operator has confirmed that needle (100) has been properly advanced by visualizing the tenting effect described above, the operator infuses a balanced salt solution (BSS) or other similar solution as needle (100) is advanced relative to cannula (50). Such a BSS may form a leading bleb (340) ahead of needle (100) as needle (100) is advanced through choroid (306). Leading bleb (340) may be desirable for two reasons. First, as shown in FIGS. 4F and 5B, leading bleb (340) may provide a further visual indicator to an operator to indicate when needle (100) is properly positioned at the delivery site. Second, leading bleb (340) may provide a barrier between needle (100) and retina (308) once needle (100) has penetrated choroid (306). Such a barrier may push the retinal wall outwardly, thereby minimizing the risk of retinal perforation as needle (100) is advanced to the delivery site. In some versions, a foot pedal is actuated in order to drive leading bleb (340) out from needle (100). Alternatively, other suitable features that may be used to drive leading bleb (340) out from needle (100) will be apparent to those of ordinary skill in the art in view of the teachings herein.

Once the operator visualizes leading bleb (340), the operator may cease infusion of BSS, leaving a pocket of fluid as can be seen in FIGS. 4F and 5B. Next, a therapeutic agent (341) may be infused by actuating a syringe or other fluid delivery device as described in various references cited herein. The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. In addition to, or as an alternative to, being used to deliver a therapeutic agent (341), instrument (10) and variations thereof may be used to provide drainage and/or perform other operations.

Figure 4G:
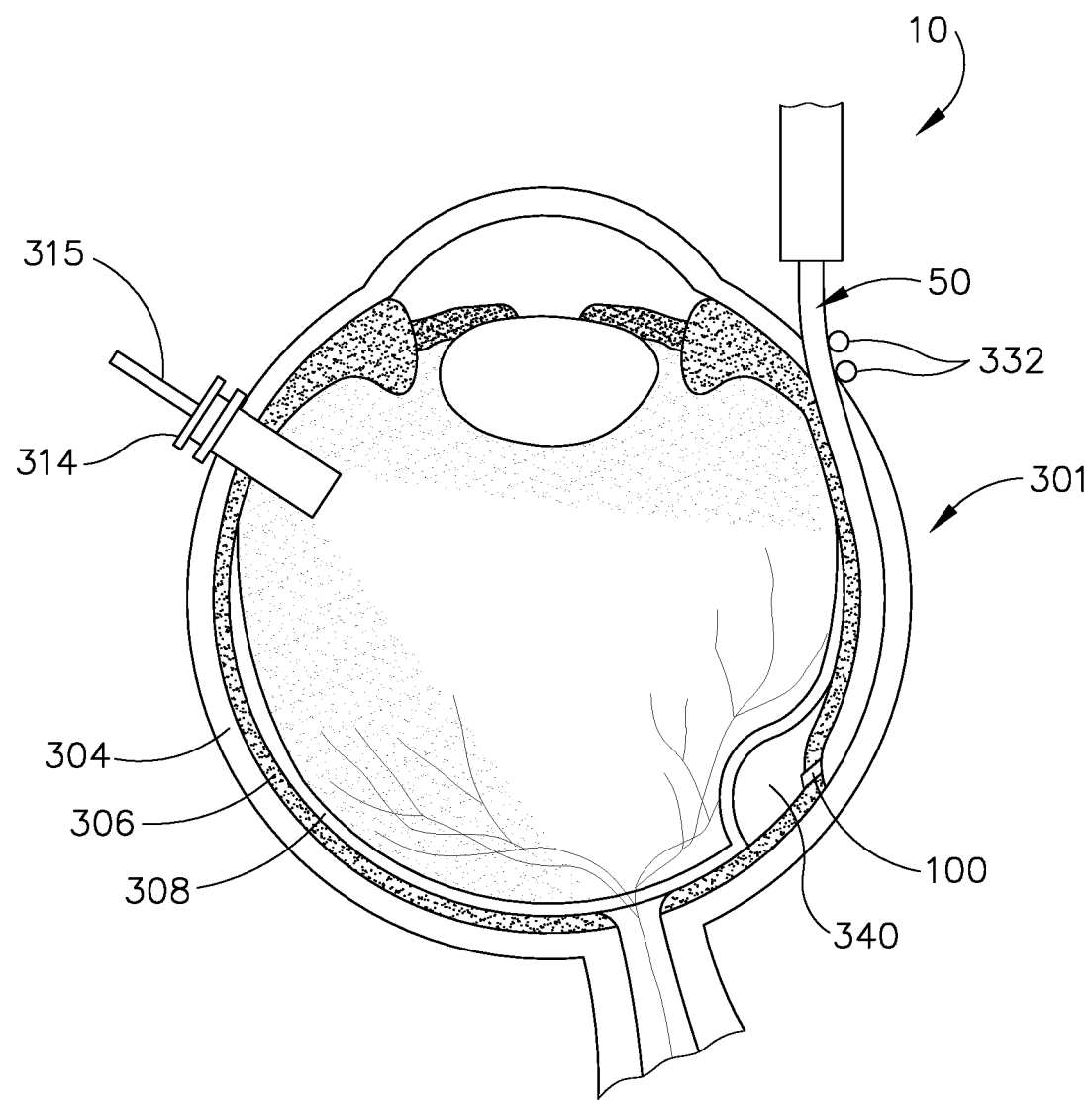
FIG. 4G depicts a cross-sectional view of the eye of FIG. 4A, with the needle dispensing a therapeutic agent to the eye at the back of the eye, between the sclera and choroid.
Figure 5C:
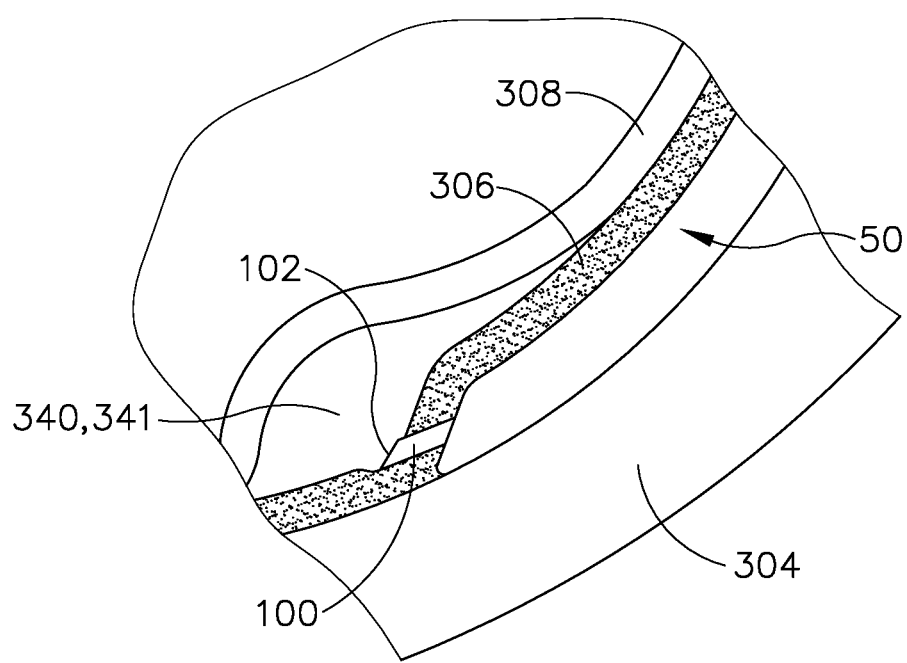
FIG. 5C depicts a detailed cross-sectional view of the eye of FIG. 4A depicted in the state shown in FIG. 4G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (100). Alternatively, other suitable features that may be used to drive agent (341) out from needle (100) will be apparent to those of ordinary skill in the art in view of the teachings herein. Delivery of therapeutic agent (341) may be visualized by an expansion of the pocket of fluid as can be seen in FIGS. 4G and 5C. As shown, therapeutic agent (341) essentially mixes with the fluid of leading bleb (340) as therapeutic agent (341) is injected into the suprachoroidal, subretinal space.

Once delivery is complete, needle (100) may be retracted by rotating knob (26) in a direction opposite to that used to advance needle (100); and cannula (50) may then be withdrawn from eye (301). It should be understood that because of the size of needle (100), the site where needle (100) penetrated through choroid (306) is self sealing, such that no further steps need be taken to seal the delivery site through choroid (306). Suture loop assembly (332) and chandelier (314) may be removed, and the incision in the sclera (304) may be closed using any suitable conventional techniques.

As noted above, the foregoing procedure may be carried out to treat a patient having macular degeneration. In some such instances, the therapeutic agent (341) that is delivered by needle (100) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (100) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

It should also be understood that the procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein.

III. Exemplary Injector System with Remote Control

In some versions of the procedure described above with reference to FIGS. 4A-4G and 5A-5C, the patient may be awake and under local anesthetic. In such instances, there is a risk of patient movement. Such patient movement while cannula (50) is disposed in the eye (301) may result in damage to the eye. In addition, operation of instrument (10) requires manual manipulation of actuation arms (24) and actuation knob (26). Such manually operable features may present a risk of unintended movement of cannula (50) within the eye (301). In addition, there may be difficulty in consistently achieving precise administration of bleb fluid (340) and therapeutic agent (341). It may therefore be desirable to mitigate risks associated with patient movement, to mitigate the risk of unintended movement of components that are disposed in the eye (301), and to enhance the consistency in the precision of administration of bleb fluid (340) and therapeutic agent (341).

A. Overview

Figure 6:
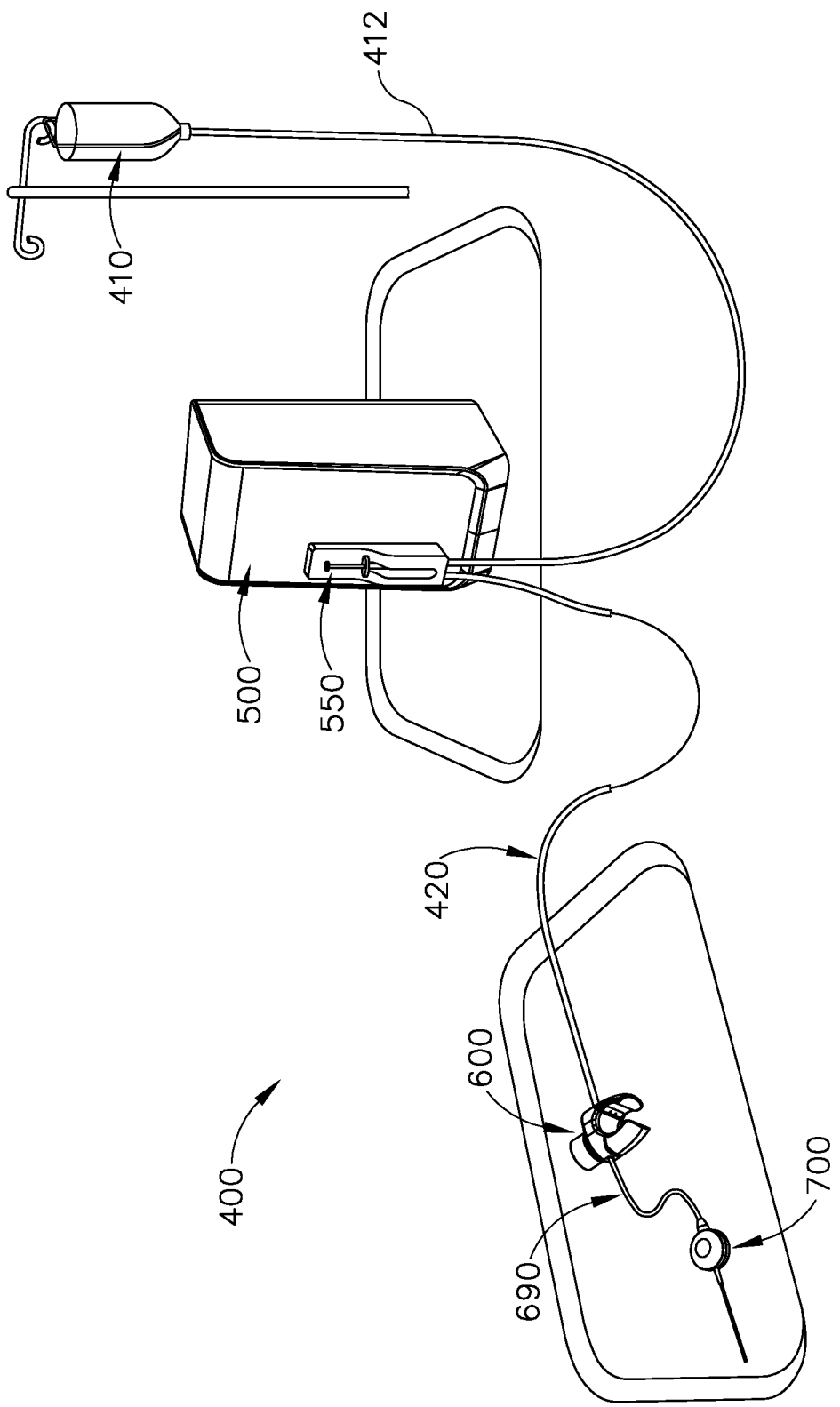
FIG. 6 depicts a perspective view of an exemplary system for subretinal administration of a therapeutic agent from a suprachoroidal approach.

FIG. 6 shows an exemplary system (400) that may be used to deliver bleb fluid (340) and therapeutic agent (341) into the eye (301) of a patient. System (400) of this example includes a control module (500), an injector driver assembly (600), and an injector assembly (700). A syringe actuation cassette (550) is disposed in control module (500) and is coupled with injector driver assembly (600) via a tube set (420). Syringe actuation cassette (550) is also coupled with a balanced salt solution (BSS) bottle (410) via a conduit (412). Injector assembly (700) is coupled with injector driver assembly (600) via a tube and cable assembly (690). Each of these components will be described in greater detail below.

Figure 7:
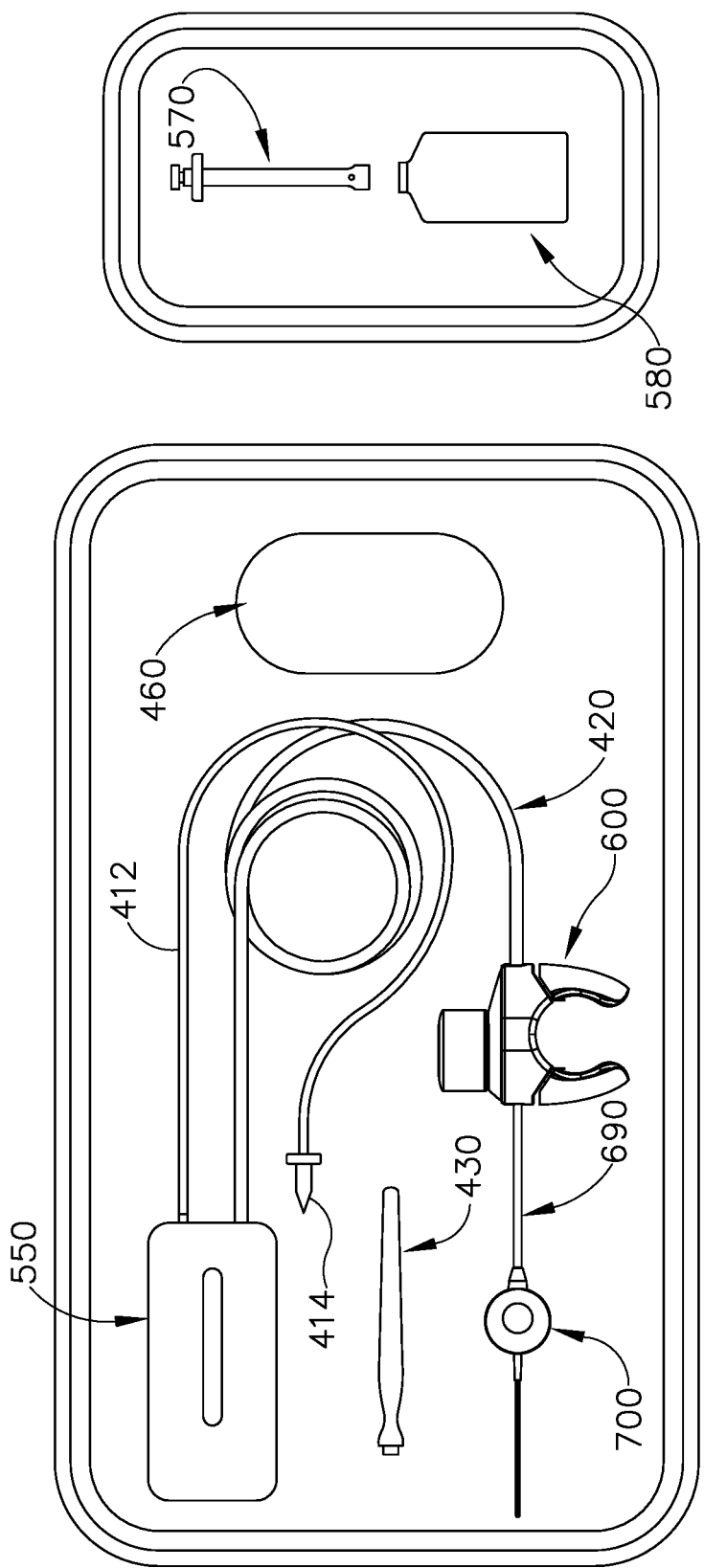
FIG. 7 depicts a top plan view of a kit containing some components of the system of FIG. 6.

As shown in FIG. 7, disposable components of system (400) may be provided in a sterile kit form. These components include syringe actuation cassette (550), conduit (412) with an integral spike (414), tube set (420), injector driver assembly (600), tube and cable assembly (690), and injector assembly (700). As shown, syringe actuation cassette (550), conduit (412) with an integral spike (414), tube set (420), injector driver assembly (600), tube and cable assembly (690), and injector assembly (700) may all be pre-coupled together in the sterile kit. The sterile kit of this example also includes a marking instrument (430), a magnetic pad (460), a syringe (570), and a syringe adapter (580). Marking instrument (430) is operable to mark certain locations on the eye (301), such as locations to install suture loop assembly (332). By way of example only, marking instrument (430) may be constructed and operable in accordance with the teachings of U.S. Pub. No. 2015/0223977, the disclosure of which is incorporated by reference herein. As another merely illustrative example, marking instrument (430) may be constructed and operable in accordance with the teachings of U.S. patent application Ser. No. 15/609,419, entitled "Guide Apparatus for Tangential Entry into Suprachoroidal Space," filed on May 31, 2017, published as U.S. Pub. No. 2017/0360605 on Dec. 21, 2017, the disclosure of which is incorporated by reference herein. The other components of the sterile kit shown in FIG. 7 will be described in greater detail below. As also shown in FIG. 7, another sterile kit may include a syringe (570) and a syringe adapter (580).

Figure 8:
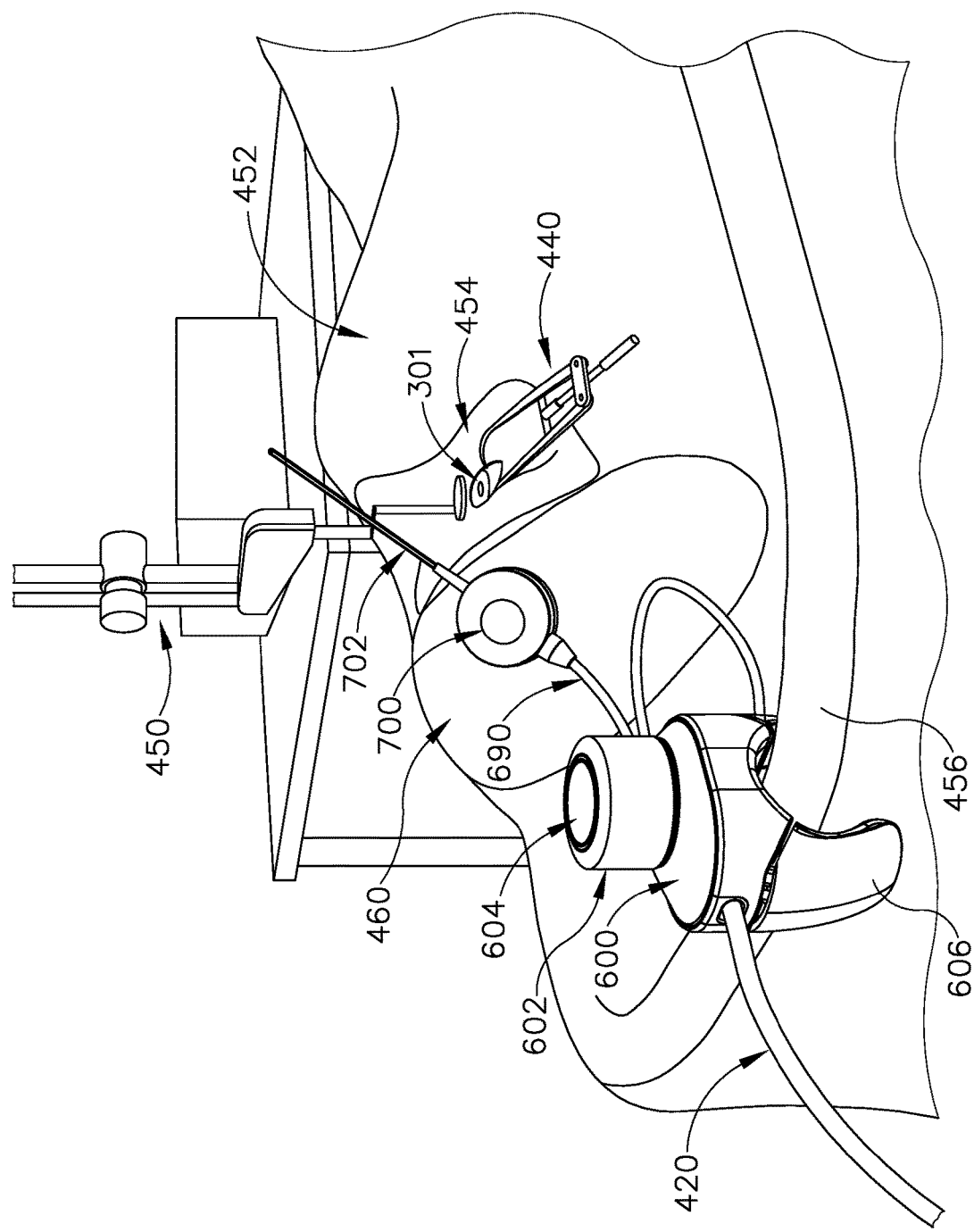
FIG. 8 depicts a perspective view of components of the system of FIG. 6 mounted near a patient.

FIG. 8 shows components of system (400) positioned in relation to a patient. In this example, a drape (452) is disposed over the patient, with an opening (454) formed in drape (452) near the patient's eye (301). A speculum (440) is used to keep the eye (301) open. A fixture (450) is positioned adjacent to the eye (301). Fixture (450) may be used to secure instrumentation, such as a viewing scope, relative to the patient. Magnetic pad (460) is adhered to drape (452) near the opening (454) adjacent to the eye (301). Injector assembly (700) is placed on magnetic pad (460), and is removably secured thereto via magnetic attraction as will be described in greater detail below. Injector assembly (700) is oriented to enable insertion of a flexible cannula (702) of injector assembly (700) into the eye (301). Injector driver assembly (600) is removably secured to a wrist rest (456) via arms (606). Injector driver assembly (600) is positioned close enough to injector assembly (700) to provide some degree of slack in tube and cable assembly (690). While not shown in FIG. 8, injector driver assembly (600) is coupled with control module (500) via syringe actuation cassette (550) and tube set (420).

B. Exemplary Control Module and Method of Use

Figure 9A:
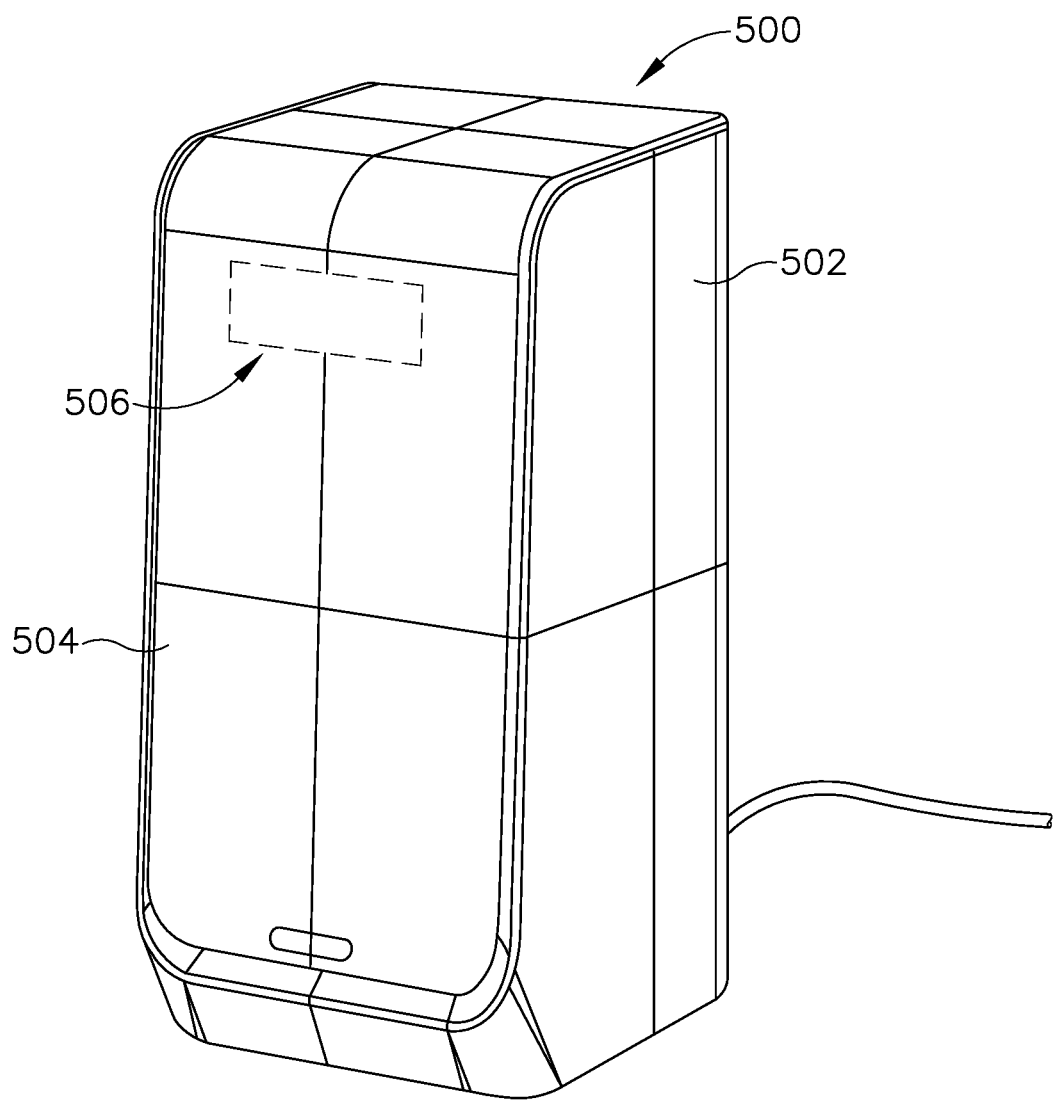
FIG. 9A depicts a perspective view of a control module of the system of FIG. 6 at a first stage of a procedure.
Figure 9B:
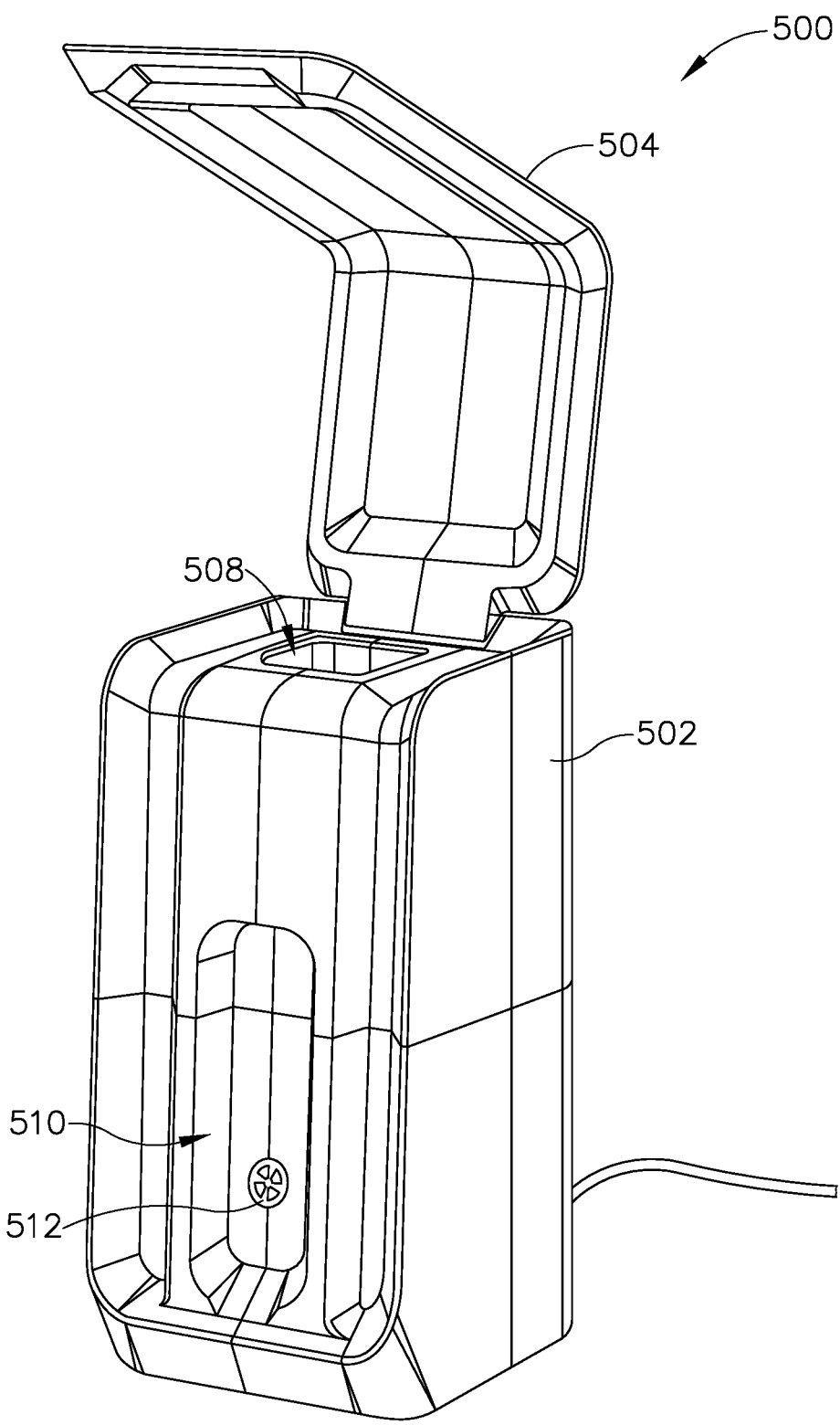
FIG. 9B depicts a perspective view of the control module of FIG. 9A, with a cover in an open position, at a second stage of the procedure of FIG. 9A.

As shown in FIGS. 9A-9B, control module (500) of the present example comprises a base (502) and a cover (504). Cover (504) is configured to pivot relative to base (502) between an open position (FIG. 9B) and a closed position (FIG. 9A). Cover (504) includes a display region (506) that is operable to display images, numbers, text, and/or other forms of information. As shown in FIG. 9B, base (502) includes a thawing chamber (508), a cassette receptacle (510), and a cassette actuator (512).

Thawing chamber (508) includes components that are operable to thaw a frozen therapeutic substance vial assembly (590) (e.g., using heated air). Various suitable components and arrangements that may be used to provide such thawing functionality will be apparent to those of ordinary skill in the art in view of the teachings herein.

Cassette receptacle (510) is configured to removably receive syringe actuation cassette (550). Cassette actuator (512) is configured to interact with complementary features of syringe actuation cassette (550) to selectively control delivery of bleb fluid (340) from bottle (410) to tube set (420). By way of example only, syringe actuation cassette (550) may comprise a pump that is actuated by cassette actuator (512) to drive bleb fluid (340) from bottle (410) to tube set (420). As another merely illustrative example, cassette (550) may be modified to receive a second syringe containing bleb fluid (340); and cassette actuator (512) may be configured to drive features of cassette (550) to expel bleb fluid (340) from the syringe containing bleb fluid (340). Other suitable ways in which cassette actuator (512) and syringe actuation cassette (550) may be configured to cooperate to provide controlled delivery of bleb fluid (340) through tube set (420) will be apparent to those of ordinary skill in the art in view of the teachings herein.

Cassette actuator (512) is further configured to interact with complementary features of syringe actuation cassette (550) to selectively control delivery of therapeutic agent (341) from syringe (570) to tube set (420). By way of example only, syringe actuation cassette (550) or control module (500) may include a lead screw that is operable to actuate plunger (574) to thereby drive therapeutic agent (341) from syringe (570) to tube set (420). Other suitable components and arrangements that may be used to provide such fluid delivery control functionality will be apparent to those of ordinary skill in the art in view of the teachings herein.

Cassette actuator (512) of the present example further includes a coupling feature that is operable to receive data from electric cable (426) when syringe actuation cassette (550) is fully seated in cassette receptacle (510). Examples of such data will be described in greater detail below. It should also be understood that control module (500) may provide power or signals through electrical cable (426).

Figure 9C:
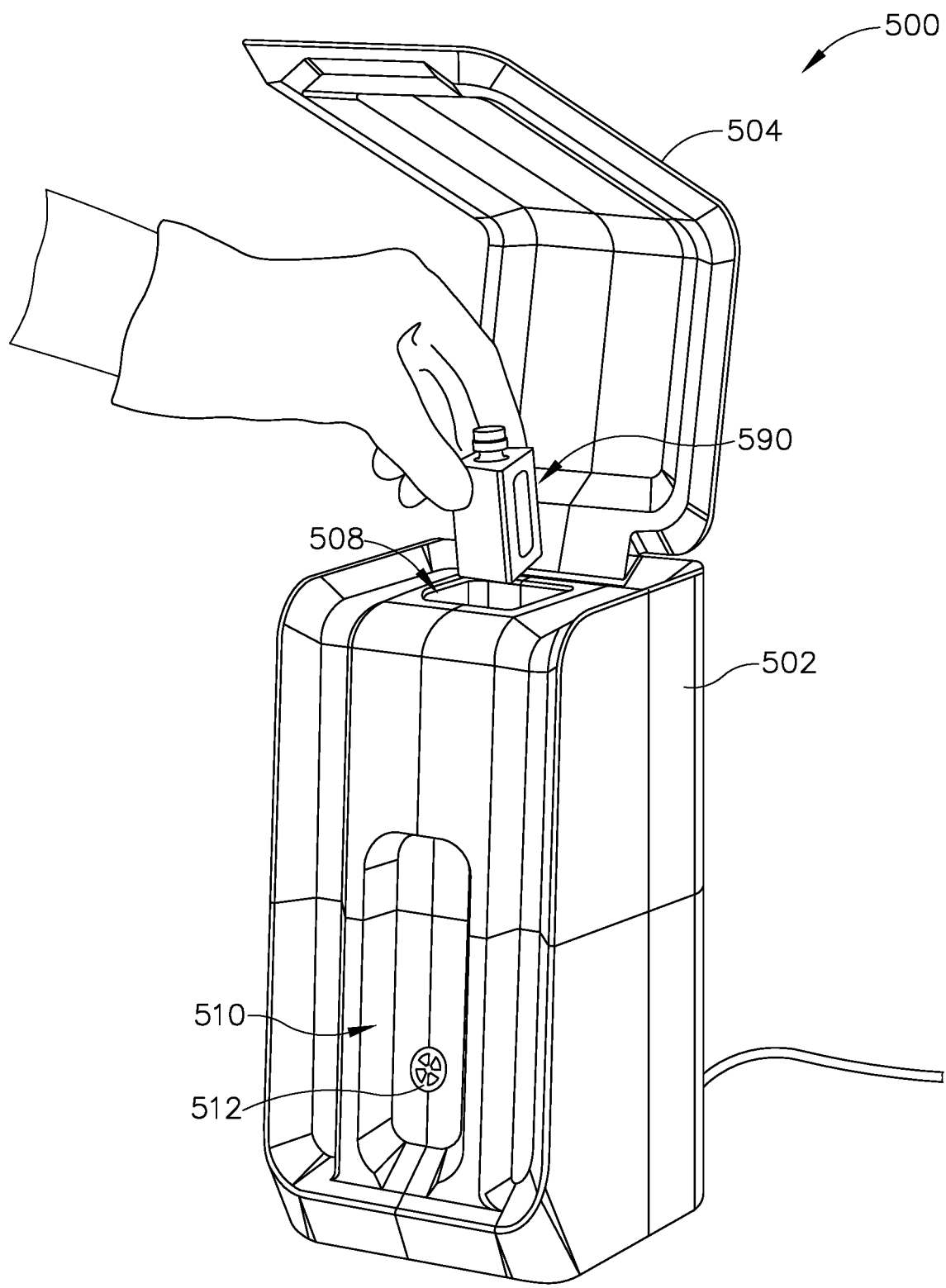
FIG. 9C depicts a perspective view of the control module of FIG. 9A, with the cover in the open position, and with a therapeutic substance vial being inserted into a thawing chamber of the control module, at a third stage of the procedure of FIG. 9A.

In an exemplary method of use, control module (500) is initially provided with cover (504) in the closed position, as shown in FIG. 9A. The operator then opens cover (504) as shown in FIG. 9B. With cover (504) in the open position, the operator inserts a therapeutic substance vial assembly (590) into thawing chamber (508), as shown in FIG. 9C. Therapeutic substance vial assembly (590) comprises a case (592) (FIG. 9E) containing a vial (594) (FIG. 9E), which contains a volume of frozen therapeutic agent (341).

Figure 9D:
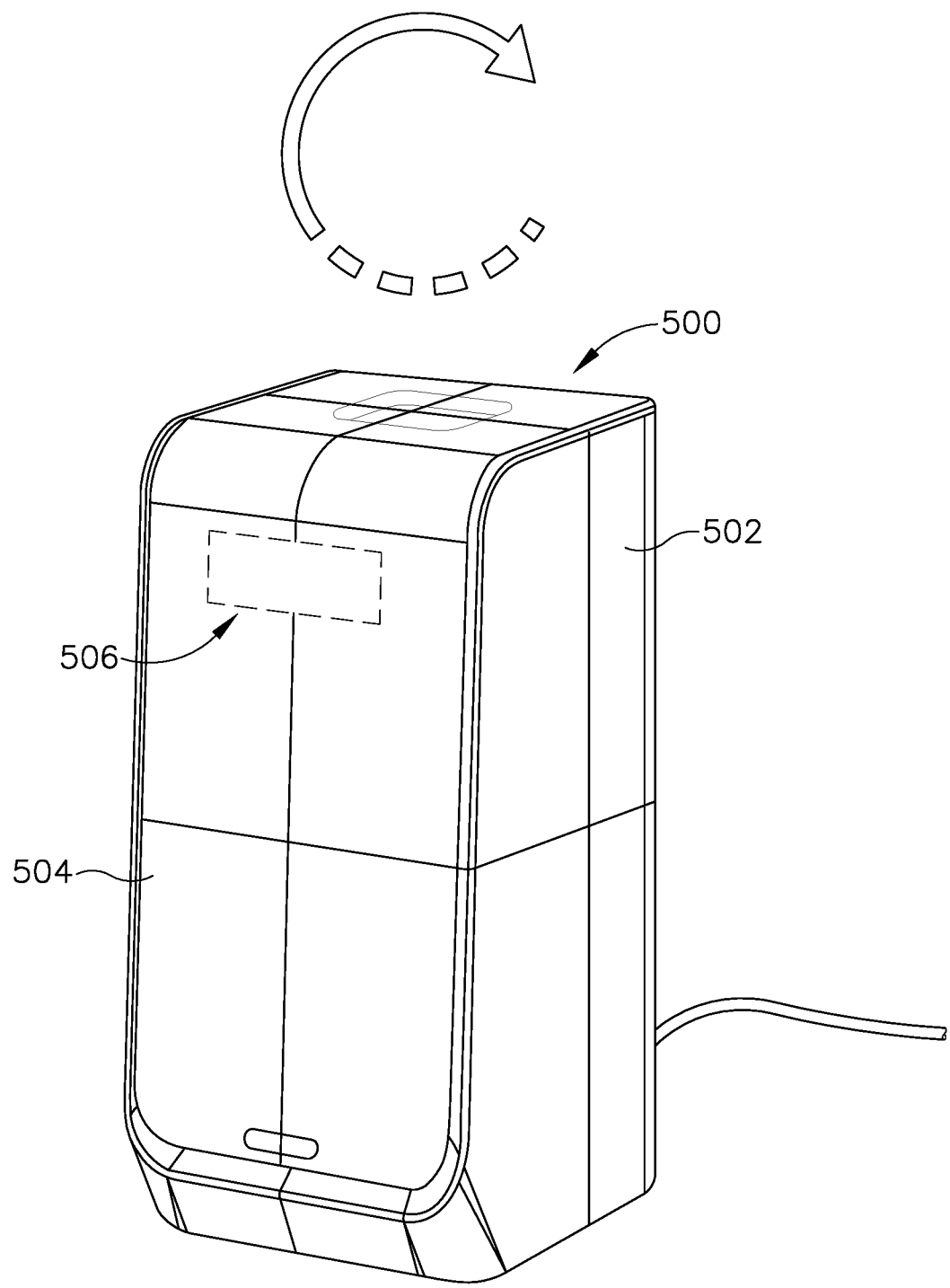
FIG. 9D depicts a perspective view of the control module of FIG. 9A, with the cover in a closed position, at a fourth stage of the procedure of FIG. 9A.

The operator then closes cover (504), as shown in FIG. 9D. This closure of cover (504) initiates a thawing sequence in thawing chamber (508), to thaw therapeutic agent (341) contained in therapeutic substance vial assembly (590). By way of example only, control module (500) may include an integrated heater-air thaw mechanism to thaw cryo-frozen cells in therapeutic agent (341) contained in therapeutic substance vial assembly (590). An infrared temperature sensor (or other kind of temperature sensor) may measure the exterior of therapeutic substance vial assembly (590) and ensure that the temperature never exceeds 37° C., to protect the cells in therapeutic agent (341). During the thawing sequence, display region (506) displays the amount of time remaining until completion of the thawing sequence. After the thaw is complete, the operator opens cover (504) and removes therapeutic substance vial assembly (590) from thawing chamber (508).

Figure 9E:
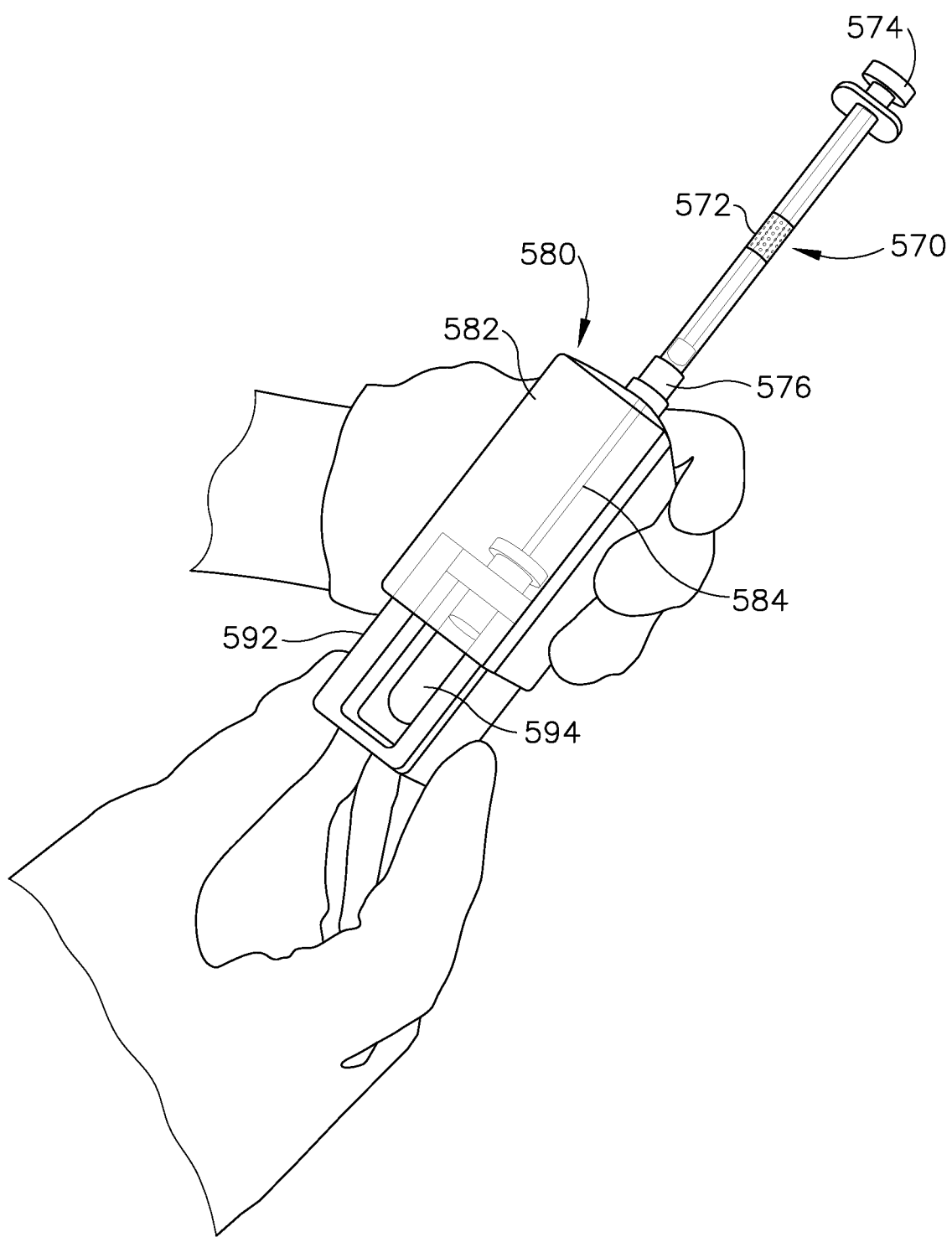
FIG. 9E depicts a perspective view of the therapeutic substance vial of FIG. 9C being inserted into a syringe adapter, at a fifth stage of the procedure of FIG. 9A.

Next, the operator positions thawed therapeutic substance vial assembly (590) into a body (582) of syringe adapter (580), as shown in FIG. 9E. Body (582) has a configuration that complements the configuration of case (592), such that therapeutic substance vial assembly (590) may be freely inserted into body (582). As shown in FIG. 9E, syringe adapter (580) further includes an integral needle (584) that is rigidly secured to body (582). Needle (584) is positioned such that needle (584) will pierce a septum of vial (594) as substance vial assembly (590) is fully inserted into body (582). Needle (584) is also positioned and fixedly secured to body (582) such that needle (584) will not contact interior surfaces of vial (594), thereby eliminating the risk of needle (584) inadvertently skiving off of sidewalls of vial (594) and generating particulate, etc.

As also shown in FIG. 9E, syringe (570) of the present example includes a body (572) with a plunger (574) and a distal fitting (576). Plunger (574) is configured to reciprocate relative to body (572) to selectively draw fluid into body (572) or expel fluid from body (572). Distal fitting (576) is configured to removably couple with a proximal end of body (582). When distal fitting (576) is coupled with the proximal end of body (582), distal fitting (576) is in fluid communication with needle (584), thereby placing body (572) in fluid communication with needle (584).

Figure 9F:
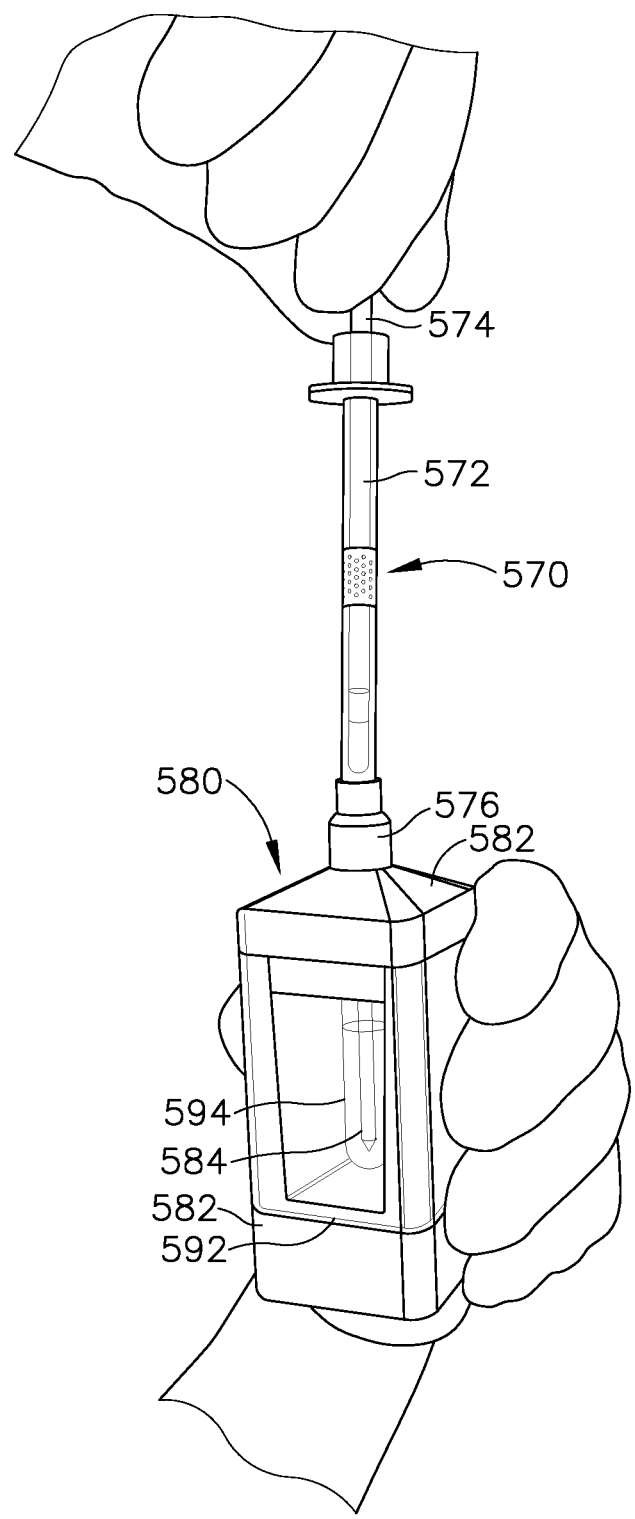
FIG. 9F depicts a perspective view of a syringe extracting a therapeutic substance from the therapeutic substance vial of FIG. 9C via the syringe adapter of FIG. 9E, at a sixth stage of the procedure of FIG. 9A.

FIG. 9F shows substance vial assembly (590) fully seated in syringe adapter (580). It should be understood that the complementary configurations of vial assembly (590) and syringe adapter (580) may provide self-centering of substance vial assembly (590) in syringe adapter (580) and depth control of needle (584) in vial (594) as substance vial assembly (590) reaches the fully seated position. With substance vial assembly (590) fully seated in syringe adapter (580), the operator retracts plunger (574) proximally while holding the other components stationary. This draws therapeutic agent (341) from vial (594) into body (572) of syringe (570) via needle (584) and distal fitting (576).

Figure 9G:
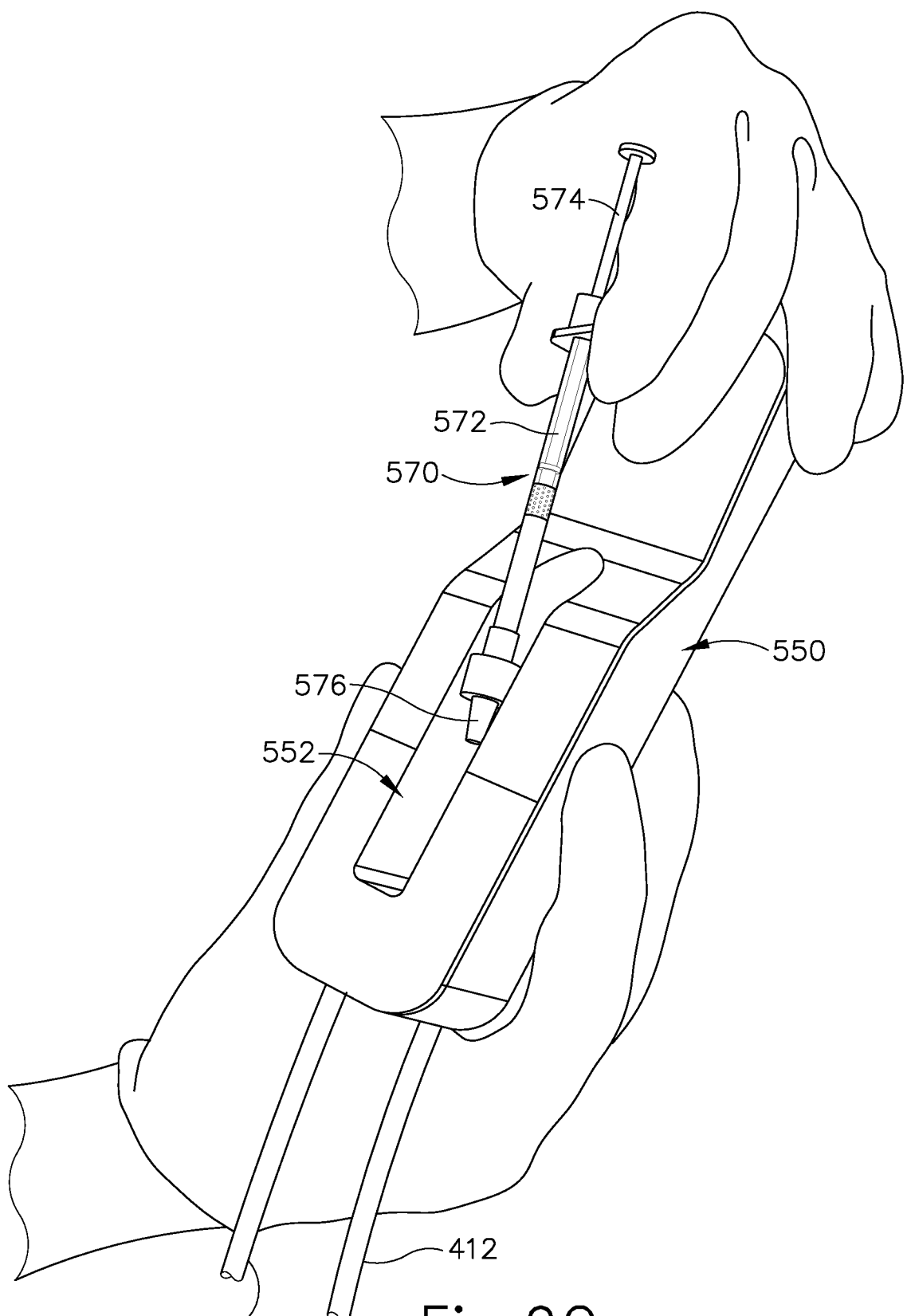
FIG. 9G depicts a perspective view of the syringe of FIG. 9F being inserted into a syringe actuation cassette, at a seventh stage of the procedure of FIG. 9A.

After the operator has transferred a suitable amount of therapeutic agent (341) from vial (594) to body (572) of syringe (570), the operator positions syringe (570) in a syringe receiving receptacle (552) of syringe actuation cassette (550), as shown in FIG. 9G. Distal fitting (576) is oriented toward a bottom portion of syringe receiving receptacle (552). As also shown in FIG. 9G, tube set (420) and conduit (412) extend from the bottom portion of syringe actuation cassette (550). As will be described in greater detail below, tube set (420) contains a first conduit (422) that is configured to communicate bleb fluid (340), a second conduit (424) that is configured to communicate therapeutic agent (341), and an electric cable (426) that is configured to communicate electrical power and/or data signals.

Figure 9H:
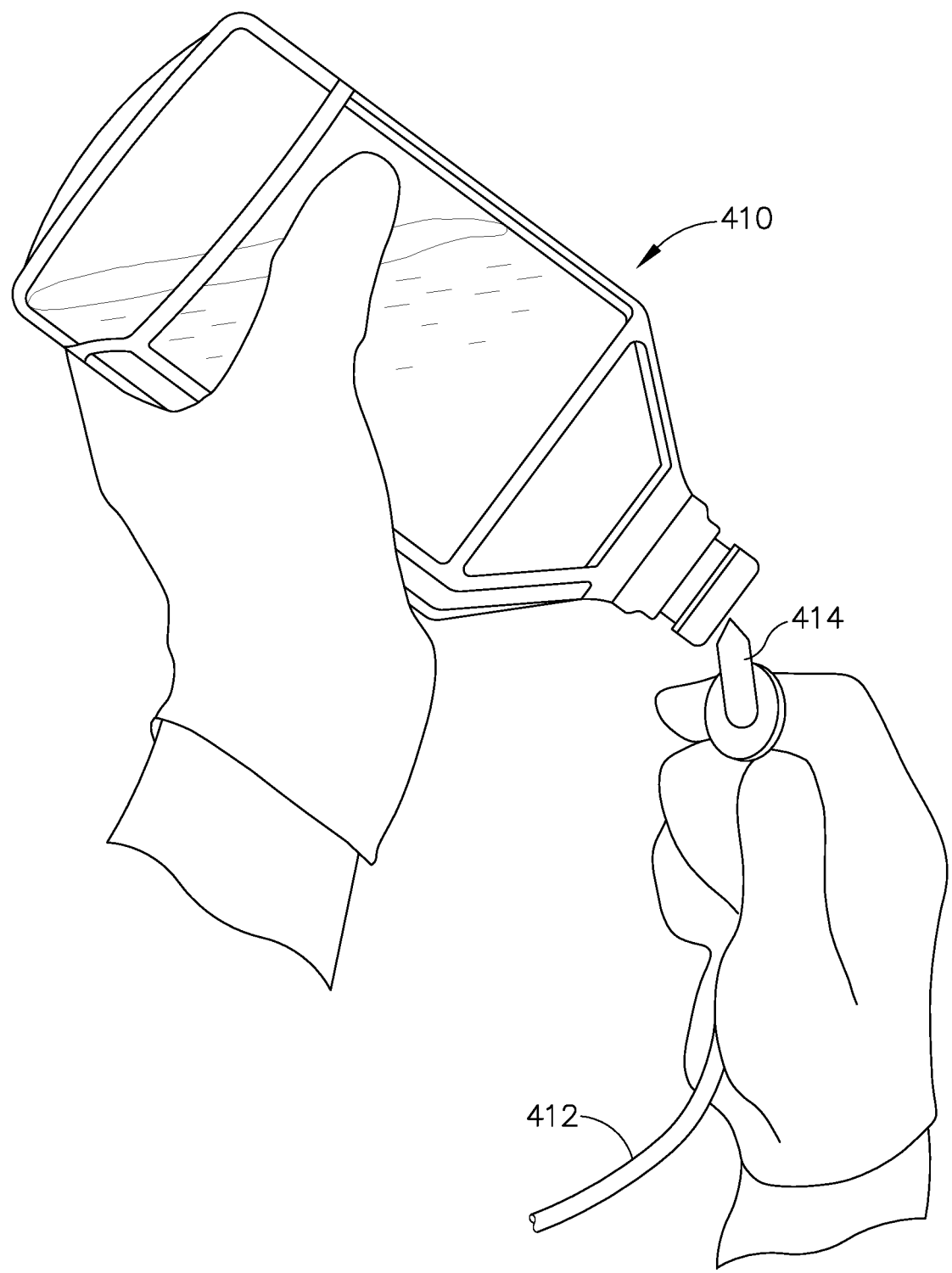
FIG. 9H depicts a perspective view of a spike from a first conduit of the syringe actuation cassette of FIG. 9G being inserted into a balanced salt solution bottle, at an eighth stage of the procedure of FIG. 9A.

Before or after seating syringe (570) in syringe actuation cassette (550), the operator inserts spike (414) of conduit (412) in bottle (410), as shown in FIG. 9H, thereby providing a path for communication of bleb fluid (340) in bottle (410) to syringe actuation cassette (550).

Figure 9I:
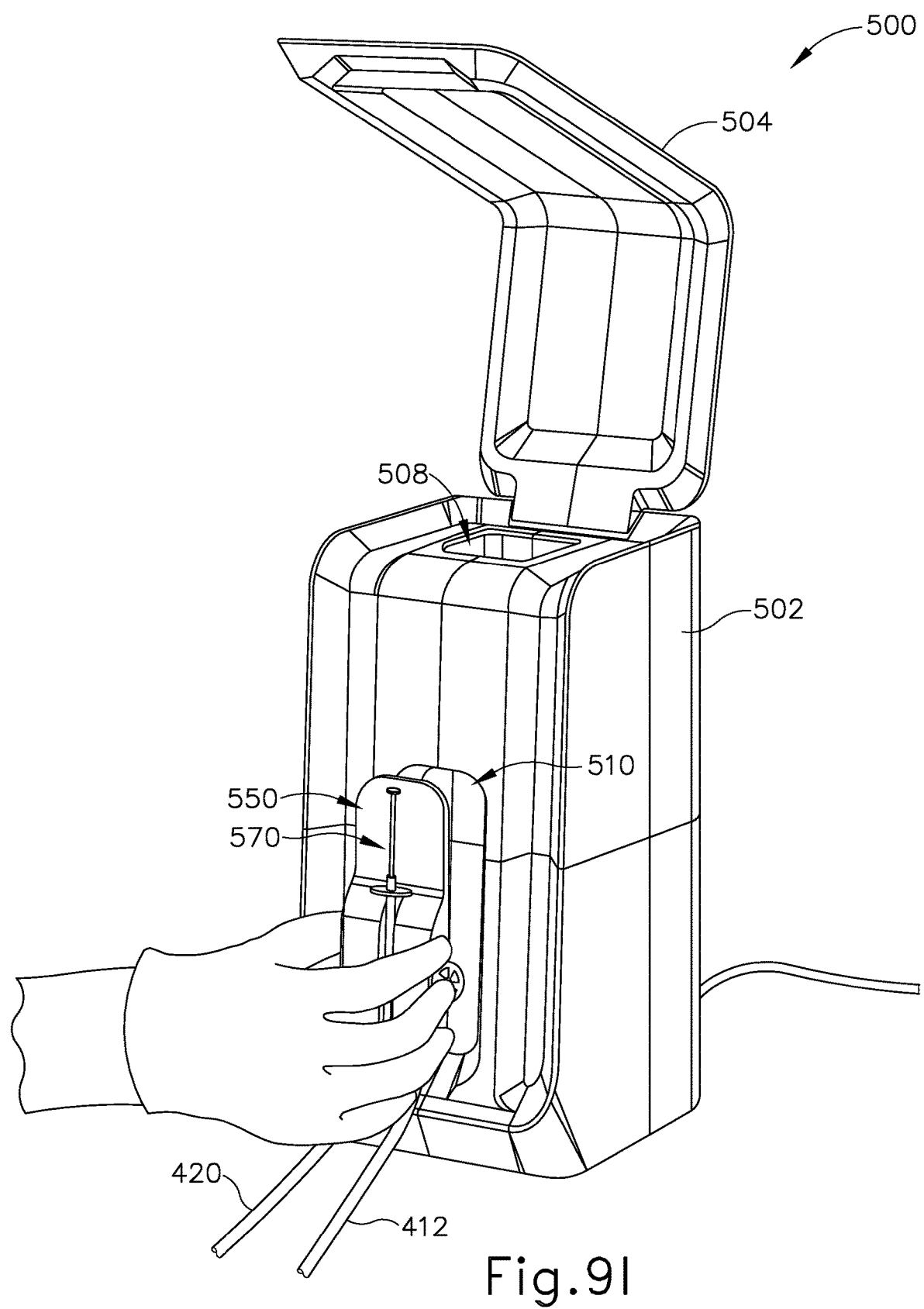
FIG. 9I depicts a perspective view of the syringe actuation cassette of FIG. 9G being inserted into the control module of FIG. 9A, with the cover in an open position, at a ninth stage of the procedure of FIG. 9A.
Figure 9J:
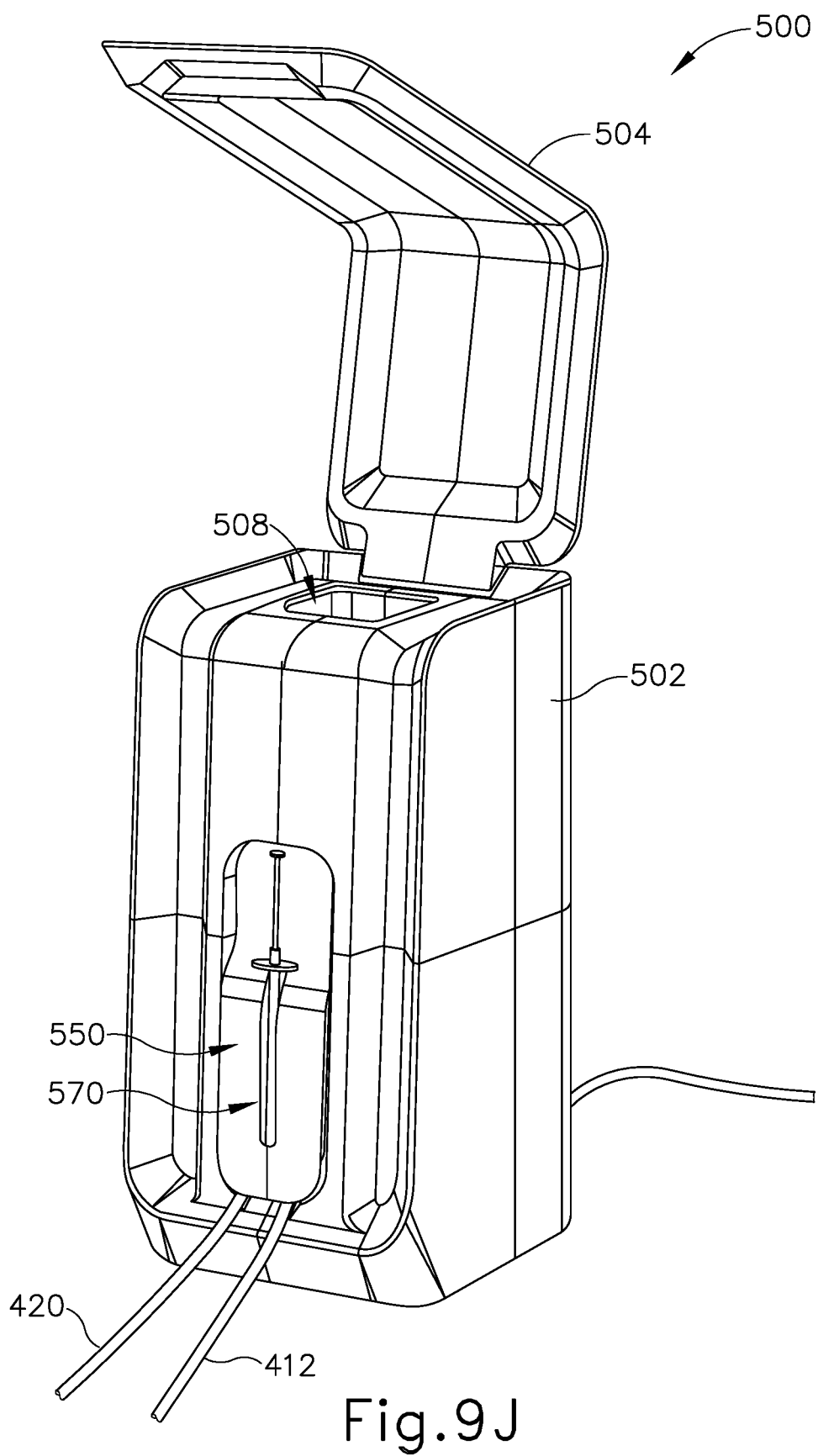
FIG. 9J depicts a perspective view of the syringe actuation cassette of FIG. 9G fully seated in the control module of FIG. 9A, with the cover in an open position, at a tenth stage of the procedure of FIG. 9A.

With syringe (570) and bottle (410) coupled with syringe actuation cassette (550), the operator positions syringe actuation cassette (550) in relation to cassette receptacle (510), as shown in FIG. 9I. The operator then fully seats syringe actuation cassette (550) in cassette receptacle (510), as shown in FIG. 9J. This couples cassette actuator (512) with complementary features of syringe actuation cassette (550) as noted above.

Figure 9K:
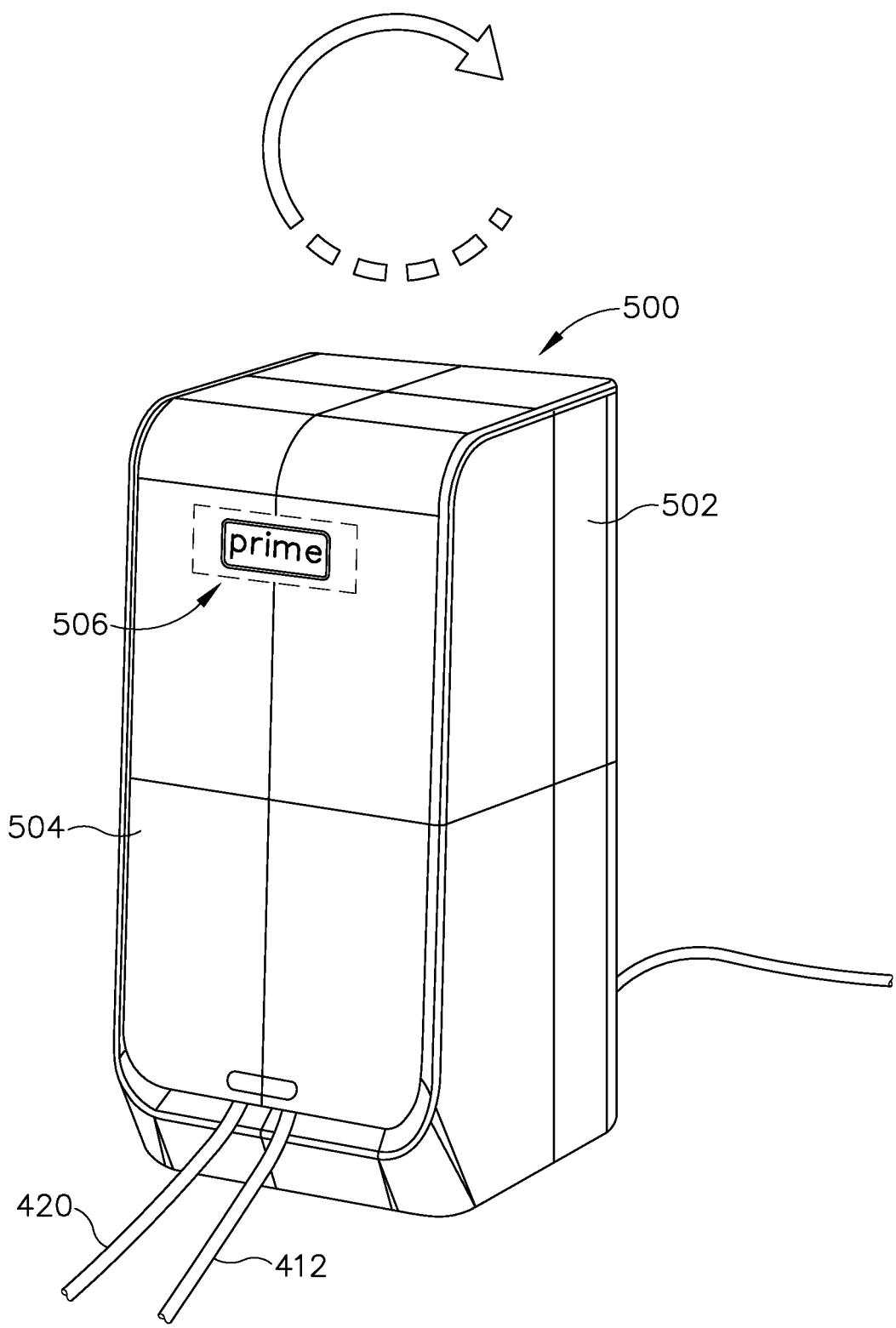
FIG. 9K depicts a perspective view of the control module of FIG. 9A, with the cover in a closed position, at an eleventh stage of the procedure of FIG. 9A.

Next, the operator closes cover (504) as shown in FIG. 9K, to begin a priming sequence. In some versions, priming is initiated automatically upon closure of cover (504). In some other versions, priming will not begin until the operator actuates some kind of user input feature after closing cover (504). In either case, cover (504) includes features that accommodate conduit (412) and tube set (420) without pinching off or otherwise impeding fluid flow through conduits (412, 422, 424). The priming sequence purges air from conduits (412, 422, 424), ensuring that the entire length of each conduit (412, 422, 424) is full of the corresponding fluid. In some instances, this priming sequence further includes priming a needle (708) and needle actuator (716) of injector assembly (700) with bleb fluid (340), in addition to priming first conduit (422) with bleb fluid (340). As therapeutic agent (341) is primed through second conduit (424), control module (500) may ensure that such priming is provided at a relatively slow flow rate in order to minimize stress on cells contained in therapeutic agent (341).

Figure 9L:
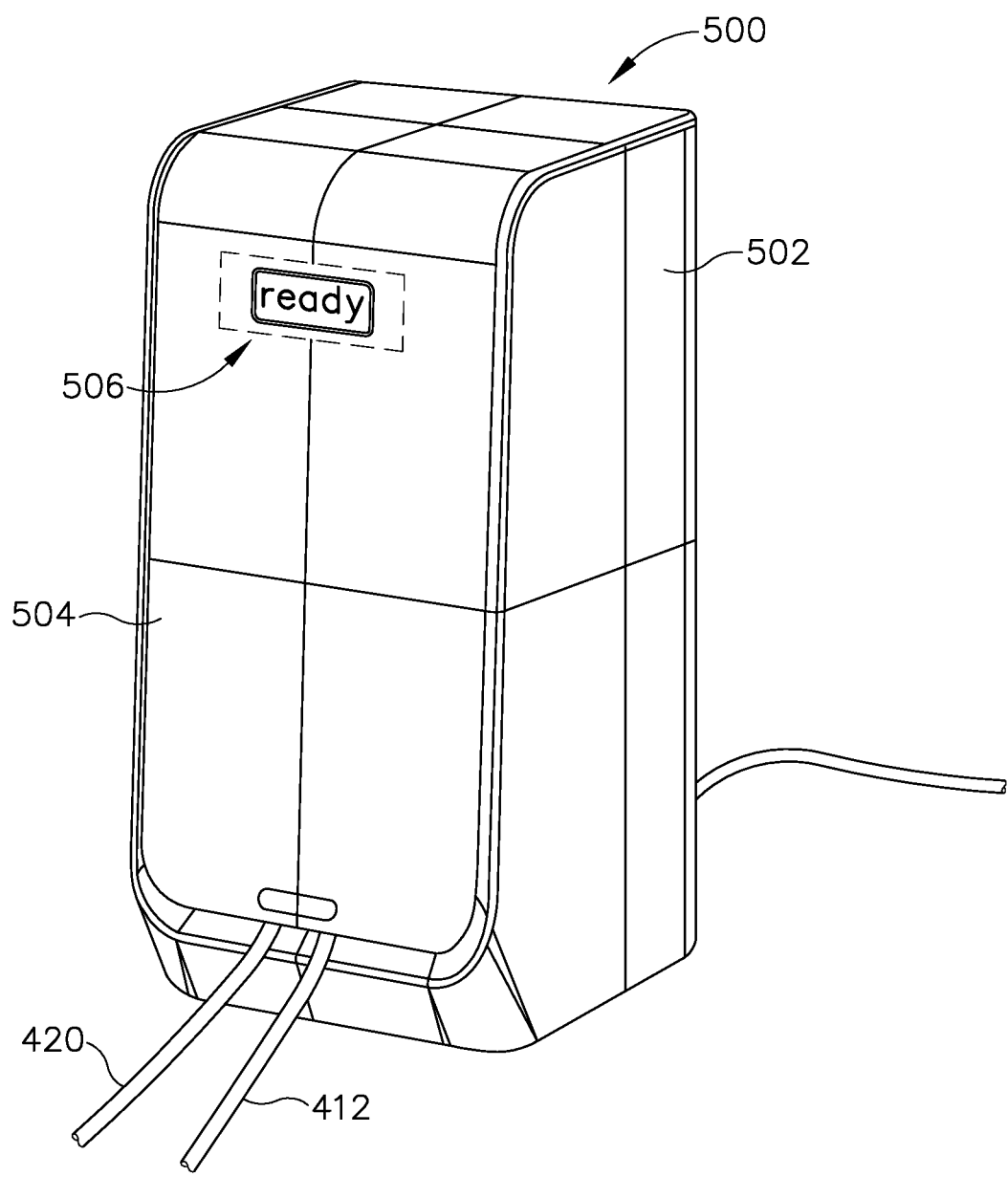
FIG. 9L depicts a perspective view of the control module of FIG. 9A, with the cover in a closed position, at a twelfth stage of the procedure of FIG. 9A.

During the priming sequence, display region (506) may display an indication to the operator that the priming sequence is underway. In addition, display region (506) may display the amount of time left remaining in the priming sequence. After the priming sequence is complete, display region (506) may display an indication to the operator that control module (500) is ready for use, as shown in FIG. 9L.

In some versions, control module (500) is operable to sense the presence of an occlusion in at least one conduit (412, 422, 424). Various suitable ways in which occlusion may be sensed will be apparent to those of ordinary skill in the art in view of the teachings herein. In the event that an occlusion is detected, control module (400) may automatically alert the operator via display region (506).

C. Exemplary Magnetic Pads

As noted above, system (400) of the present example includes a magnetic pad (460). Magnetic pad (460) may be adhered to drape (452) via a pressure sensitive adhesive. For instance, magnetic pad (460) may be provided with a peel-away cover positioned on the adhesive on the underside. The operator may then peel away the cover to reveal the adhesive, then press magnetic pad (460) against drape (452) to adhere magnetic pad (460) to drape. In use, magnetic pad (460) is located at a position on drape (452) over the patient's forehead. In the present example, magnetic pad (460) is flexible to some degree, such that magnetic pad (460) may at least partially conform to the curvature of the patient's forehead. By way of example only, magnetic pad (460) may be formed at least in part of silicone.

As also noted above, injector assembly (700) is placed on magnetic pad (460), and is removably secured thereto via magnetic attraction. This enables injector assembly (700) to be easily repositioned on magnetic pad (460) and removed from magnetic pad (460). As will be described in greater detail below, injector assembly (700) includes magnets (706) that provide magnetic attraction to magnetic pad (460). In some versions, magnetic pad (460) also includes an array of magnetic elements that provide magnetic attraction with magnets (706). In some other versions, magnetic pad (460) includes one or more ferrous elements (e.g., ferrous metal filings embedded in the pad material, a single thin metallic sheet embedded in the pad material, etc.) that provide magnetic attraction with magnets (706). Various suitable features and configurations that may be incorporated into magnetic pad (460) to provide magnetic attraction with magnets (706) will be apparent to those of ordinary skill in the art in view of the teachings herein. As yet another merely illustrative variation, other features may be used to provide removable coupling between pad (460) and injector assembly (700), including but not limited to hook-and-loop fasteners, adhesives, complementary press-fit bump texture and grip pattern, etc.

Figure 10:
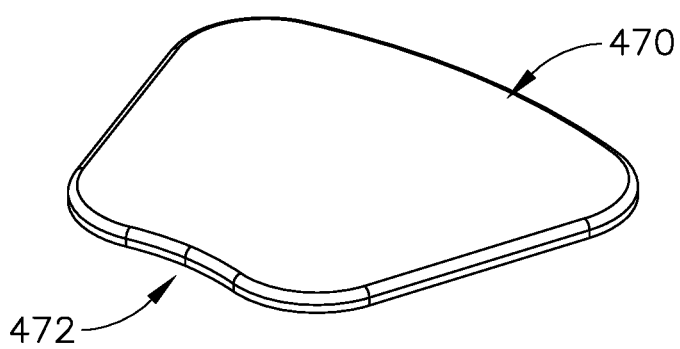
FIG. 10 depicts a perspective view of an exemplary magnetic pad that may be used as part of the system of FIG. 6.
Figure 11:
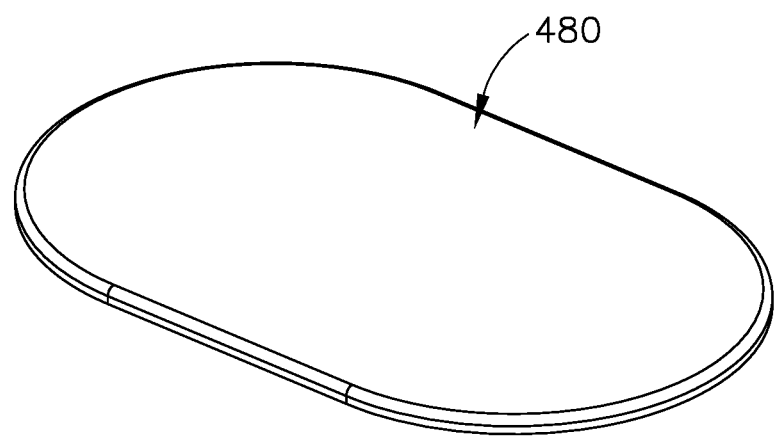
FIG. 11 depicts a perspective view of another exemplary magnetic pad that may be used as part of the system of FIG. 6.
Figure 12:
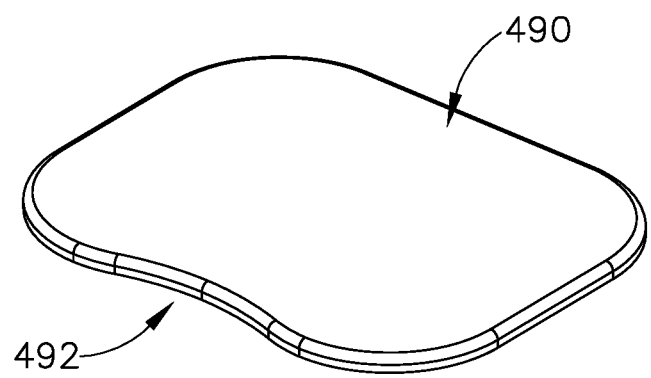
FIG. 12 depicts a perspective view of another exemplary magnetic pad that may be used as part of the system of FIG. 6.

FIGS. 10-12 show various alternative forms that magnetic pad (460) may take. In particular, FIG. 10 shows a magnetic pad (470) having a generally arcuate shape. This arcuate shape includes a concave region (472) that may be positioned near the patient's eye (301). FIG. 11 shows a magnetic pad (480) having an oval or flattened-ellipse shape. FIG. 12 shows a magnetic pad (490) having a generally rectangular shape with a concave side (492) that may be positioned near the patient's eye (301). Other suitable forms that a magnetic pad (460) may take will be apparent to those of ordinary skill in the art in view of the teachings herein.

D. Exemplary Injector Assembly with Remote Tethered Control

Figure 13:
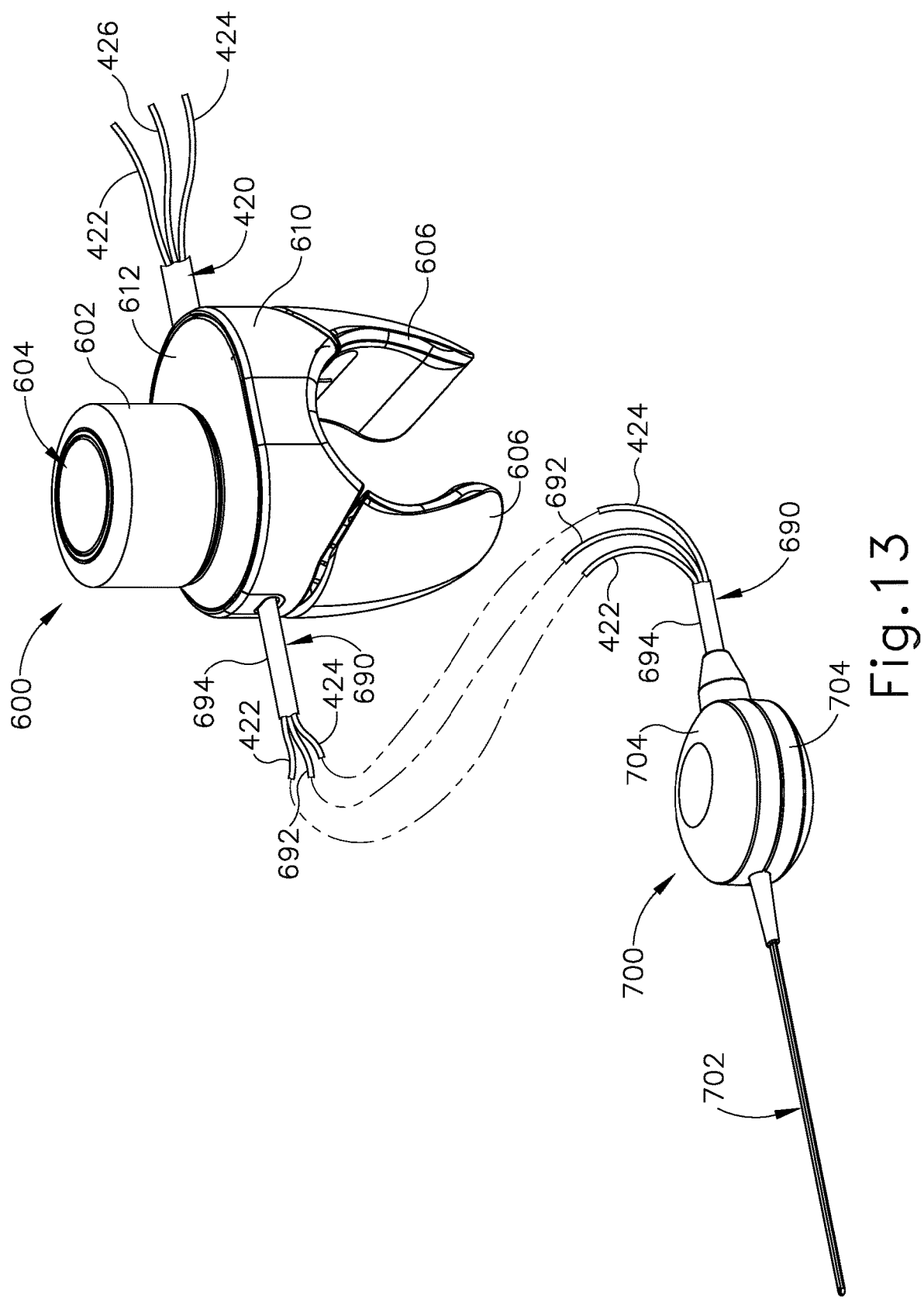
FIG. 13 depicts a perspective view of an exemplary injector assembly and an exemplary injector driver assembly of the system of FIG. 6.

FIG. 13 shows injector driver assembly (600) coupled with injector assembly (700) via tube and cable assembly (690). As shown in FIG. 13, conduits (422, 424) and electrical cable enter the proximal end of injector driver assembly (600) as part of tube set (420). Conduits (422, 424) pass through injector driver assembly (600), exiting the distal end of injector driver assembly (600) as part of tube and cable assembly (690). Conduits (422, 424) enter the proximal end of injector assembly (700) as part of tube and cable assembly (690). Tube and cable assembly (690) also includes a push-pull cable (692), which is operable to transfer longitudinal movement from injector driver assembly (600) to injector assembly (700) as will be described in greater detail below. Tube and cable assembly (690) also includes an outer sheath (694). Outer sheath (694) is configured to contain conduits (422, 424) and push-pull cable (692). Outer sheath (694) is also configured to serve as a longitudinal mechanical ground with respect to push-pull cable (692), such that push-pull cable (692) translates relative to outer sheath (694).

1 Exemplary Injector Assembly

FIGS. 14-18 show injector assembly (700) and components thereof in greater detail. As shown, injector assembly (700) of this example includes a cannula (702), a pair of housing halves (704), and a needle (708) slidably disposed in housing halves (704). Cannula (702) may be configured and operable just like cannula (50) described above; and needle (708) may be configured and operable just like needle (100) described above. A needle actuator (710) and magnets (706) are captured within housing halves (704). When injector assembly (700) is fully assembled, housing halves (704) are configured to hold magnets (706) in stationary positions; and to allow needle actuator (710) to translate distally and proximally within housing halves (704). In particular, as best seen in FIGS. 15A-15B, housing halves (704) include bosses (705) that are configured to guide and laterally support needle actuator (710) as needle actuator (710) translates between a proximal position (FIG. 15A) and a distal position (FIG. 15B).

Figure 14:
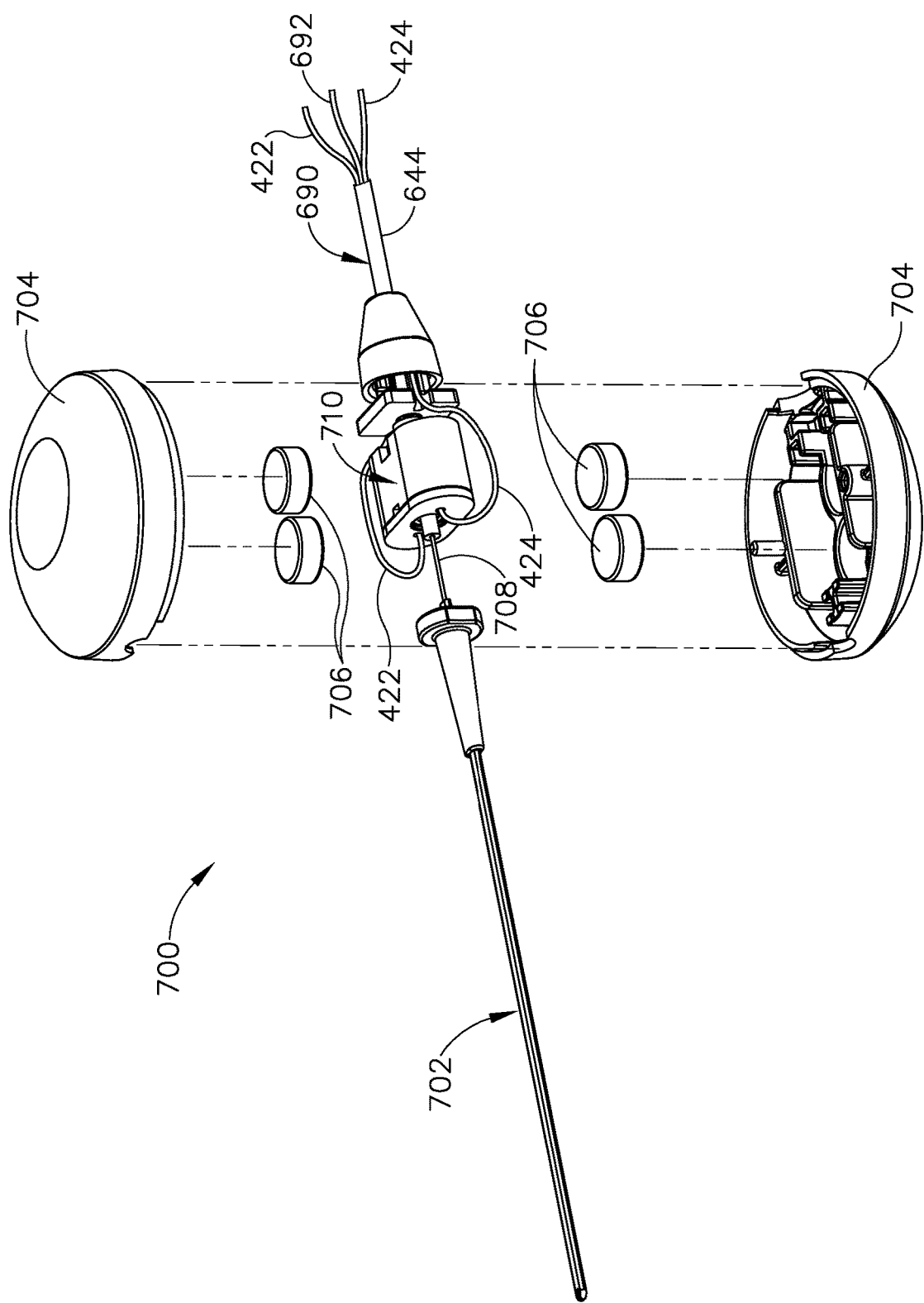
FIG. 14 depicts an exploded perspective view of the injector assembly of FIG. 13.
Figure 15A:
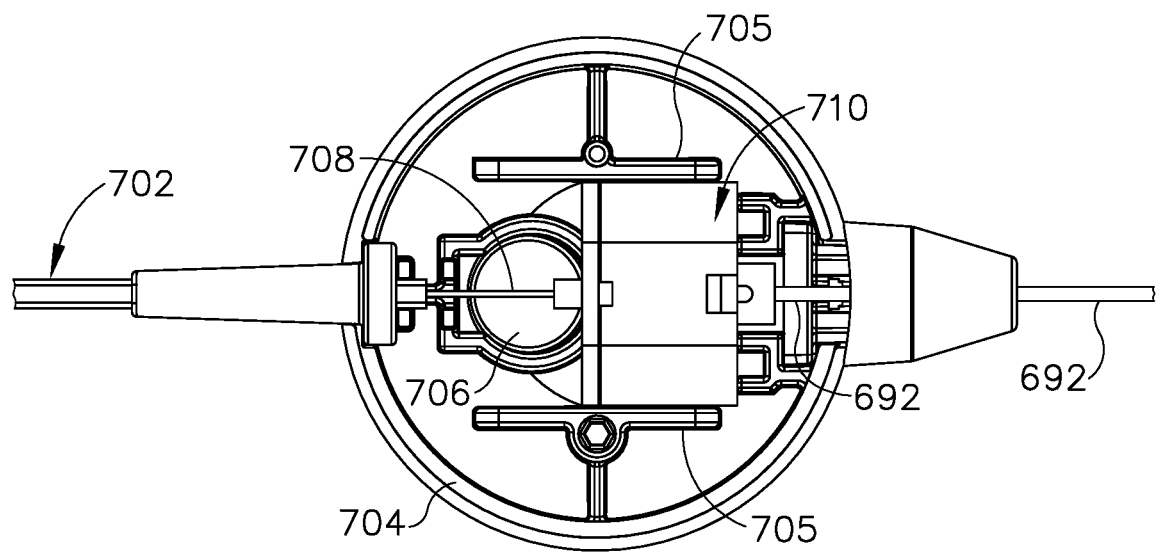
FIG. 15A depicts a top plan view of the injector assembly of FIG. 13, with a top cover removed, and with a needle actuator in a proximal position.
Figure 15B:
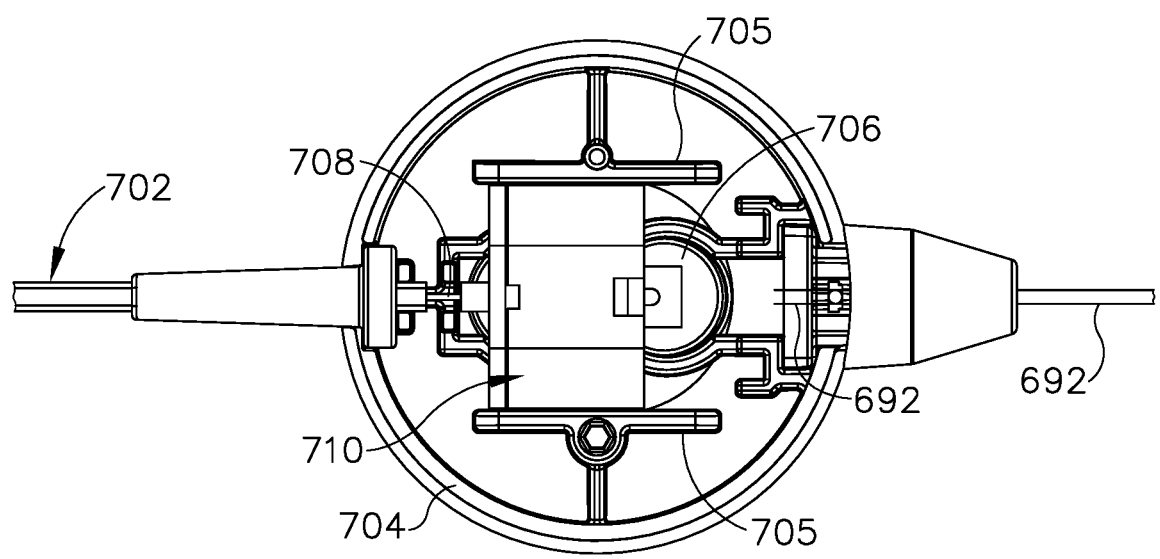
FIG. 15B depicts a top plan view of the injector assembly of FIG. 13, with the top cover removed, and with the needle actuator in a distal position.
Figure 16:
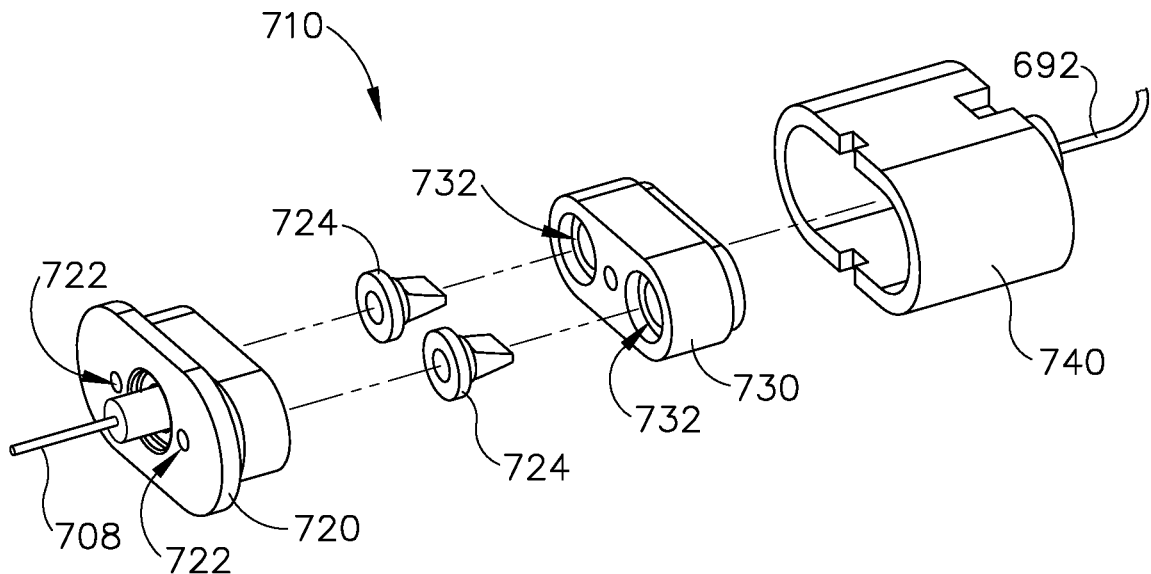
FIG. 16 depicts an exploded perspective view of the needle actuator of FIG. 15A.
Figure 17:
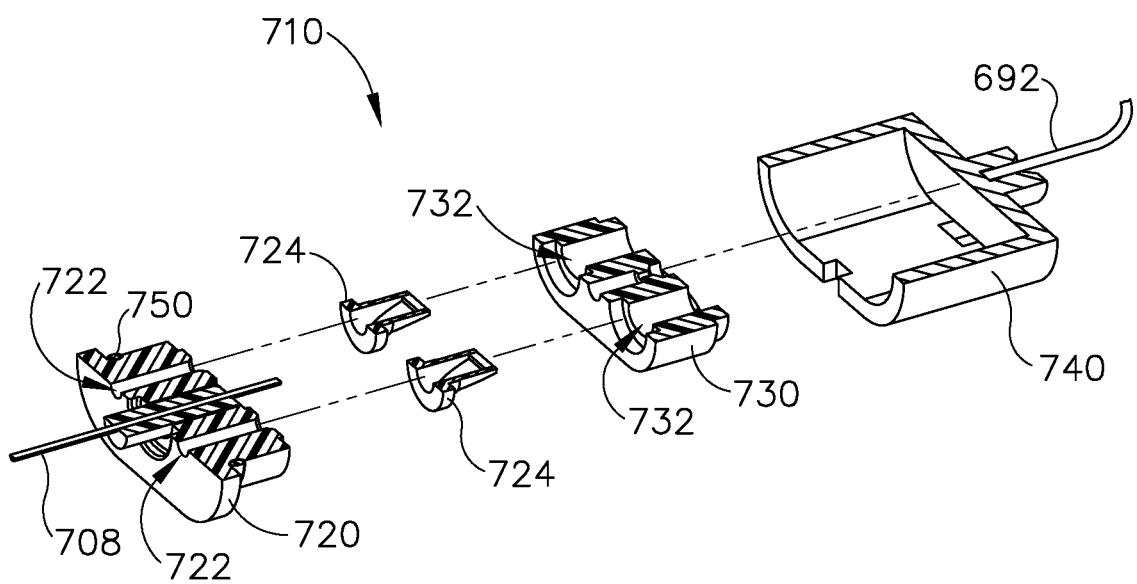
FIG. 17 depicts an exploded perspective cross-sectional view of the needle actuator of FIG. 15A.
Figure 18:
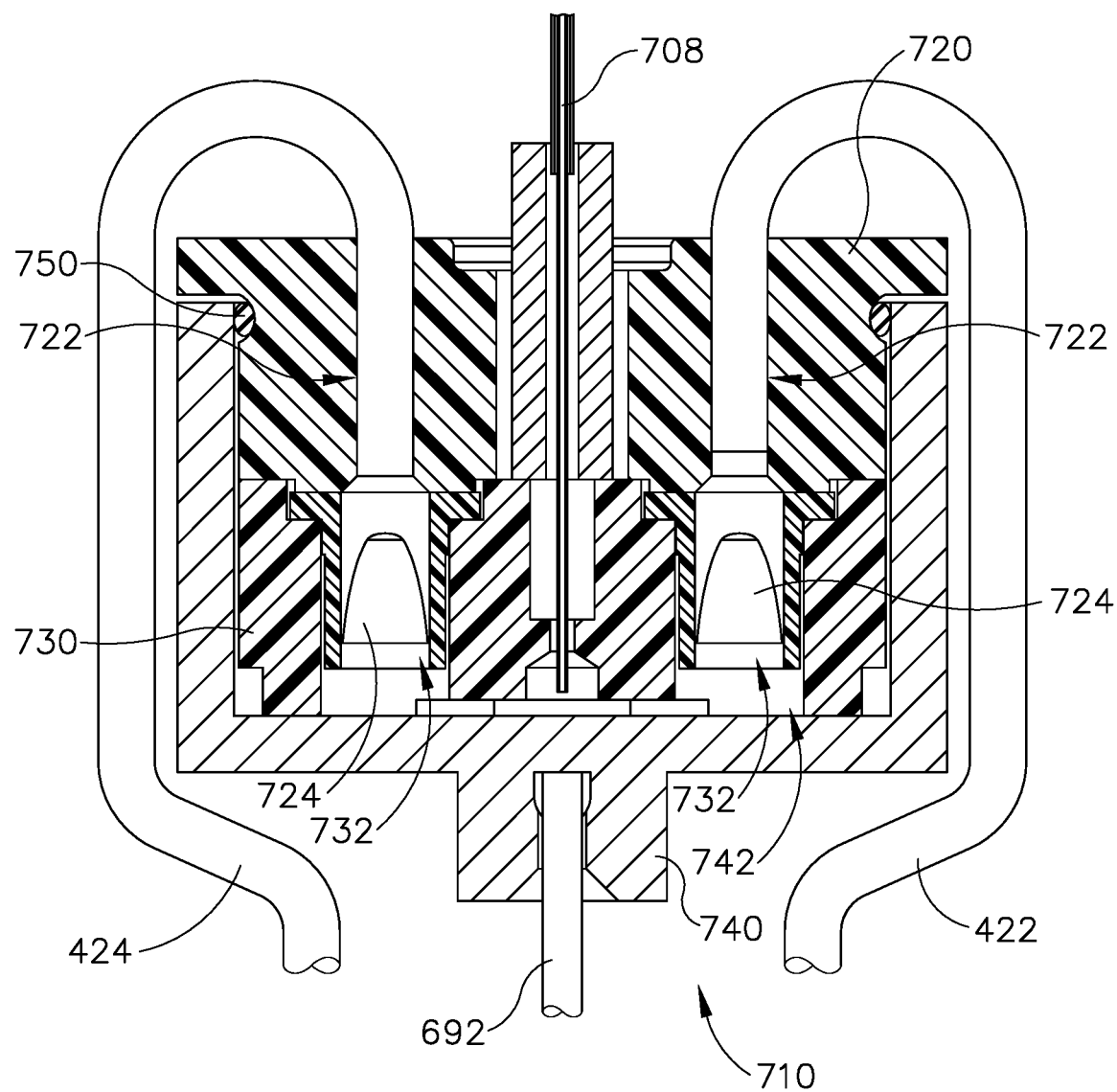
FIG. 18 depicts a top cross-sectional view of the needle actuator of FIG. 15A.

As best seen in FIGS. 16-17, needle actuator (710) comprises a proximal housing (740), an intermediate housing (730), and a distal housing (720). Housings (720, 730, 740) are all fixedly secured together to define a unitary construction. The distal end of push-pull cable (692) is fixedly secured to the proximal end of proximal housing (740). The proximal end of needle (708) is fixedly secured to distal housing (720). Distal housing (720) defines a pair of bores (722) that are laterally offset from needle (708). As shown in FIGS. 14 and 18, one bore (722) receives the distal end of conduit (422), while the other bore (722) receives the distal end of conduit (424). Conduits (422, 424) wrap around the outside of needle actuator (710) and turn back toward needle actuator (710) to insert distal ends of conduits (422, 424) into respective bores (722). Intermediate housing (730) also defines a pair of bores (732) that align with bores (722). Each bore (732) has a respective duckbill valve (724) seated therein.

As best seen in FIG. 18, needle actuator (710) defines a chamber (742). The proximal end of needle (708) is located in chamber (742), such that needle (708) is in fluid communication with chamber (742). Bores (732) are also in fluid communication with chamber (742). Needle actuator (710) thus defines a fluid manifold. Duckbill valves (724) are configured to enable fluid to be communicated from conduits (422, 424) into chamber (742); while preventing fluid from being communicated from chamber (742) into conduits (422, 424). Thus, when bleb fluid (340) is communicated through conduit (422), bleb fluid (340) will exit through needle (708) and will not backflow through conduit (424). Similarly, when therapeutic agent (341) is communicated through conduit (424), therapeutic agent (341) will exit through needle (708) and will not backflow through conduit (422). As also shown in FIG. 18, an o-ring (750) is captured between distal housing (720) and proximal housing (740), and thereby provides a seal preventing fluid from escaping chamber (742) via the interface between distal housing (720) and proximal housing (740).

2. Exemplary Injector Driver Assembly

FIGS. 19-27B show injector driver assembly (600) and components thereof in greater detail. While conduits (422, 424) are omitted from FIGS. 19-27B, it should be understood that conduits (422, 424) pass through injector driver assembly (600) as noted above. As shown, injector driver assembly (600) of the present example comprises a knob (602), a pushbutton (604), a body (610), and an upper rocker plate (612). A pair of arms (606) are pivotably coupled to body (610) and are operable to secure injector driver assembly (600) to a wrist rest (456) as noted above. Injector driver assembly (600) may include one or more resilient member (e.g., torsion springs, leaf springs, etc.) to resiliently bias arms (606) toward each other, to thereby urge arms (606) to grasp wrist rest (456).

Figure 19:
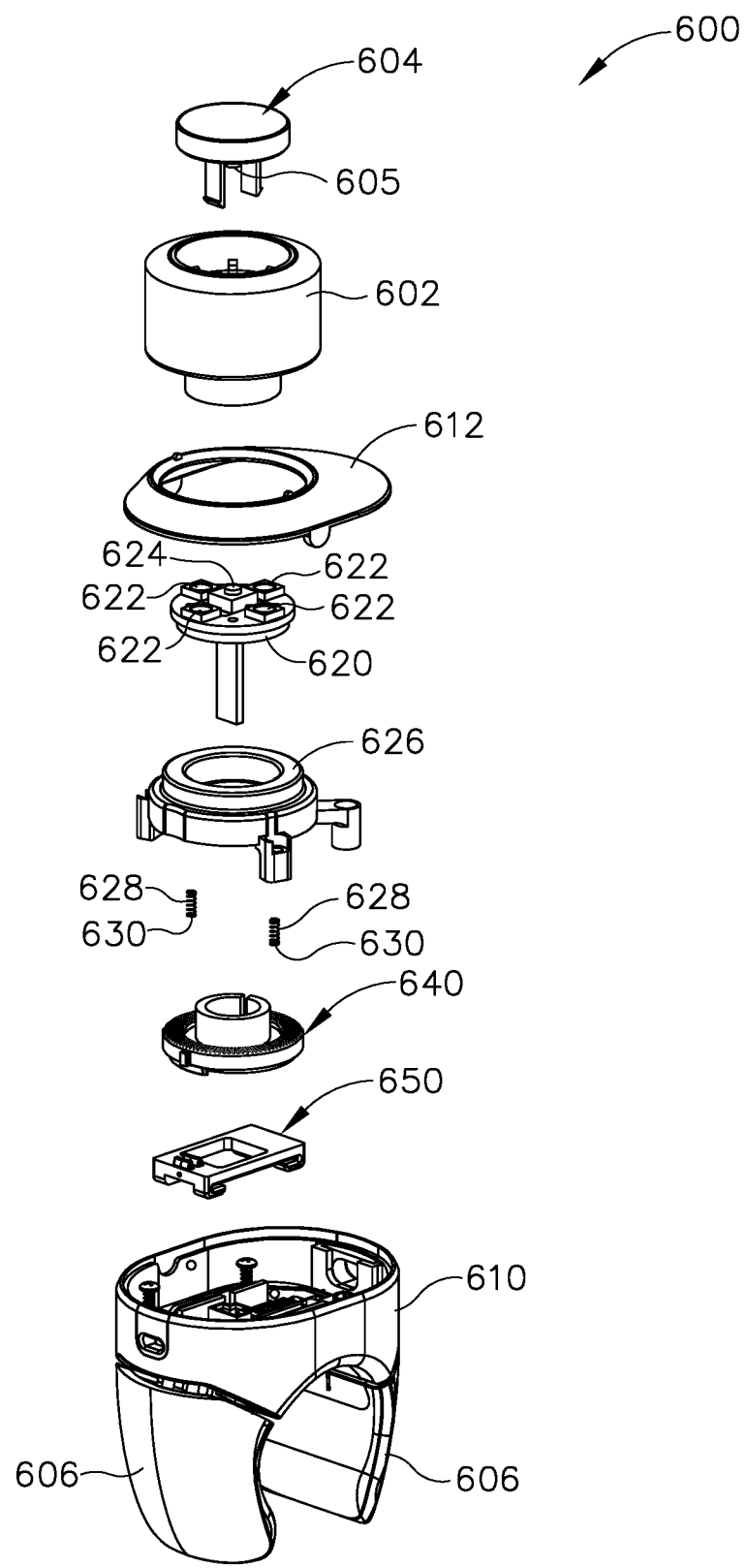
FIG. 19 depicts an exploded perspective view of the injector driver assembly of FIG. 13.

Knob (402), rocker pushbutton (604), plate (612), and body (610) are configured to cooperate to house several internal components within injector driver assembly (600). As shown in FIG. 19, these internal components include an array of RGB programmable LEDs (622) and a first tactile switch (624), all of which are mounted to a disc-shaped platform (620). The internal components further include an annular frame (626), a rotary cam member (640), a cam follower (650), a set of coil springs (628), and a set of ball bearings (630). Knob (402), pushbutton (604), and cam member (640) are coupled together such that knob (402), pushbutton (604), and cam member (640) are rotatable relative to the other components of injector driver assembly (600).

Pushbutton (604) is configured to reciprocate vertically within knob (402). A stud (605) (FIG. 19) projects downwardly from the underside of stud (605) and is configured to actuate tactile switch (624) when pushbutton (604) is pressed downwardly relative to knob (402). Tactile switch (624) is in communication with control module (500) via electric cable (426). In the present example, control module (500) is configured to initiate dispensation of therapeutic agent (341) through conduit (422) in response to tactile switch (624) being actuated via pushbutton (604). In some other versions, control module (500) is configured to initiate dispensation of bleb fluid (340) through conduit (424) in response to tactile switch (624) being actuated via pushbutton (604).

LEDs (622) are configured to selectively illuminate. Knob (402) and pushbutton (604) are configured to enable viewing of light emitted by LEDs (622). LEDs (622) may illuminate differently based on the particular state of system (400). For instance, LEDs (622) may illuminate in red when system (400) is not ready for actuation of pushbutton (604); and in green when system (400) is ready for actuation of pushbutton (604). As another merely illustrative example, LEDs (622) may illuminate in green when needle (708) is in a fully proximal, retracted position; in yellow when needle (708) is in an intermediate position but not yet extending from cannula (702); and in violet when needle (708) is in a distally advanced position where needle (708) protrudes from cannula (702). Other suitable ways in which LEDs (622) may be used will be apparent to those of ordinary skill in the art in view of the teachings herein.

Figure 20:
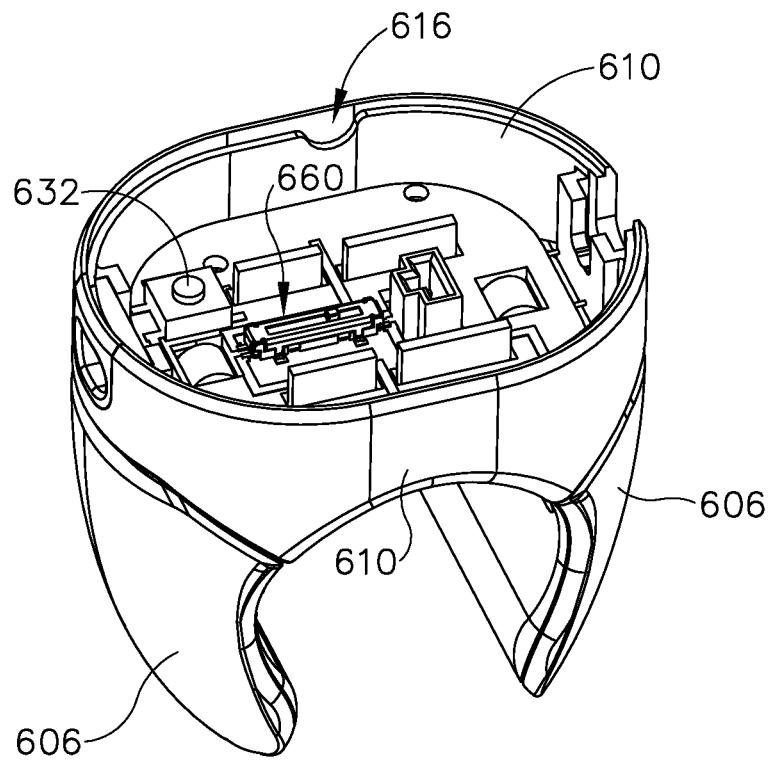
FIG. 20 depicts a perspective view of a bottom portion of the injector driver assembly of FIG. 13.

As shown in FIG. 20, another tactile switch (632) is located within body (610). Tactile switch (632) is configured to be actuated by upper rocker plate (612), as will be described in greater detail below. A linear sensor (660) is also located within body (610). Linear sensor (660) is configured to be actuated by cam follower (650), as will be described in greater detail below. Tactile switch (632) and linear sensor (660) are both in communication with control module (500) via electric cable (426).

Figure 21:
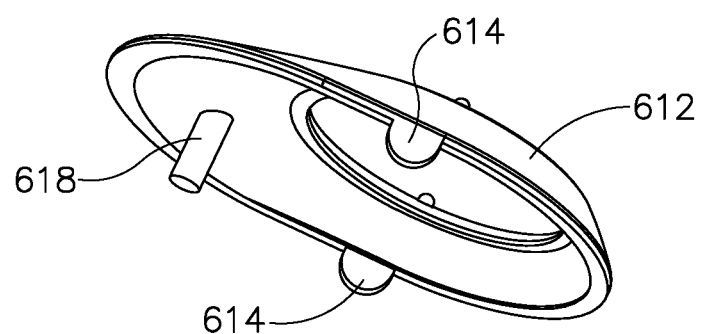
FIG. 21 depicts a perspective view of an upper rocker plate of the injector driver assembly of FIG. 13.

FIG. 21 shows rocker plate (612) in greater detail. As shown, rocker plate (612) includes a pair of downwardly projecting tabs (614) and a downwardly projecting stud (618). Tabs (614) are rounded and are configured to fit in complementary recesses (616) (FIG. 20) of body (610). This configuration of tabs (614) and recesses (616) allows rocker plate (612) to be rocked in such a way to enable stud (618) to selectively actuate tactile switch (632). In the present example, control module (500) is configured to initiate dispensation of bleb fluid (340) through conduit (422) in response to tactile switch (632) being actuated via rocker plate (612). In some other versions, control module (500) is configured to initiate dispensation of therapeutic agent (341) through conduit (424) in response to tactile switch (632) being actuated via rocker plate (612).

Figure 22:
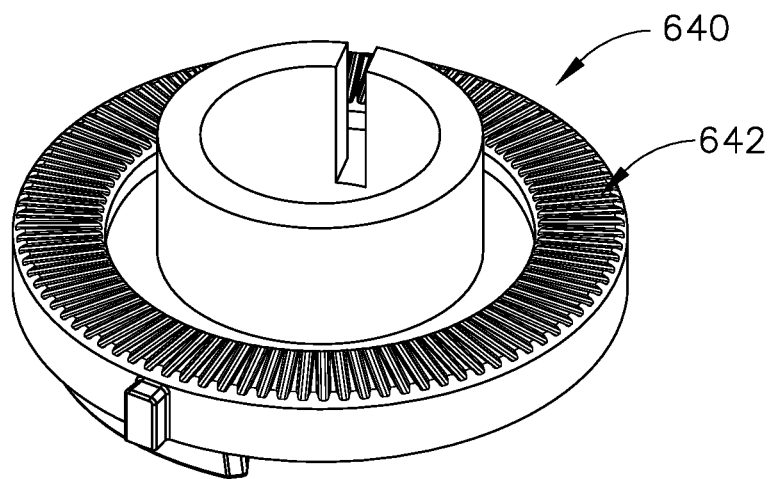
FIG. 22 depicts a perspective view of a rotary cam member of the injector driver assembly of FIG. 13.
Figure 23:
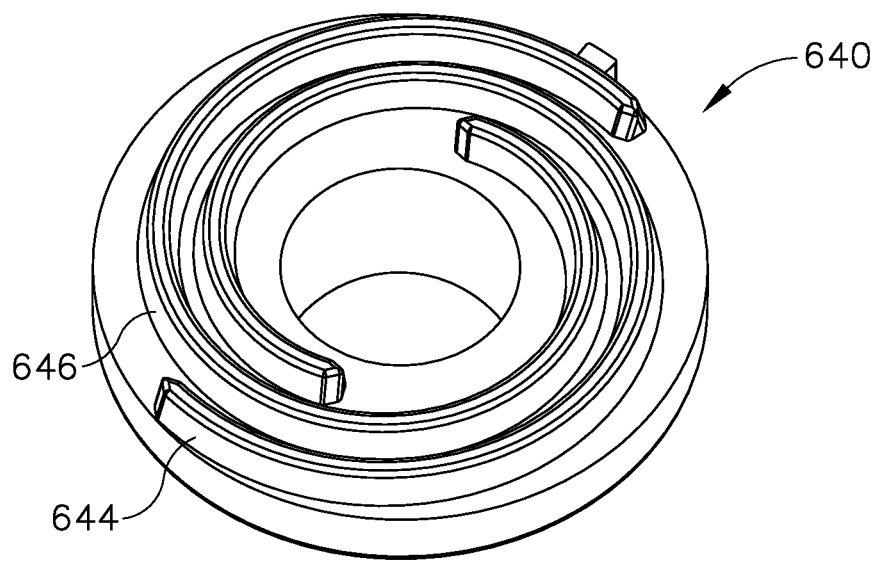
FIG. 23 depicts another perspective view of the rotary cam member of FIG. 22.

FIGS. 22-23 show rotary cam (640) in greater detail. As shown in FIG. 22, the upper side of rotary cam (640) includes an annular array of teeth (642) arranged in a starburst pattern. Teeth (642) are configured to engage ball bearings (630). An upper end of each coil spring (628) bears against the underside of annular frame (626), which serves as a mechanical ground. The lower end of each spring contacts a respective ball bearing (630) and thereby resiliently urges ball bearings (630) into engagement with teeth (642). The relationship between ball bearings (630) and teeth (642) provides enough resistance to rotation of knob (602) and rotary cam (640) to prevent inadvertent rotation of knob (602) and rotary cam (640); yet still permits intentional rotation of knob (602) and rotary cam (640). The resistance provided by ball bearings (630) and teeth (642) may also enable the operator to achieve a greater degree of precision in rotating knob (602) than the operator might otherwise achieve in the absence of such resistance. Other suitable kinds of structures that may be used instead of coil springs (628), ball bearings (630), and teeth (642) will be apparent to those of ordinary skill in the art in view of the teachings herein.

As shown in FIG. 23, the underside of rotary cam (640) includes a first spiral cam feature (644) and a second spiral cam feature (646). While spiral cam features (644, 646) are generally positioned about the radial center of rotary cam (640), spiral cam features (644, 646) are offset from the radial center of rotary cam (640) and from each other.

Figure 24:
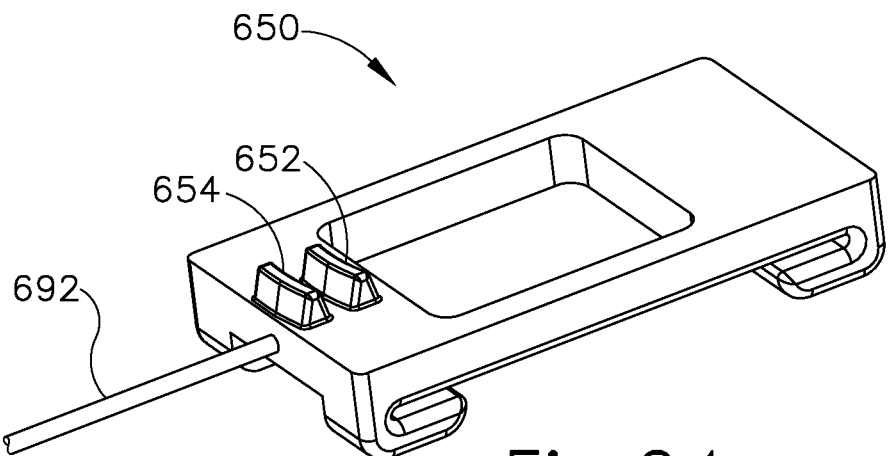
FIG. 24 depicts a perspective view of a cam follower of the injector driver assembly of FIG. 13.
Figure 25:
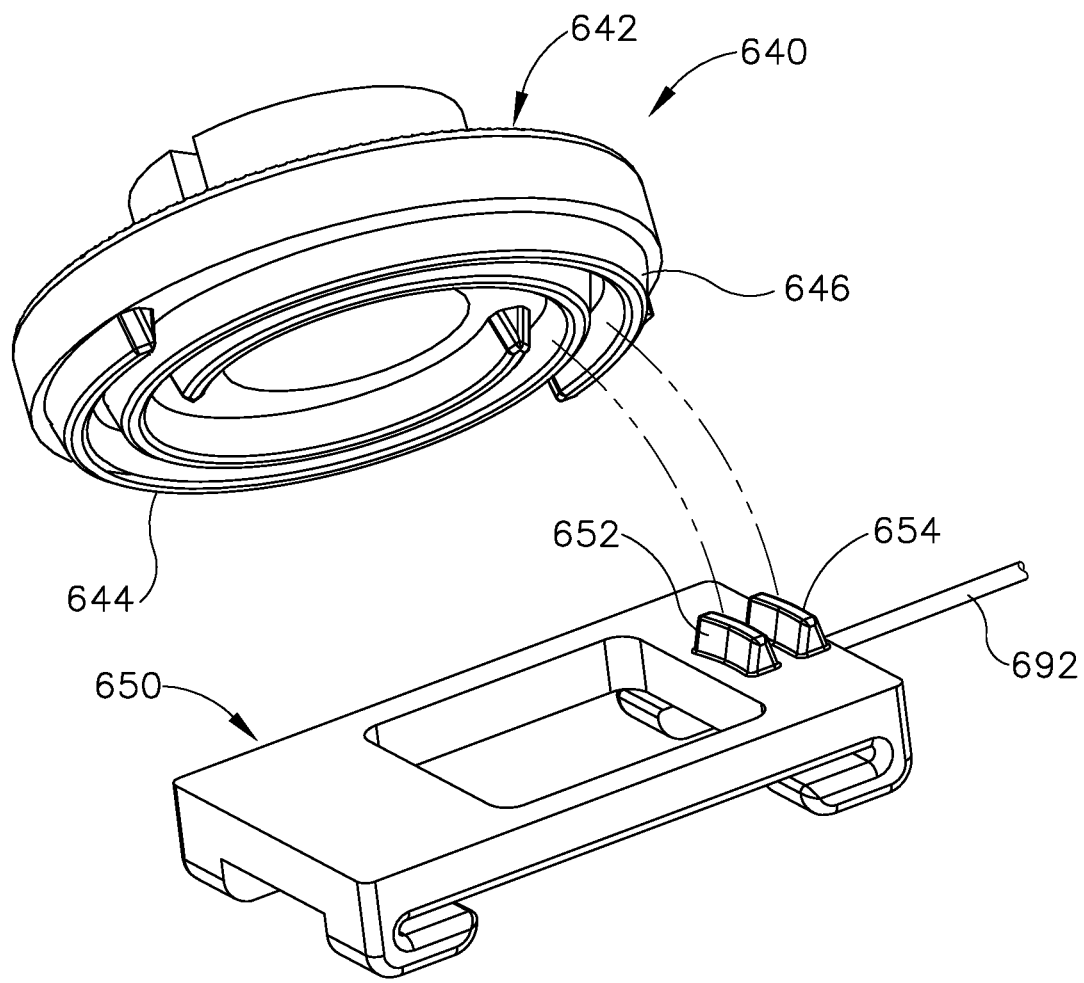
FIG. 25 depicts an exploded perspective view of the rotary cam member of FIG. 22 and the cam follower of FIG. 24.

As shown in FIG. 24, cam follower (650) of the present example includes a first upwardly projecting cam fin (652) and a second upwardly projecting cam fin (654). The proximal end of push-pull cable (692) is fixedly secured to cam follower (650). Cam fins (652, 654) are each contoured to complement the contours of spiral cam features (644, 646). As shown in FIG. 25, cam fin (652) is configured to fit in a first space between spiral cam features (644, 646); and cam fin (654) is configured to fit in a second space between spiral cam features (644, 646).

Figure 26A:
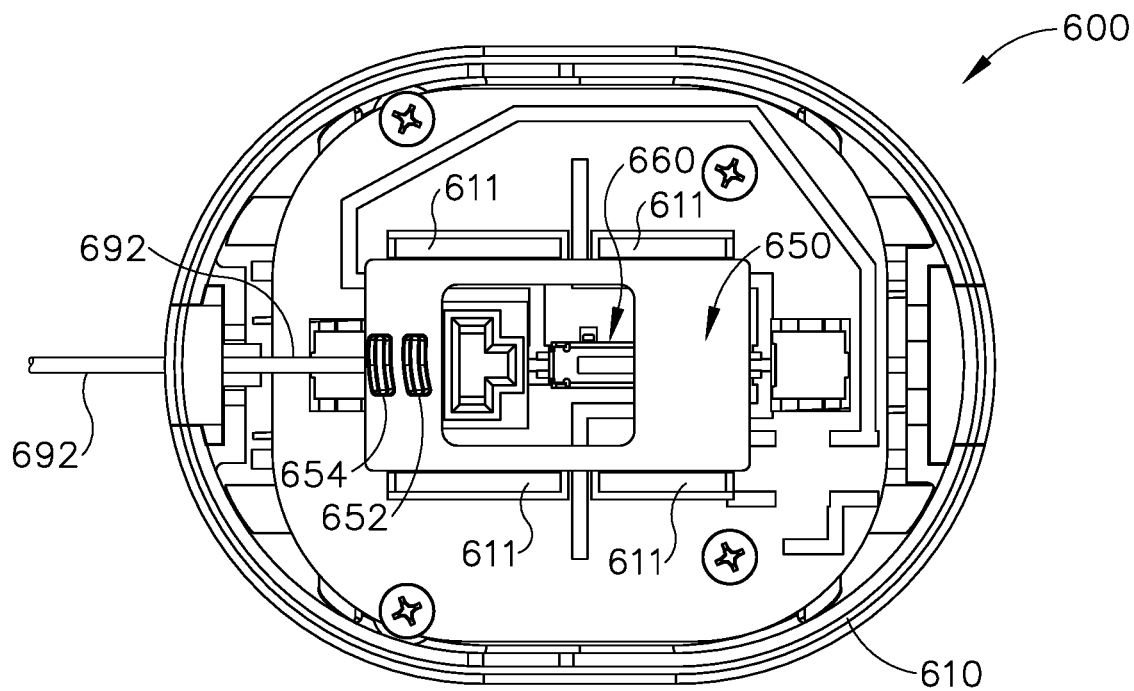
FIG. 26A depicts a top plan view of the injector driver assembly of FIG. 13, with an upper portion removed, and with the cam follower of FIG. 24 in a proximal position.
Figure 26B:
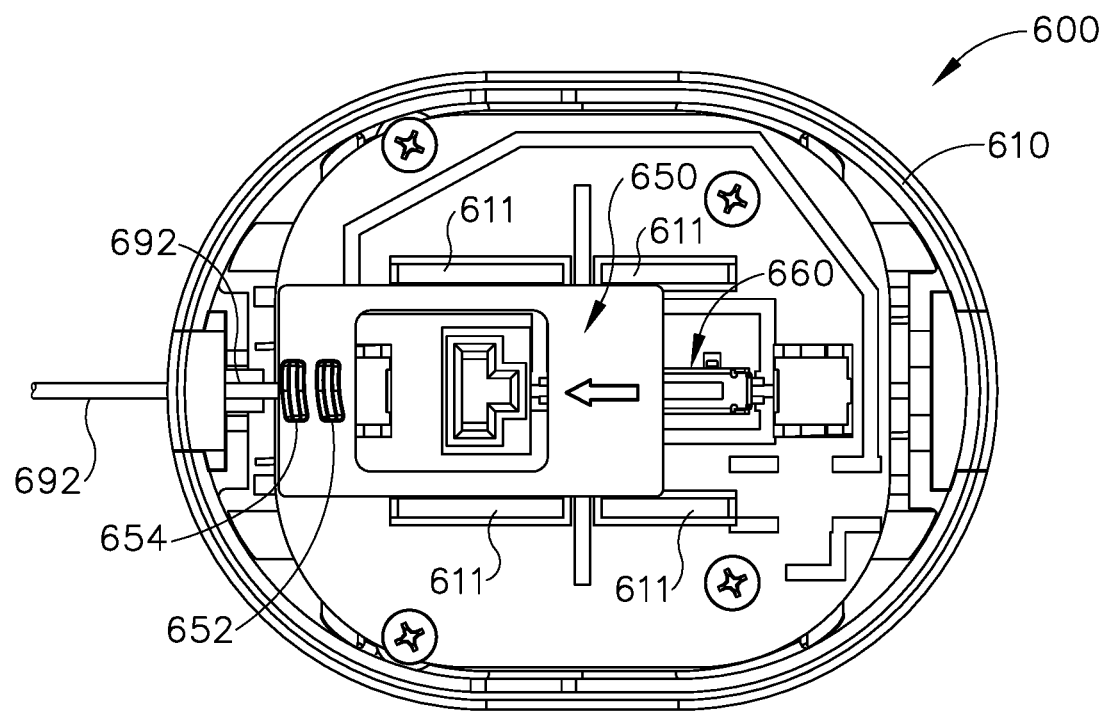
FIG. 26B depicts a top plan view of the injector driver assembly of FIG. 13, with an upper portion removed, and with the cam follower of FIG. 24 in a distal position.
Figure 27A:
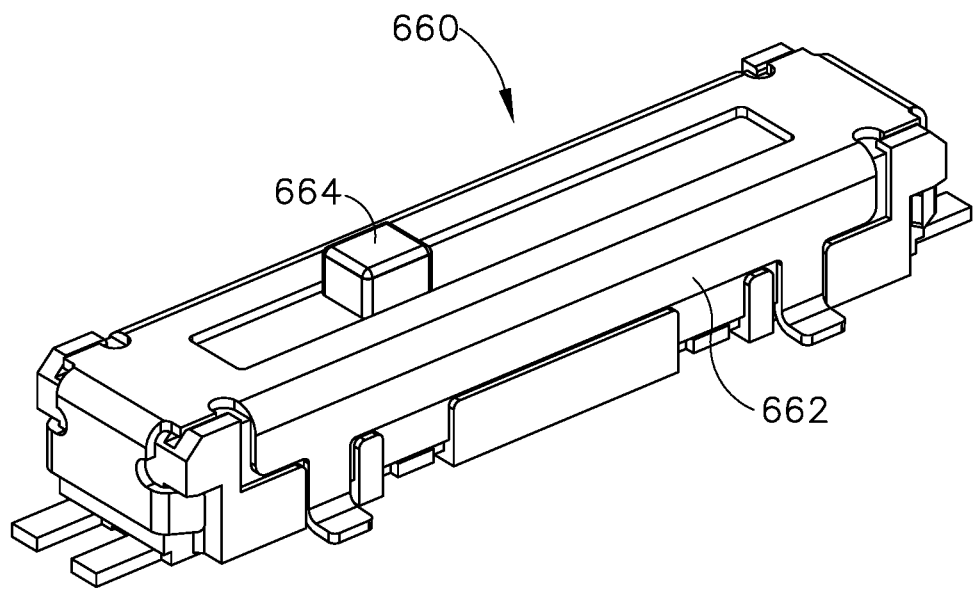
FIG. 27A depicts a perspective view of an exemplary linear sensor of the injector driver assembly of FIG. 13, with a slider of the sensor in a proximal position.
Figure 27B:
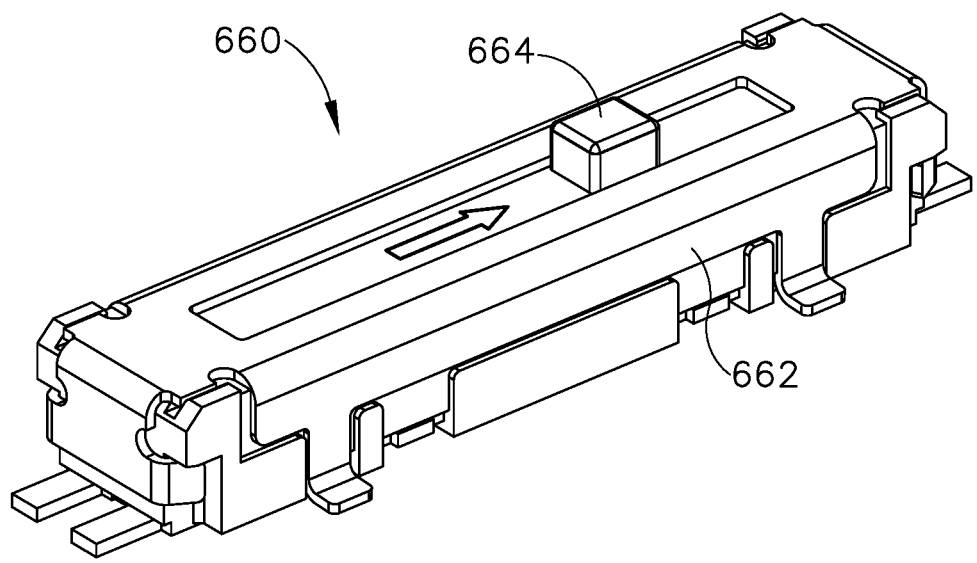
FIG. 27B depicts a perspective view of the linear sensor of FIG. 27A, with the slider of the sensor in a distal position.

Due to the engagement between cam fins (652, 654) and spiral cam features (644, 646), rotation of rotary cam (640) will cause cam follower (650) to translate longitudinally along the longitudinal axis of push-pull cable (692). Such translation is shown in FIGS. 26A-26B. As shown in FIGS. 26A-26B, cam follower (650) is captured between a set of bosses (611), which are unitary features of body (610). Bosses (611) are configured to guide and laterally support cam follower (650) as cam follower (650) translates between a proximal position (FIG. 26A) and a distal position (FIG. 26B). As noted above, push-pull cable (692) is fixedly secured to cam follower (650). Push-pull cable (692) is also fixedly secured to needle actuator (710), which is further fixedly secured to needle (708). It should therefore be understood that needle (708) will translate distally and proximally relative to cannula (702) in response to rotation of knob (602) relative to body (610).

Rotary cam (640) and cam follower (650) are mere examples of features that may be used to drive push-pull cable (692) longitudinally. By way of example only, an alternative drive assembly may include a pull-pull cable with a reversing pulley wheel (e.g., inside injector assembly (700)). By way of further example only, an alternative drive assembly may include an electrical line in tube and cable assembly (690); and a micromotor inside injector assembly (700). By way of further example only, an alternative drive assembly may include an electrical line in tube and cable assembly (690); and a nano-muscle nitinol wire inside injector assembly (700). By way of further example only, an alternative drive assembly may include a fluid drive line in tube and cable assembly (690); and a piston-cylinder assembly in injector assembly (700) to provide a hydraulic drive assembly, with spring return.

The underside of cam follower (650) is secured to a slider (664) of linear sensor (660). Slider (664) is configured to translate longitudinally relative to a body (662) of linear sensor (660). Since cam follower (650) is secured to slider (664), slider (664) will be in a proximal position (FIG. 27A) when cam follower (650) is in a proximal position (FIG. 26A); and slider (664) will be in a distal position (FIG. 27B) when cam follower (650) is in a distal position (FIG. 26B). Linear sensor (660) is configured to generate a varying data value based on the longitudinal position of slider (664) along body (662). By way of example only, linear sensor (660) may comprise a linear potentiometer that generates a varying resistance value based on the longitudinal position of slider (664) along body (662). Thus, the resistance value generated through linear sensor (660) will be indicative of the longitudinal position of needle (708) relative to cannula (702). By way of further example only, linear sensor (660) may comprise a sensor that senses rotation of knob (602), an optical sensor, or a sensor located in injector assembly (700) to directly monitor movement of needle actuator (710). Various other suitable ways in which movement of needle (708) may be sensed will be apparent to those of ordinary skill in the art in view of the teachings hereinein.

Since linear sensor (660) is in communication with control module (500), control module (500) may control the delivery of bleb fluid (340) and/or therapeutic agent (341) via conduits (422, 424) based on the longitudinal position of needle (708) relative to cannula (702) as sensed by linear sensor (660). In the present example, whenever linear sensor (660) detects distal advancement of needle (708), the corresponding signal sent to control module (500) will automatically trigger delivery of bleb fluid (340). This ensures that bleb fluid (340) will flow out through the distal tip of needle (708) any time needle (708) is advanced, on a consistent basis. By ensuring such bleb fluid flow (340) on a consistent basis, system (400) may minimize the risk of accentual perforation of the retina (308).

In some versions, control module (500) is programmed such that bleb fluid (340) is automatically delivered at a predetermined rate, based on advancement of needle (708) as sensed by linear sensor (660). Even in instances where bleb fluid (340) delivery is automated, control module (500) may still be responsive to actuation of tactile switch (632) to deliver additional bleb fluid (340) at a predetermined rate, independent of the longitudinal position of needle (708). It should also be understood that the delivery of therapeutic agent (341) may also be provided by control module (500) at a predetermined rate, to deliver a predetermined volume, in response to actuation of tactile switch (624). Moreover, the delivery of therapeutic agent (341) may be fully automated as soon as the operator actuates tactile switch (624) via pushbutton (604). In other words, the operator may not be able to selectively stop (and perhaps re-start) the delivery of therapeutic agent (341) once the operator has actuated tactile switch (624). Thus, the duration at which pushbutton (604) is depressed, or the repeated press and release of pushbutton, etc., may have no effect on the delivery of therapeutic agent (341) once the operator has actuated tactile switch (624). Other examples of ways in which delivery of bleb fluid (340) and/or therapeutic agent (341) may be automatically provided based on the sensed position of needle (708) are disclosed in U.S. patent application Ser. No. 15/609,386, entitled "Apparatus and Method to Form Entry Bleb for Subretinal Delivery of Therapeutic Agent," filed on May 31, 2017, published as U.S. Pub. No. 2017/0360607 on Dec. 21, 2017, the disclosure of which is incorporated by reference herein.

In an exemplary use, the operator may arrange magnetic pad (460), injector driver assembly (600), and injector assembly (700) as shown in FIG. 8. Before or after arranging magnetic pad (460), injector driver assembly (600), and injector assembly (700) as shown in FIG. 8, the operator may carry out the steps shown in FIGS. 9A-9L as described above. The operator may then form a scelrotomy in the eye (301) of the patient and insert cannula (702) into the eye (301) via the sclerotomy. To assist in the formation of the sclerotomy, the operator may use a marking instrument as described in U.S. patent application Ser. No. 15/609,419, the disclosure of which is incorporated by reference herein. To assist in the insertion of cannula (702) into the sclerotomy along a substantially tangential path, the operator may use a guide tack as described in U.S. patent application Ser. No. 15/609,419, the disclosure of which is incorporated by reference herein. As another merely illustrative alternative, the operator may use a suture loop assembly (332). Cannula (702) may then be advanced to position as shown in FIGS. 4C-4D with reference to cannula (50).

With cannula (702) positioned as shown in FIGS. 4C-4D with reference to cannula (50), the operator may then rotate knob (602) to advance needle (708) distally as shown in FIGS. 4E and 5A with reference to needle (100). During this advancement of needle (708), control module (500) will automatically provide bleb fluid (340) through needle (708) based on a signal from linear sensor (660), ultimately resulting in a configuration similar to that shown in FIGS. 4G and 5B. After needle (708) has been sufficiently advanced, the operator actuates pushbutton (604). This causes control module (500) to provide therapeutic agent (341) through needle (708), ultimately resulting in a configuration similar to that shown in FIGS. 4H and 5C. The operator then rotates knob (602) in reverse to retract needle (708) back into cannula (702). With needle (708) retracted, the operator then withdraws cannula (702) from the eye (301) and securely closes the sclerotomy using any suitable technique.

IV. Exemplary Injector Assembly with Integrated Control

While the combination of injector driver assembly (600), injector assembly (700), and push-pull cable (692) may enable greater safety, precision, and consistency in the delivery of therapeutic agent (341) to the eye (301), it may be desirable to provide the same results using instrumentation that is more compact. Reducing the instrument form factor and eliminating push-pull cable (692) may provide instrumentation that is easier to handle; and may remove some hysteresis that might otherwise occur and potentially have an adverse effect on the precision of control. To that end, FIGS. 28-29 show an exemplary alternative injector assembly (800) that is operable to provide the same results that are provided by injector driver assembly (600), injector assembly (700), and push-pull cable (692), but through a more compact device.

Figure 28:
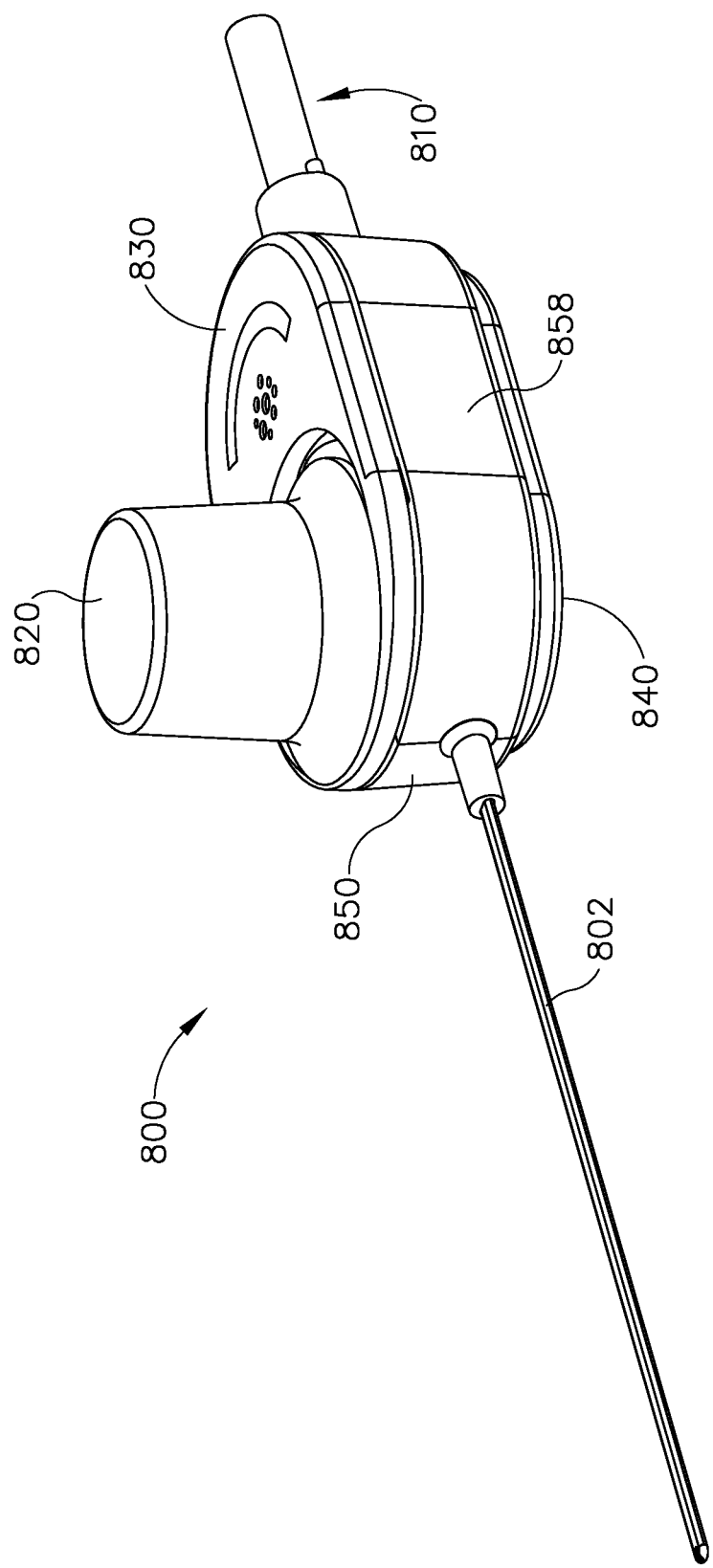
FIG. 28 depicts a perspective view of an exemplary alternatively injector assembly that may be incorporated into the system of FIG. 6.
Figure 29:
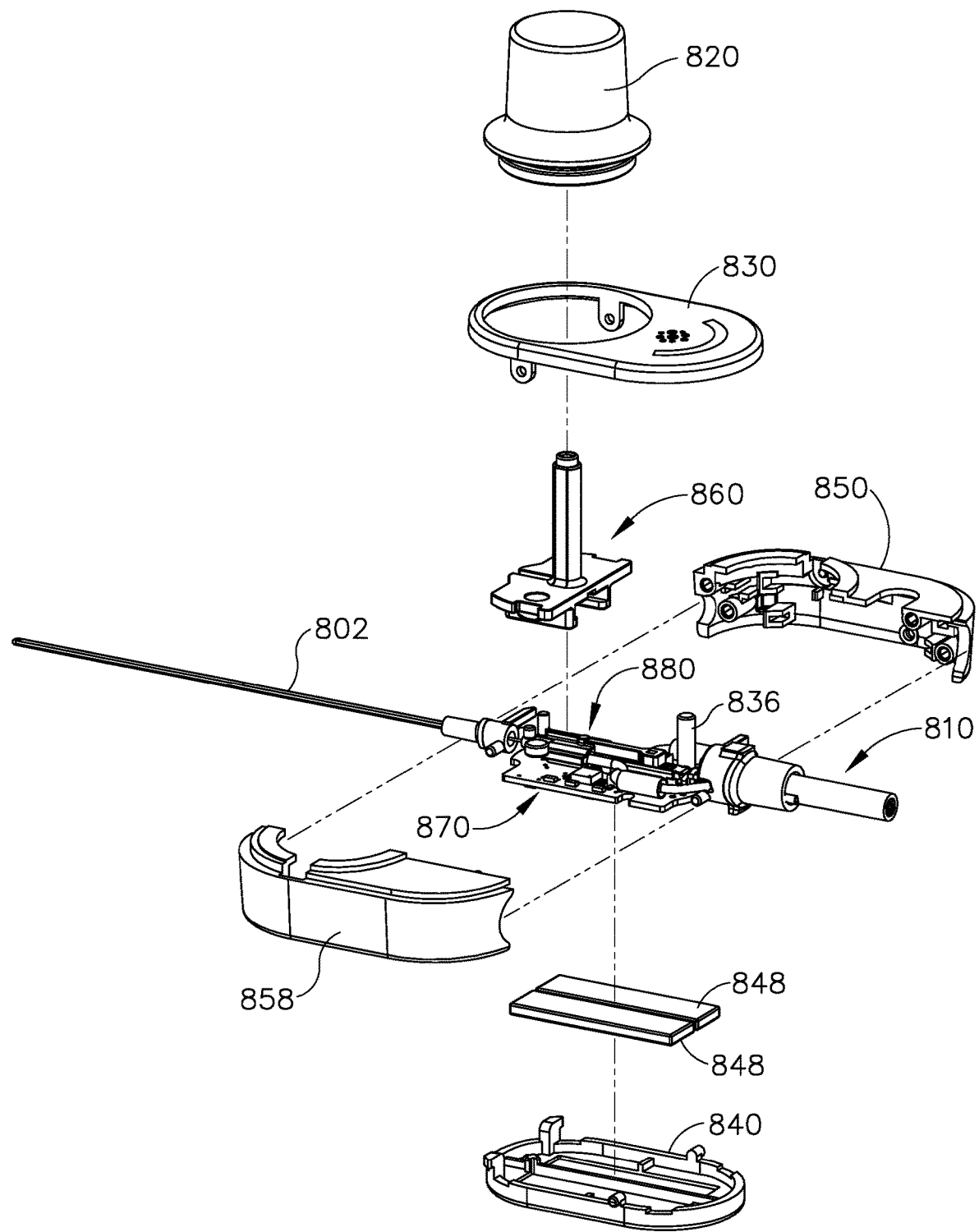
FIG. 29 depicts an exploded perspective view of the injector assembly of FIG. 28.

As shown in FIG. 28, injector assembly (800) of this example comprises a cannula (802), a rotary knob (820), an upper rocker plate (830), a lower rocker plate (840), and a pair of housing halves (850, 858). As shown in FIG. 29, injector assembly (800) further includes a frame member (860), a circuit board assembly (870), a needle driver (880), and a pair of magnets (848). A tube set (810) extends proximally from injector assembly (800). Each of these components and associated components will be described in greater detail below.

Figure 30A:
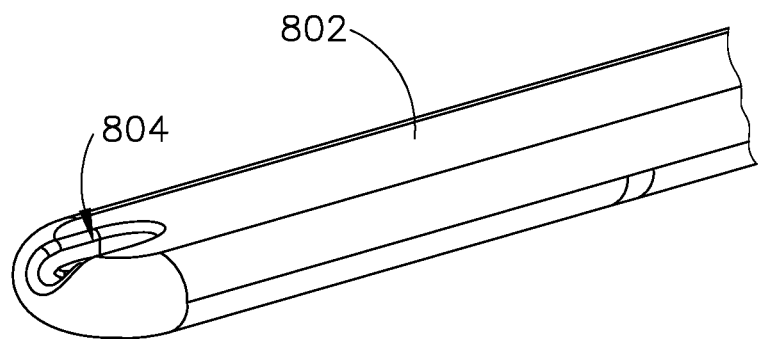
FIG. 30A depicts a perspective view of the distal end of a cannula of the injector assembly of FIG. 28, with a needle retracted in the cannula.
Figure 30B:
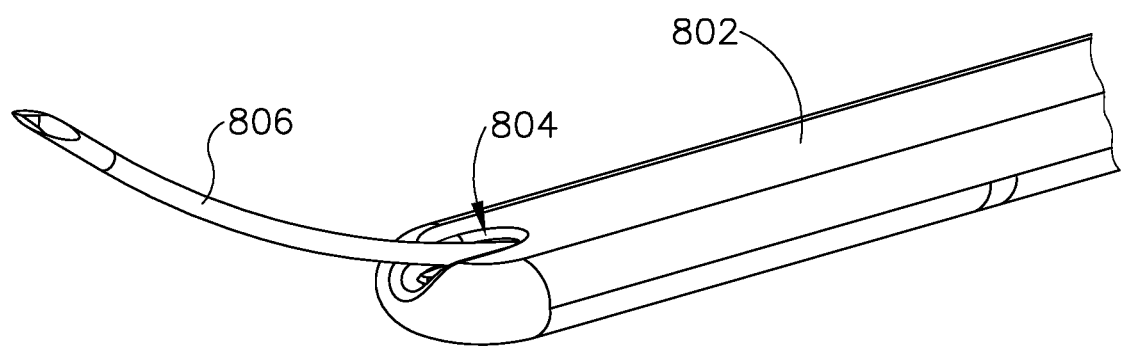
FIG. 30B depicts a perspective view of the distal end of a cannula of FIG. 30A, with a needle extending from the cannula.

As shown in FIGS. 30A-30B, cannula (802) of this example includes a distal, transversely oriented opening (804). A needle (806) is configured to be advanced distally through opening (804), as shown in FIG. 30B. In some versions, needle (806) has a preformed bend as described in U.S. patent application Ser. No. 15/438,918, entitled "Apparatus for Subretinal Administration of Therapeutic Agent via a Curved Needle," filed Feb. 22, 2017, the disclosure of which is incorporated by reference herein.

Figure 31:
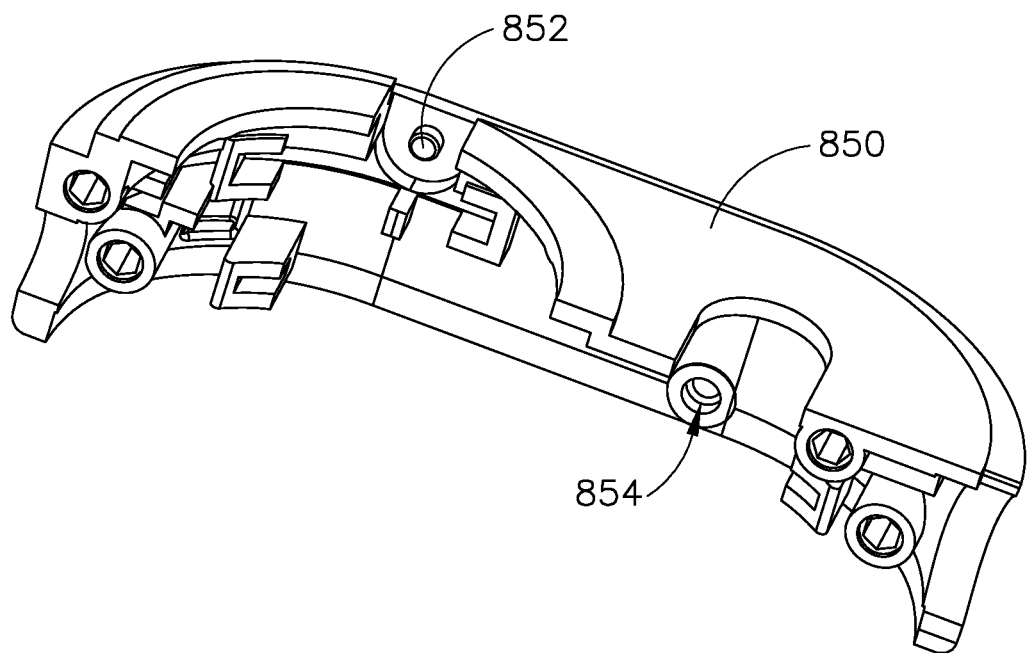
FIG. 31 depicts a perspective view of a housing half of the injector assembly of FIG. 28.
Figure 32:
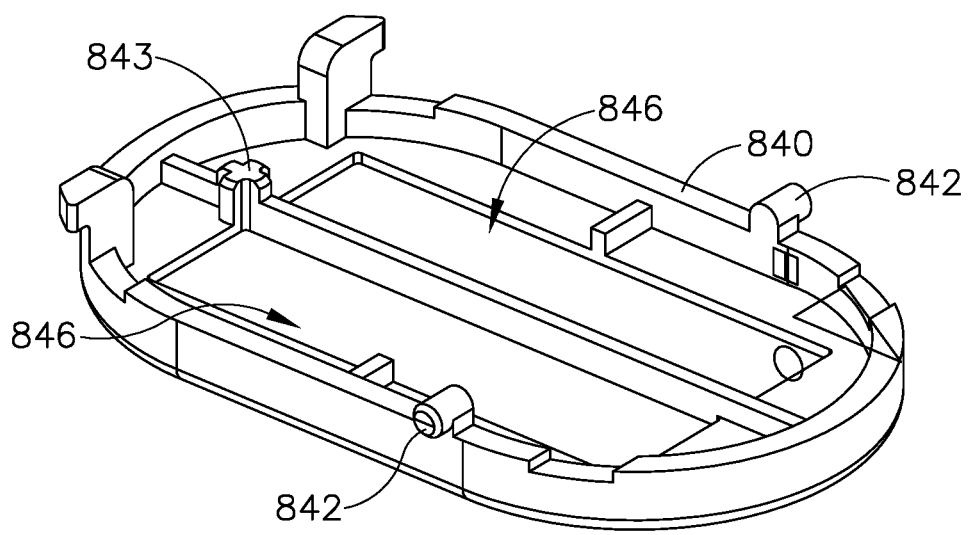
FIG. 32 depicts a perspective view of a lower rocker plate of the injector assembly of FIG. 28.
Figure 33:
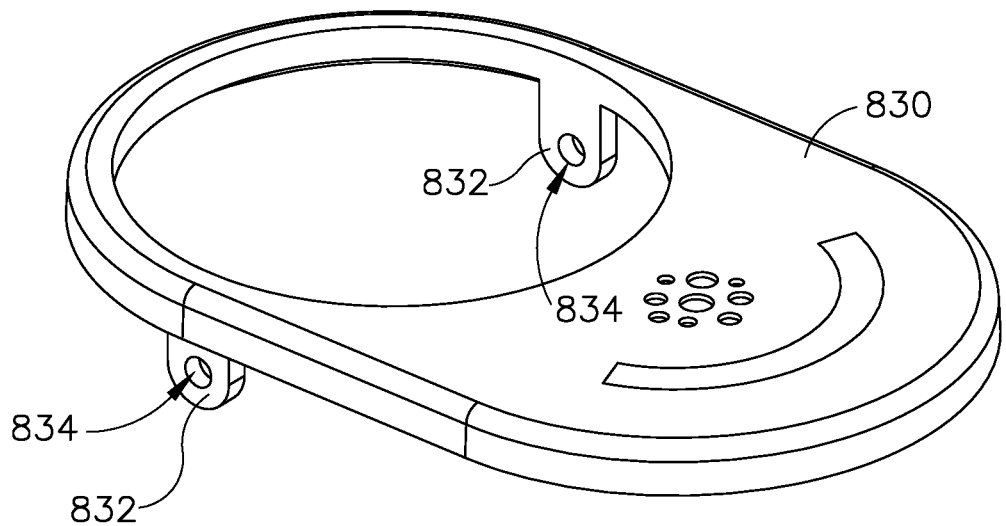
FIG. 33 depicts a perspective view of an upper rocker plate of the injector assembly of FIG. 28.
Figure 34:
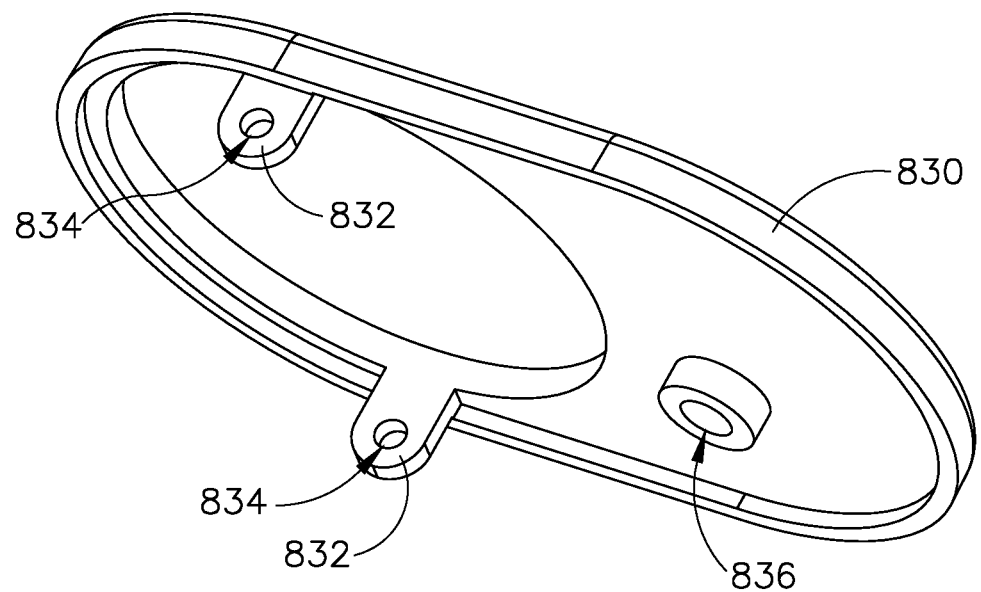
FIG. 34 depicts another perspective view of the upper rocker plate of FIG. 33.

As shown in FIG. 31, housing half (850) includes an inwardly extending integral pivot post (852) and an integral post seat (854). While not shown, it should be understood that housing half (858) may also include an inwardly extending integral pivot post (852) and an integral post seat (854). As shown in FIG. 32, lower rocker plate (840) includes a pair of outwardly extending pivot posts (842) that are positioned and configured to be seated in integral post seats (854) of housing halves (850, 858) to provide a pivotal coupling between lower rocker plate (840) and housing halves (850, 858). As shown in FIGS. 33-34, upper rocker plate (830) includes a pair of downwardly protruding tabs (832) with openings (834) formed therein. Openings (834) are positioned and configured to receive pivot posts (852) of housing halves (850, 858) to provide a pivotal coupling between lower rocker plate (840) and housing halves (850, 858).

Figure 35:
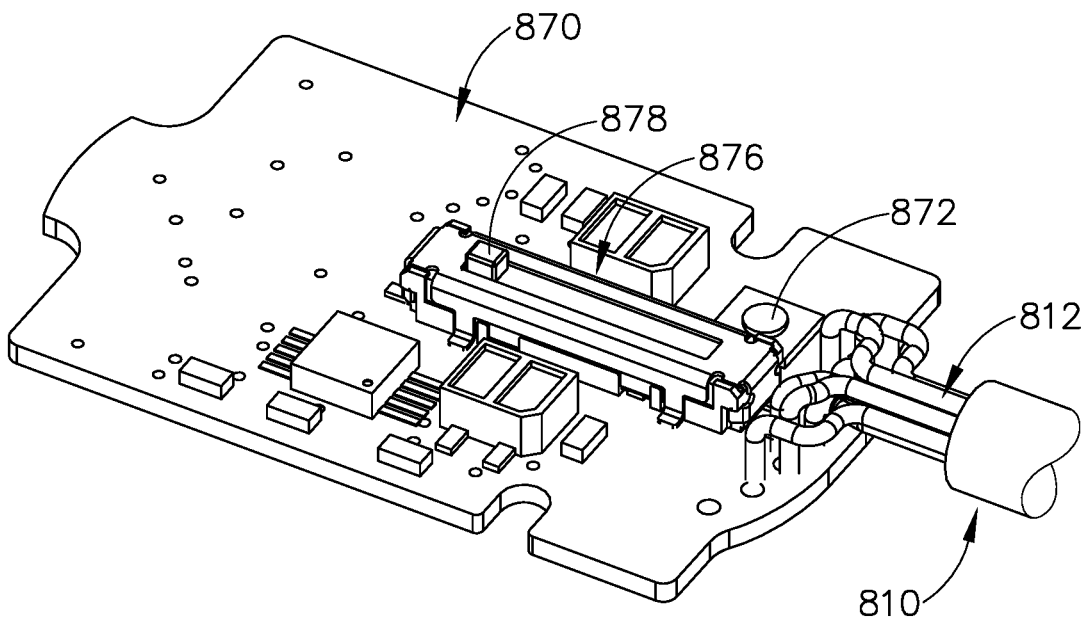
FIG. 35 depicts a perspective view of a circuit board assembly of the injector assembly of FIG. 28.

As shown in FIG. 35, an upper side of circuit board assembly (870) comprises a first tactile switch (872) and a linear sensor (876). First tactile switch (872) is positioned to be actuated by a dowel (836) (FIG. 29) that is positioned between first tactile switch (872) and a dowel seat (836) (FIG. 34) on the underside of upper rocker plate (840). The operator may provide such actuation of tactile switch (872) by pressing upper rocker plate (840) to cause upper rocker plate (840) to pivot about pivot posts (852), which will drive dowel (836) downwardly toward first tactile switch (872). First tactile switch (872) may communicate with control module (500) via one or more of wires (812) contained in tube set (810). By way of example only, control module (500) may provide delivery of therapeutic agent (341) via needle (806) in response to actuation of first tactile switch (872), similar to the delivery of therapeutic agent (341) via needle (708) in response to actuation of tactile switch (624) as described above.

In the present example, tactile switch (872) is located near the proximal end of injector assembly (800); while tactile switch (874) is located near the distal end of injector assembly (800). In addition, the pivot points for upper rocker plate (830) are located near the distal end of injector assembly (800); while the pivot points for lower rocker plate (840) are located near the distal end of injector assembly (800). Positioning the pivot points and tactile switches (872, 874) in this way may reduce the risk of an operator inadvertently actuating tactile switch (872) while attempting to actuate tactile switch (874); and vice-versa.

Linear sensor (876) includes a slider (878) and is configured and operable just like linear sensor (660) described above. Linear sensor (876) is in communication with control module (500) via one or more of wires (812) contained in tube set (810). Control module (500) is configured to provide automated delivery of bleb fluid (340) via needle (806) in response to distal movement of needle (806) as sensed by linear sensor (876).

Figure 36:
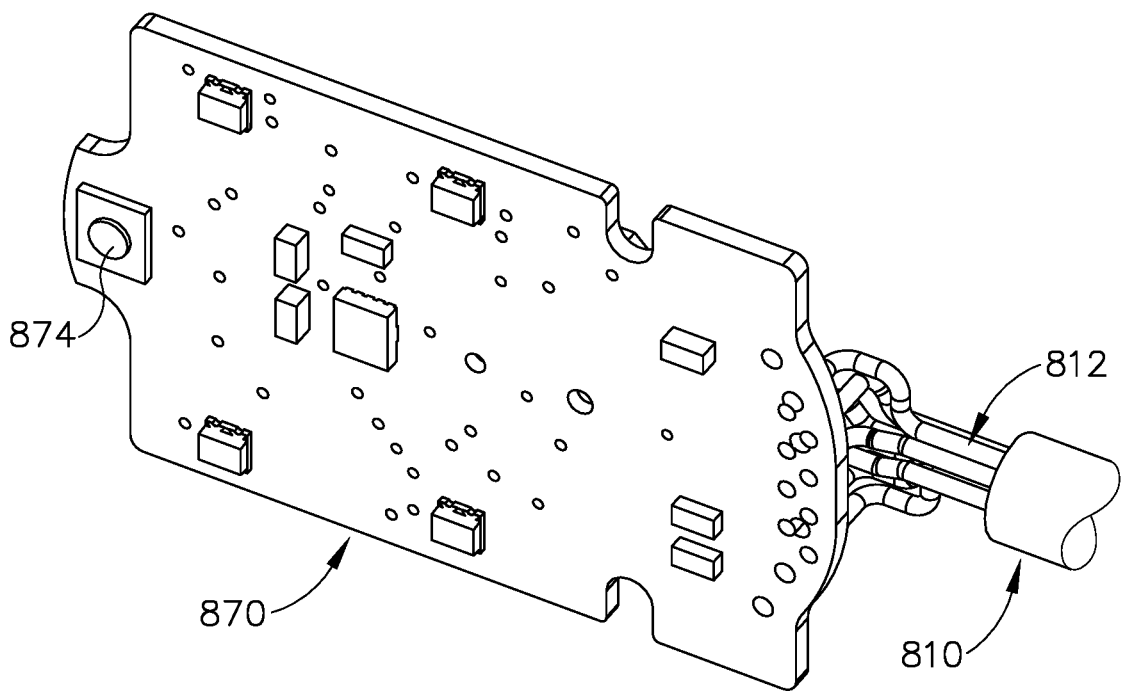
FIG. 36 depicts another perspective view of the circuit board assembly of FIG. 35.

As shown in FIG. 36, the underside of circuit board assembly (870) includes a second tactile switch (874). Second tactile switch (874) is positioned to be actuated by an integral post (843) (FIG. 32) of lower rocker plate (840). The operator may provide such actuation of tactile switch (874) by pivotably urging housing halves (850, 858) downwardly to cause housing halves (850, 858) to pivot about pivot posts (842), which will drive tactile switch (874) downwardly toward integral post (843). Second tactile switch (874) may communicate with control module (500) via one or more of wires (812) contained in tube set (810). By way of example only, control module (500) may provide delivery of bleb fluid (340) via needle (806) in response to actuation of second tactile switch (874), similar to the delivery of bleb fluid (340) via needle (708) in response to actuation of tactile switch (632) as described above.

Referring back to FIG. 32, a pair of recesses (846) are formed in the bottom of lower rocker plate (840). Recesses (846) are configured to receive elongate magnets (848). Magnets (848) provide magnetic attraction to magnetic pad (460), similar to magnets (706) described above. Magnets (848) thus enable injector assembly (800) to be removably secured to magnetic pad (460), to be easily repositioned on magnetic pad (460), and to be easily removed from magnetic pad (460). As noted above, magnetic pad (460) may take a variety of alternative forms; and other suitable structures and techniques may be used to removably secure injector assembly (800) relative to a patient.

Figure 37:
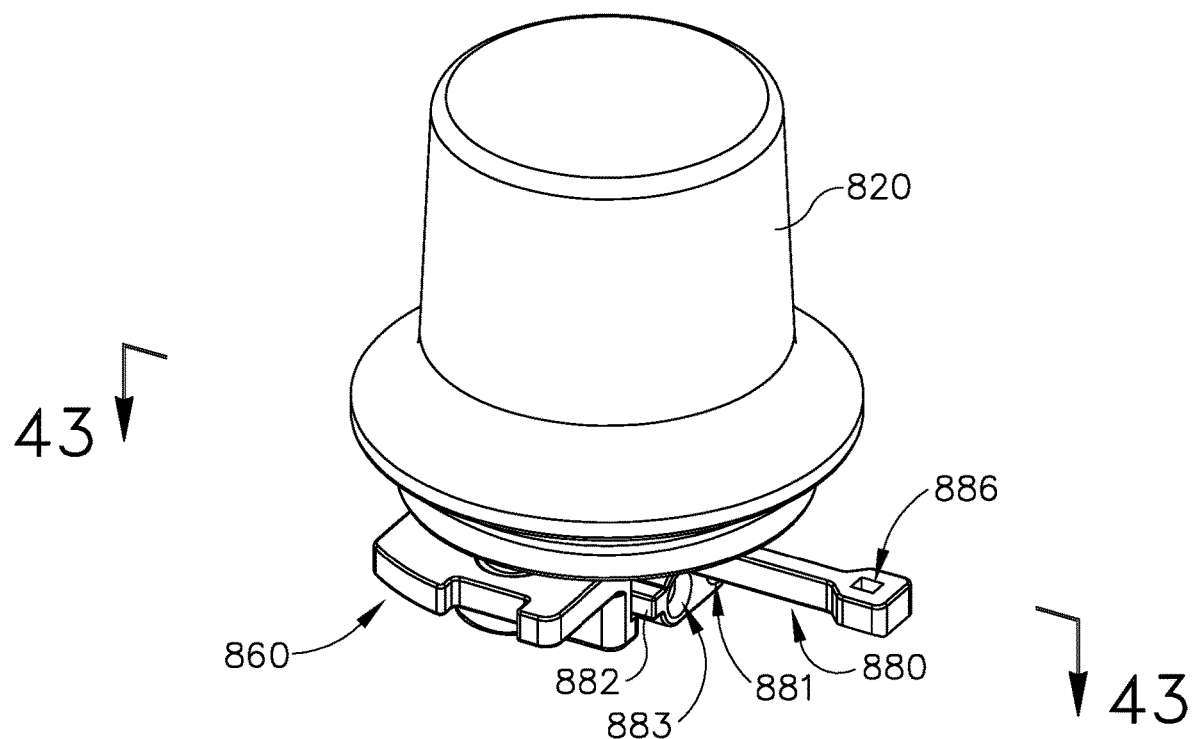
FIG. 37 depicts a perspective view of a needle actuation assembly of the injector assembly of FIG. 28.
Figure 38:
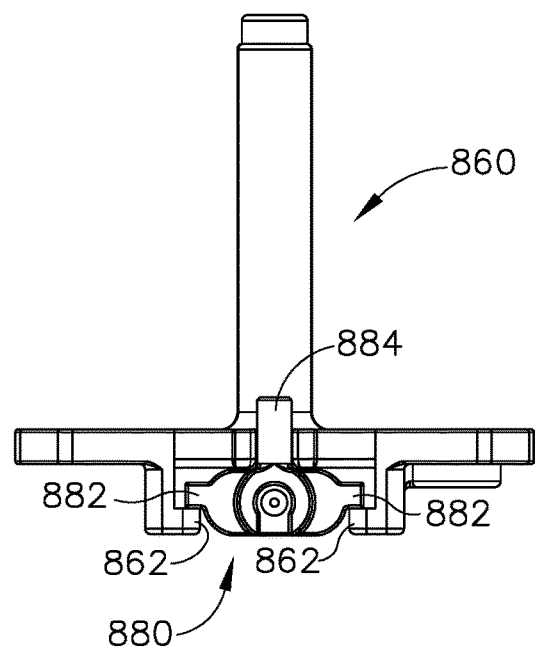
FIG. 38 depicts a front elevational view of a frame member and a needle driver of the needle actuation assembly of FIG. 37.

As shown in FIGS. 37-38, rotary knob (828), frame member (860), and needle actuator (880) are coupled together to form an assembly. Rotary knob (820) is operable to rotate relative to housing halves (850, 858). Frame member (860) is configured to be unitarily secured to housing halves (850, 858), such that frame member (860) remains stationary relative to housing halves (850, 858).

Figure 39:
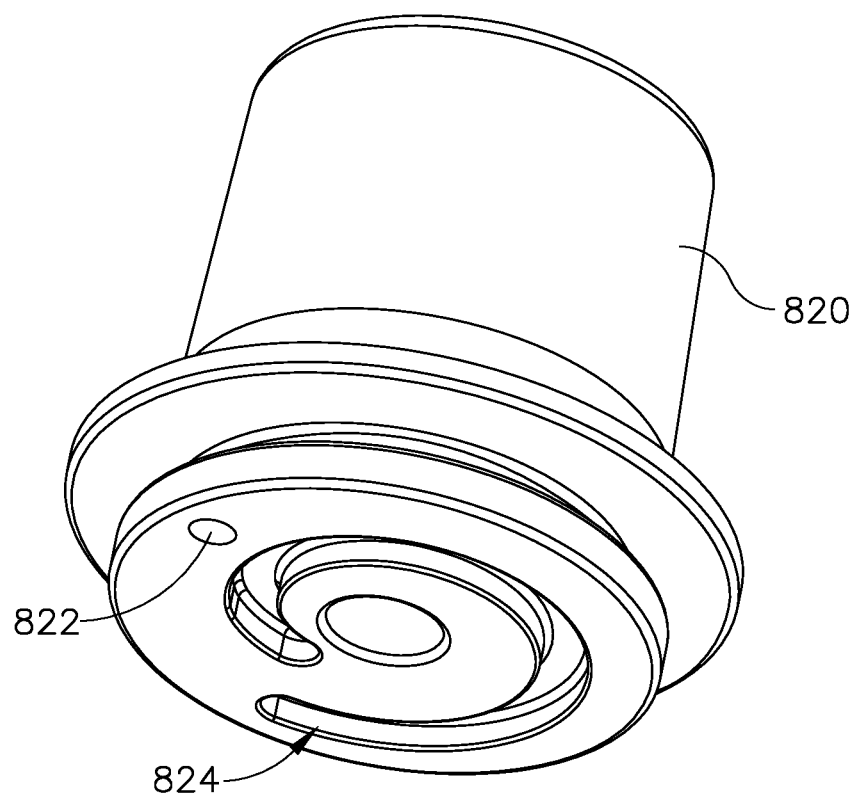
FIG. 39 depicts a perspective view of a rotary cam of the needle actuation assembly of FIG. 37.
Figure 40:
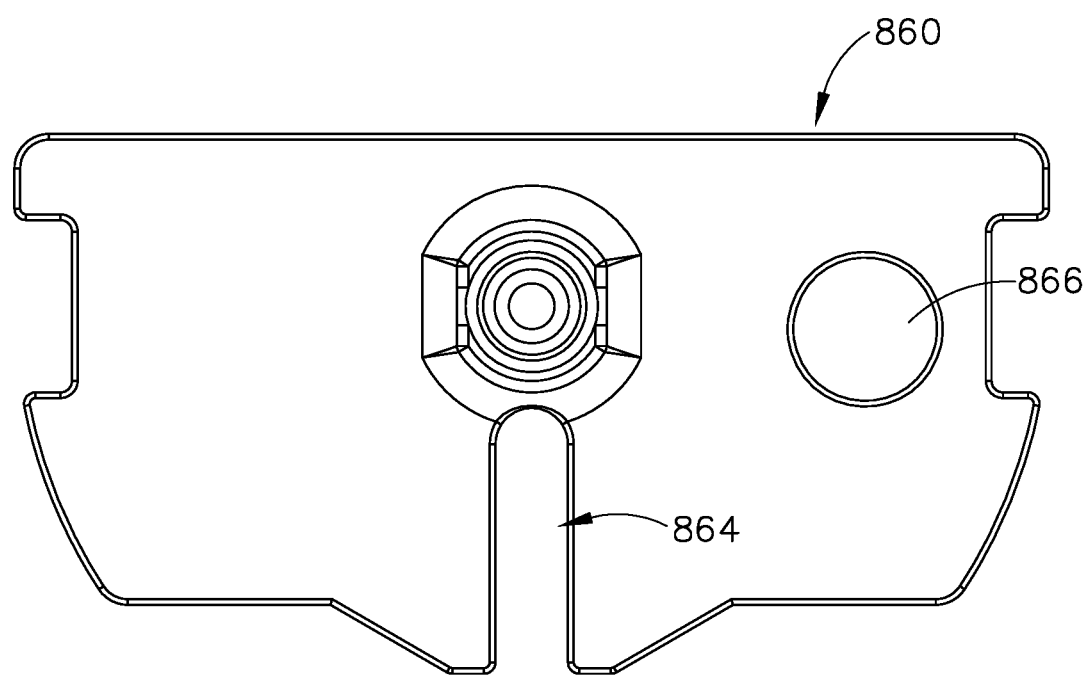
FIG. 40 depicts a top plan view of the frame member of FIG. 38.
Figure 41:
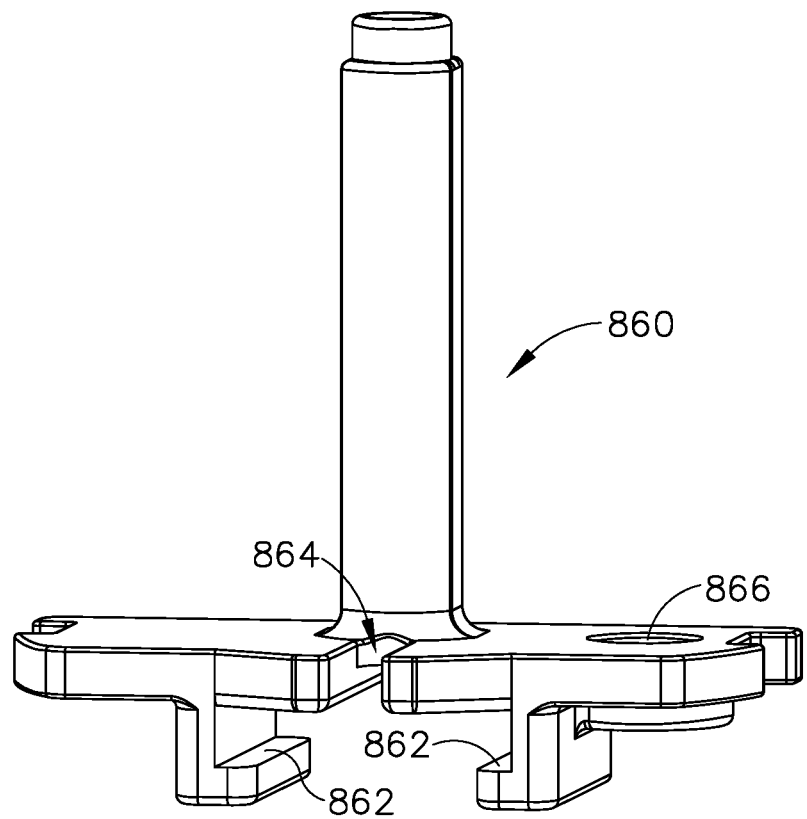
FIG. 41 depicts a perspective view of the frame member of FIG. 38.
Figure 42:
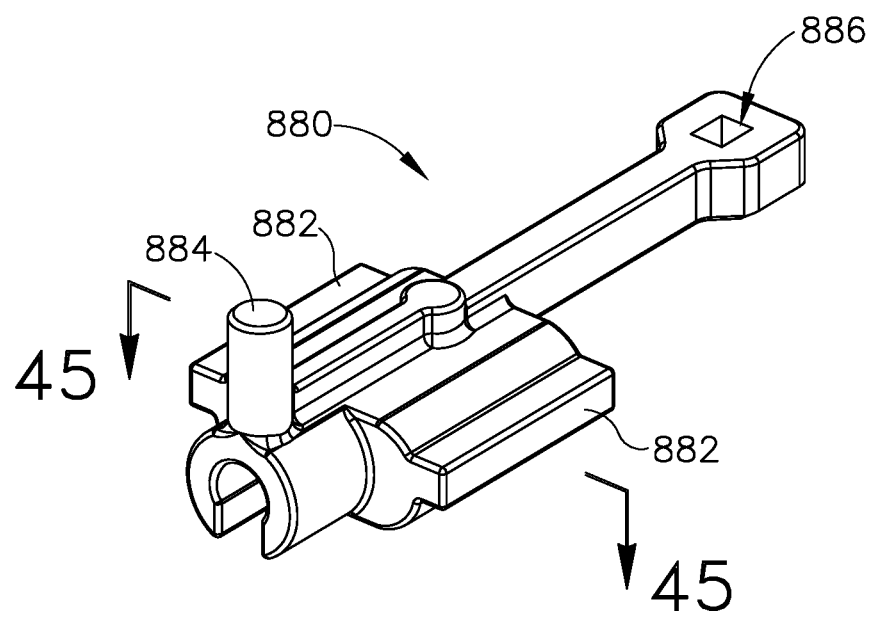
FIG. 42 depicts a perspective view of the needle driver of FIG. 38.

Needle actuator (880) is operable to translate relative to housing halves (850, 858), in response to rotation of rotary knob (820) relative to housing halves (850, 858). As shown in FIG. 39, the underside of rotary knob (820) includes a spiral cam recess (824) and a magnet (822). As shown in FIGS. 40-41, frame member (860) includes a pair of support rails (862), a guide slot (864), and a magnet (866). As shown in FIG. 42, needle actuator (880) comprises a pair of guide wings (882), a cam follower post (884), and a proximal opening (886).

Referring back to FIGS. 37-38, guide wings (882) are sized and configured to engage support rails (862). This engagement provides vertical and lateral support to needle actuator (880), while permitting needle actuator (880) to slide longitudinally relative to frame member (860). Guide slot (864) is configured to receive cam follower post (884) and accommodate sliding movement thereof as needle actuator (880) slides longitudinally relative to frame member (860). Proximal opening (886) is positioned and configured to receive slider (878) of linear sensor (876), such that slider (878) will slide unitarily with needle actuator (880).

Figure 43A:
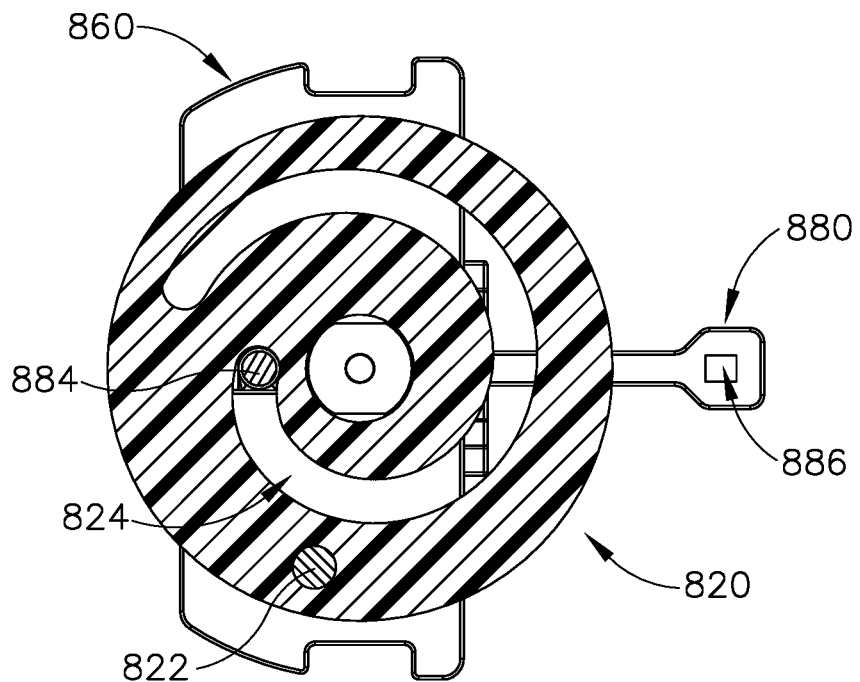
FIG. 43A depicts a cross-sectional view, taken along line 43-43 of FIG. 37, of the needle actuation assembly of FIG. 37, with the rotary cam of FIG. 39 at a first angular position and the needle driver of FIG. 38 in a proximal position.
Figure 43B:
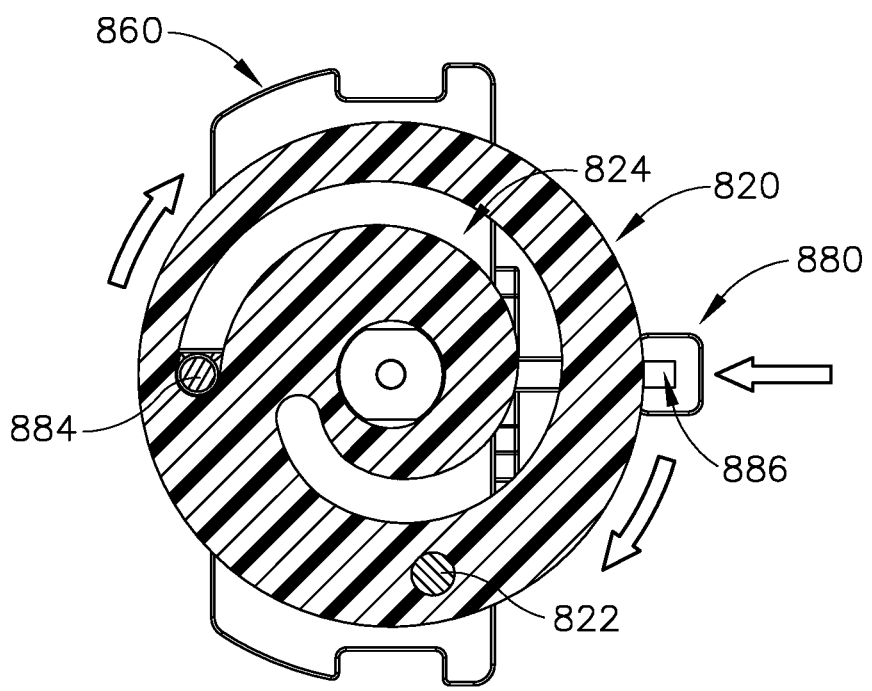
FIG. 43B depicts a cross-sectional view, taken along line 43-43 of FIG. 37, of the needle actuation assembly of FIG. 37, with the rotary cam of FIG. 39 at a second angular position and the needle driver of FIG. 38 in a distal position.

As shown in FIGS. 43A-43B, cam follower post (884) of needle actuator (880) is configured to fit in spiral cam recess (824) of rotary knob (820). Due to this engagement, and due to guidance provided to cam follower post (884) by guide slot (864), needle actuator (880) will translate from a proximal position (FIG. 43A) to a distal position (FIG. 43B) in response to rotation of rotary knob (820). Needle (806) is fixedly secured to needle actuator (880) as described in greater detail below, such that needle (806) will translate longitudinally relative to cannula (802) in response to rotation of rotary knob (820). In the present example, magnets (822, 866) are positioned such that magnet (822) will be located directly over magnet (866) when rotary knob (820) is in a home position as shown in FIG. 43A. In this stage, magnets (822, 866) prevent rotary knob (420) from being rotated inadvertently; yet permit intentional rotation of rotary knob (420). In some other variations, magnets (822, 866) are positioned such that magnet (822) will be located directly over magnet (866) when rotary knob (820) is in the fully rotated position as shown in FIG. 43B.

Figure 44:
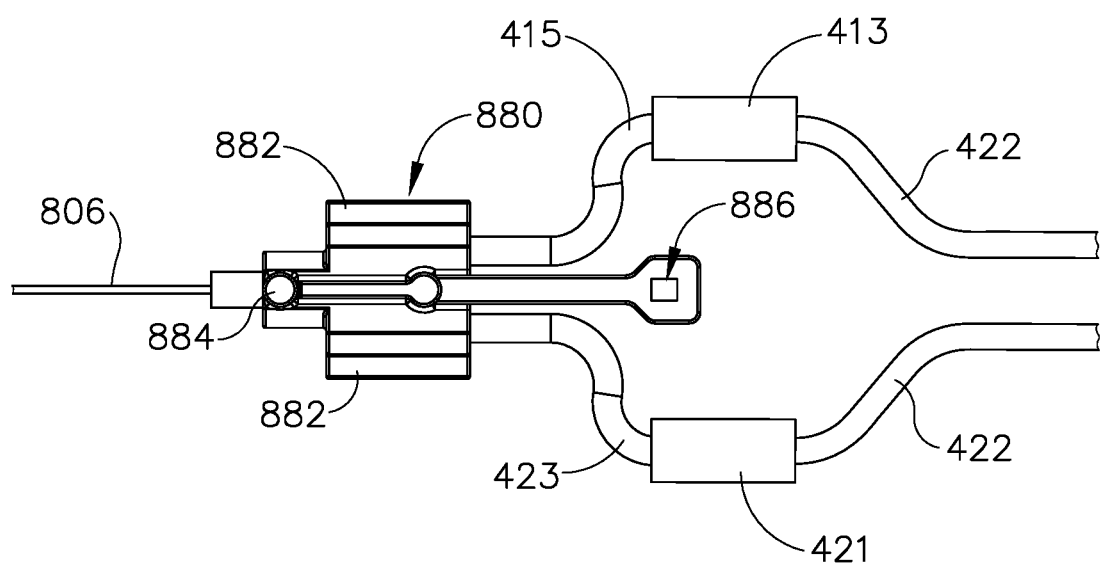
FIG. 44 depicts a top plan view of the needle driver of FIG. 38 with fluid conduits coupled thereto.
Figure 45:
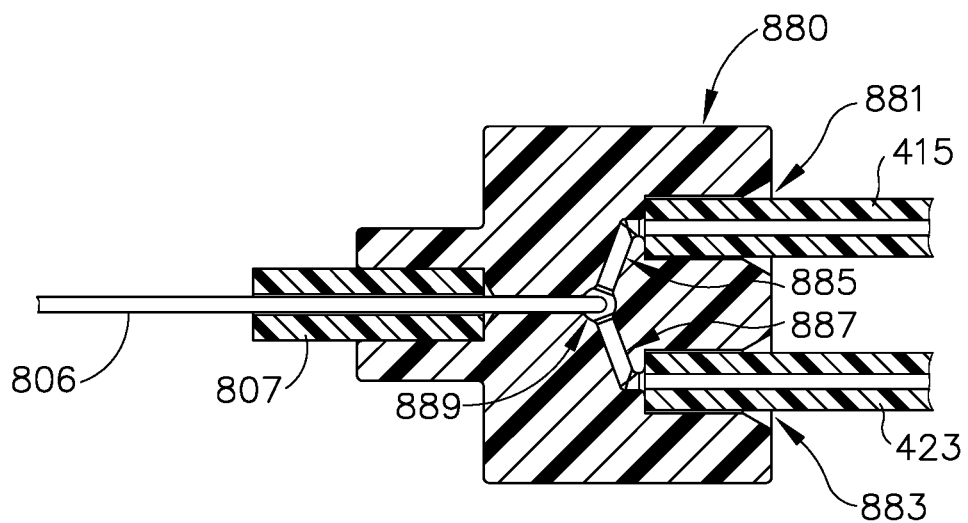
FIG. 45 depicts a cross-sectional view of the needle driver of FIG. 38, taken along line 45-45 of FIG. 42, with the fluid conduits of FIG. 44 coupled thereto.

As shown in FIGS. 44-45, needle (806) extends distally from the distal end of needle actuator (880) and is fixedly secured thereto by a ferrule (807). Conduits (415, 423) extend proximally from the proximal end of needle actuator (880). Conduit (415) is coupled with a one-way valve assembly (413), which is further coupled with conduit (422). As noted above, conduit (422) is in communication with syringe actuation cassette (550) and is configured to deliver bleb fluid (340). One-way valve assembly (413) is configured to provide fluid delivery only from conduit (422) to conduit (415); and to prevent fluid delivery from conduit (415) to conduit (422). Conduit (423) is coupled with a one-way valve assembly (421), which is further coupled with conduit (424). As noted above, conduit (424) is in communication with syringe actuation cassette (550) and is configured to deliver therapeutic agent (431). One-way valve assembly (421) is configured to provide fluid delivery only from conduit (424) to conduit (423); and to prevent fluid delivery from conduit (423) to conduit (424). Various structures that may be incorporated into one-way valve assemblies (413, 421) will be apparent to those of ordinary skill in the art in view of the teachings herein. Conduits (422, 424) are integrated into tube set (810), along with wires (872).

As shown in FIG. 45, the distal end of conduit (415) is inserted into a proximal opening (881) of needle actuator (880), while the distal end of conduit (423) is inserted into another proximal opening (883) of needle actuator (880). Proximal opening (881) is in fluid communication with a lumen (885) formed in needle actuator (880), while proximal opening (883) is in fluid communication with a lumen (887) formed in needle actuator (880). Lumens (885, 887) are in fluid communication with a chamber (889) formed in needle actuator (880). The proximal end of needle (806) is positioned in chamber (889). Thus, needle (806) receives fluids (840, 841) communicated through conduits (415, 413). Needle actuator (880) thus defines a fluid manifold.

In an exemplary use, the operator may arrange magnetic pad (460) as shown in FIG. 8, and place injector assembly (800) on magnetic pad (460). Before or after arranging magnetic pad (460) and injector assembly (800), the operator may carry out the steps shown in FIGS. 9A-9L as described above. The operator may then form a scelrotomy in the eye (301) of the patient and insert cannula (802) into the eye (301) via the sclerotomy. To assist in the formation of the sclerotomy, the operator may use a marking instrument as described in U.S. patent application Ser. No. 15/609,419, the disclosure of which is incorporated by reference herein. To assist in the insertion of cannula (802) into the sclerotomy along a substantially tangential path, the operator may use a guide tack as described in U.S. patent application Ser. No. 15/609,419, the disclosure of which is incorporated by reference herein. As another merely illustrative alternative, the operator may use a suture loop assembly (332). Cannula (802) may then be advanced to position as shown in FIGS. 4C-4D with reference to cannula (50).

With cannula (802) positioned as shown in FIGS. 4C-4D with reference to cannula (50), the operator may then rotate knob (820) to advance needle (806) distally as shown in FIGS. 4E and 5A with reference to needle (100). During this advancement of needle (806), control module (500) will automatically provide bleb fluid (340) through needle (806) based on a signal from linear sensor (876), ultimately resulting in a configuration similar to that shown in FIGS. 4G and 5B. After needle (806) has been sufficiently advanced, the operator actuates upper rocker plate (830). This causes control module (500) to provide therapeutic agent (341) through needle (806), ultimately resulting in a configuration similar to that shown in FIGS. 4H and 5C. The operator then rotates knob (820) in reverse to retract needle (806) back into cannula (802). With needle (806) retracted, the operator then withdraws cannula (802) from the eye (301) and securely closes the sclerotomy using any suitable technique.

V. Exemplary Alternative Injector System

As noted above, there may be a risk that cells in therapeutic agent (341) are damaged in the event that therapeutic agent (341) is communicated through conduit (424) too quickly. This risk may be particularly pronounced during the priming process, when therapeutic agent (341) needs to travel a substantial length to reach needle (100, 708, 806). It may therefore be desirable to ensure that cells in therapeutic agent (341) are not damaged by communicating therapeutic agent (341) is communicated through conduit (424) too quickly.

Figure 46:
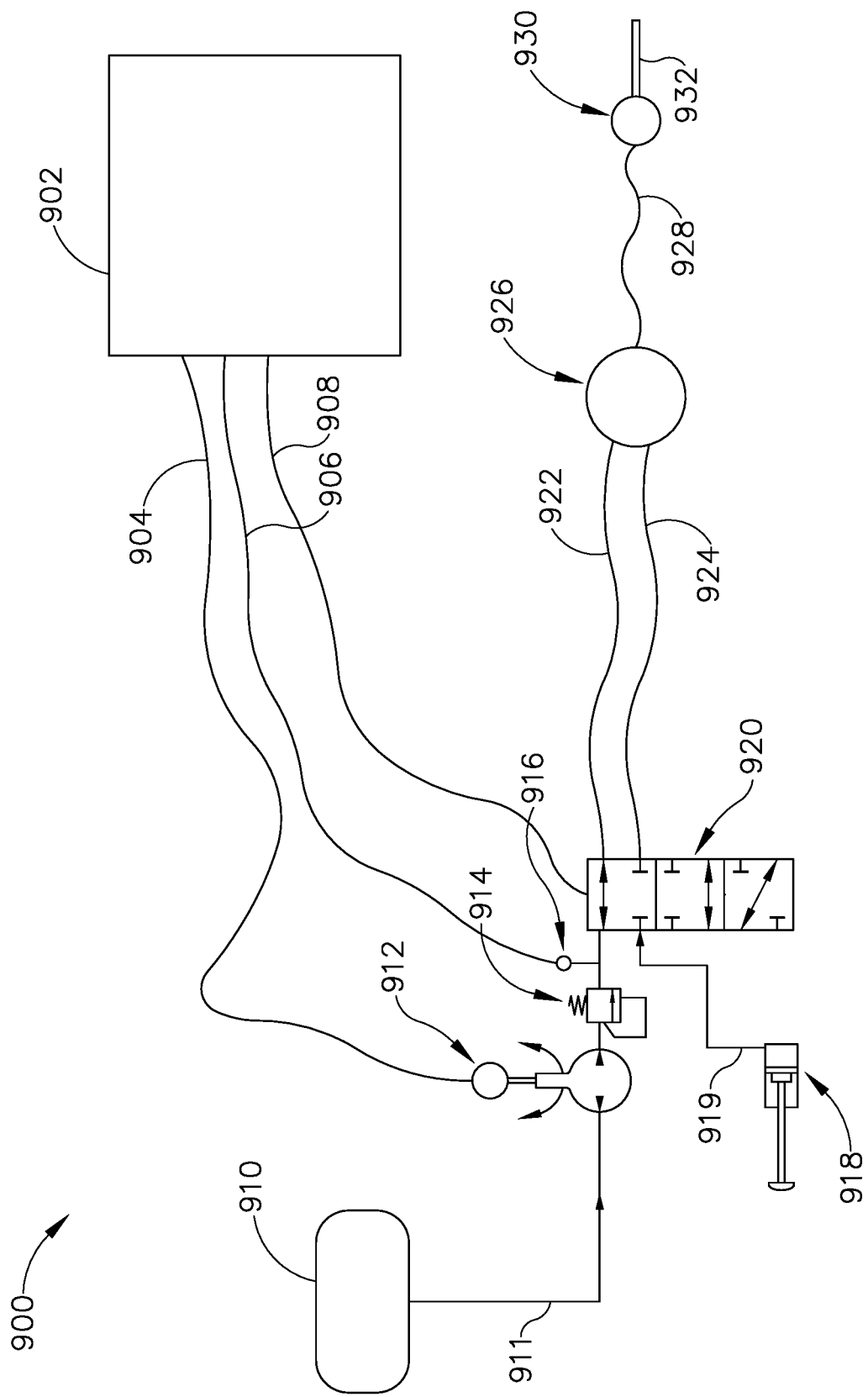
FIG. 46 depicts a schematic view of an exemplary alternative system for subretinal administration of a therapeutic agent from a suprachoroidal approach.

FIG. 46 shows a system (900) that represents a modified version of system (400), with the inclusion of an air gap behind therapeutic agent (341) during the priming process.

System (900) of this example comprises a control module (902), a BSS reservoir (910), a pump (912), a pressure regulator (914), an occlusion detector (916), a syringe assembly (918), a three-position four-way valve (920), an injector driver assembly (926), and an injector assembly (930). Control module (902) is in communication with pump (912) via a first wire (904); with occlusion detector (916) via a second wire (906); and with three-position four-way valve (920) via a third wire (908).

BSS reservoir (910) contains a volume of bleb fluid (340). BSS reservoir (910) is coupled with pump (912) via conduit (911). Pump (912) is operable to pump bleb fluid (340) from BSS reservoir (910), through pressure regulator (914) and occlusion detector (916), to eventually reach three-position four-way valve (920).

Syringe (918) contains a volume of therapeutic agent (341). Syringe (918) is coupled with three-position four-way valve (920) via a conduit (919).

Three-position four-way valve (920) is in fluid communication with injector driver assembly (926) via tubes (922, 924). Three-position four-way valve (920) is operable to transition between three different states. In a first state, three-position four-way valve (920) couples conduit (911) with tube (922), thereby enabling communication of bleb fluid (340) through tube (922) to reach injector driver assembly (926). Also in the first state, three-position four-way valve (920) prevents communication between conduit (919) and tube (924). In a second state, three-position four-way valve (920) couples conduit (919) with tube (924), thereby enabling communication of therapeutic agent (341) through tube (924). Also in the second state, three-position four-way valve (920) prevents communication between conduit (911) and tube (922). In a third state, three-position four-way valve (920) couples conduit (911) with tube (924), thereby enabling communication of bleb fluid (340) through tube (924). Also in the third state, three-position four-way valve (920) prevents communication between conduit (919) and tube (922).

By way of example only, injector driver assembly (926) may be configured and operable like injector driver assembly (600) described above. Injector driver assembly (926) is in communication with injector assembly (930) via tube and cable assembly (928), which may be configured and operable like tube and cable assembly (690) described above. Injector assembly (930) may be configured and operable like injector assembly (700). In some alternative variations, injector driver assembly (926) and injector assembly (930) are essentially combined into a single assembly, similar to injector assembly (800) described above.

In an exemplary method of operation, system (900) begins with three-position four-way valve (920) in the state shown in FIG. 46. Pump (912) is used to drive bleb fluid (340) through conduit (911), tube (922), and a corresponding conduit in tube and cable assembly (928) to thereby prime the bleb fluid (340) path. Three-position four-way valve (920) is then actuated to transition to a state where conduit (919) is in fluid communication with tube (924). Syringe (918) is then actuated to inject a volume of therapeutic agent (341) (e.g., approximately 280 µl) through tube (924). By way of example only, tube (924) may have a length of approximately 84 inches and an inner diameter between approximately 0.03 inches and approximately 0.04 inches.

With the volume of therapeutic agent (341) injected into tube (924), an air gap is injected into tube (924), behind the volume of therapeutic agent (341). In some versions, syringe (918) is replaced with another syringe containing air, and that air-filled syringe is used to inject the air gap into tube (924) while three-position four-way valve (920) remains in a state where conduit (919) is in fluid communication with tube (924). In some other versions, three-position four-way valve (920) is switched to a state where conduit (911) is in fluid communication with tube (924), and the air gap is provided via conduit (911). In either case, and by way of example only, the air gap may have a volume of approximately 10 µl.

After the air gap is injected, if three-position four-way valve (920) is not already in a state where conduit (911) is in fluid communication with tube (924), three-position four-way valve (920) is switched to a state where conduit (911) is in fluid communication with tube (924). Pump (912) is then activated to drive a volume of bleb fluid (340) from BSS reservoir (910) to tube (924). The volume of bleb fluid (340) is selected to ensure that therapeutic agent (341) reaches injector assembly (930). The air gap between bleb fluid (340) and therapeutic agent (341) may prevent bleb fluid (340) and therapeutic agent (341) from mixing.

At this stage, tubes (922, 924) and injector assembly (930) are fully primed, such that system (900) is ready for use in a procedure as described above. During this procedure, three-position four-way valve (920) would be first switched to a state where conduit (911) is in fluid communication with tube (922), to provide bleb fluid (340) to the subretinal space. Three-position four-way valve (920) would then be switched to a state where conduit (911) is in fluid communication with tube (924), to provide therapeutic agent (341) to the subretinal space. Bleb fluid (340) and therapeutic agent (341) may be provided to the subretinal space in accordance with the teachings above with reference to FIGS. 4E-4G and FIGS. 5A-5C.

VI. Exemplary Alternative Needle Guide

As noted above, cannula (50) includes an internal needle guide (60) that slidably receives needle (100) and guides needle (100) out through lateral opening (56) of cannula (50) at a particular exit angle. It should also be understood that cannula (702) and cannula (802) may each include an internal needle guide. While such needle guides need to be flexible in order to conform to the inside curvature of the eye (301), it may also be important for such needle guides to maintain axial stiffness (tensile strength) to prevent elongation of the needle guide during an operation. Otherwise, elongation of the needle guide may adversely affect smooth movement of a needle through needle guide. It may therefore be desirable to provide a needle guide that has substantial lateral flexibility while also having substantial axial stiffness.

Figure 47:
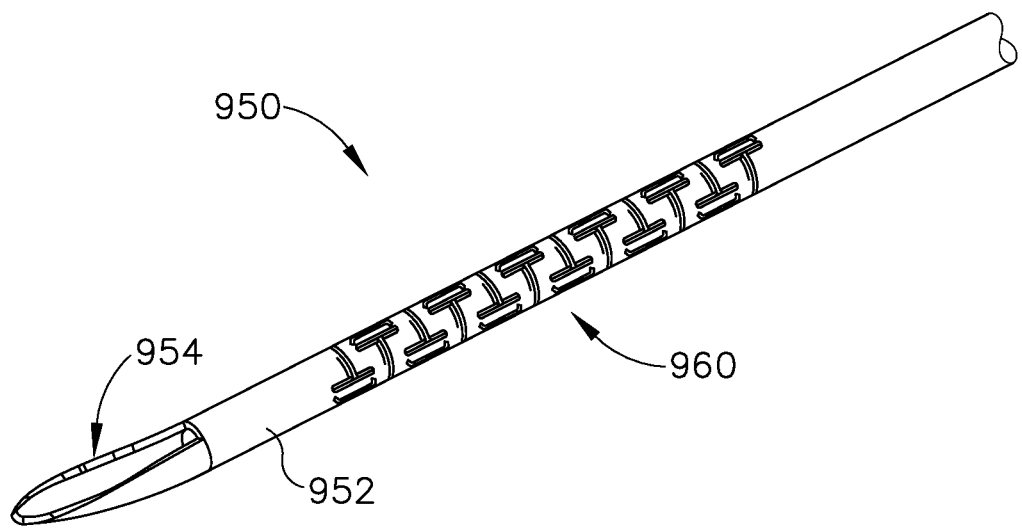
FIG. 47 depicts a perspective view of an exemplary alternative needle guide that may be disposed in a cannula of an injector.

FIG. 47 shows an exemplary needle guide (950) that may be disposed in any of the cannulae (50, 702, 802) described herein. Needle guide (950) of this example is formed of a metallic material and has a laterally oriented opening (954) at the distal end of a shaft (952), and a flex section (960) comprising a linear array of cutouts (970) formed proximally of laterally oriented opening (954). Laterally oriented opening (954) may be positioned to correspond with a lateral opening of a cannula (e.g., any of cannulae (50, 702, 802), etc.) and thereby guide a needle out through the lateral opening of the cannula. Cutouts (970) may be formed using laser cutting techniques or using any other suitable techniques.

Figure 48:
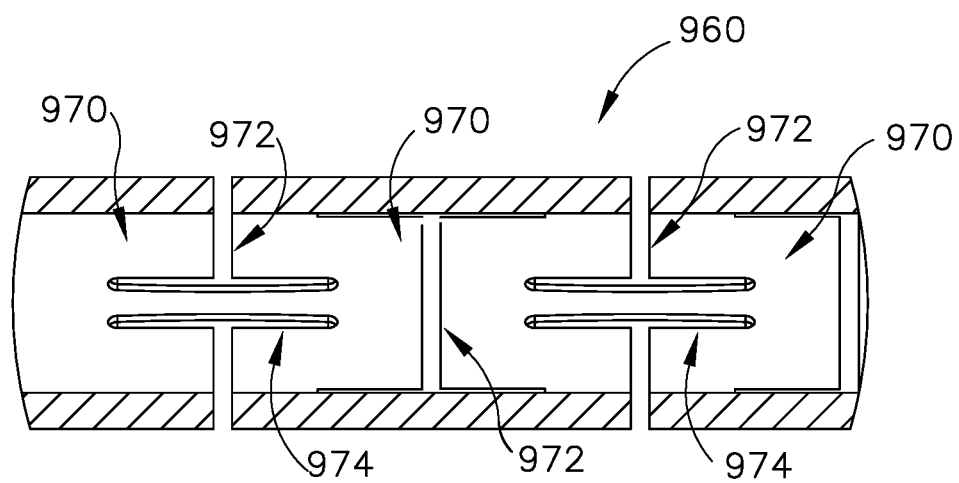
FIG. 48 depicts a cross-sectional view of a portion of the needle guide of FIG. 47.

As best seen in FIG. 48, each cutout (970) includes an angularly extending portion (972) and a pair of longitudinally extending portions (974). Each cutout (970) in the linear array of cutouts (970) is angularly offset by 90 degrees relative to the adjacent cutout (970) in the linear array of cutouts (970). The configuration and arrangement of cutouts (970) in the present example provides needle guide (950) with substantial lateral flexibility while also providing needle guide (950) with substantial axial stiffness.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a pad assembly, wherein the pad assembly is sized and configured to be placed on a forehead of a patient; (b) an injector assembly, wherein the injector assembly comprises: (i) a body, wherein the body is configured to be removably secured to the pad assembly, (ii) a flexible cannula extending distally from the body, wherein the cannula is sized to be inserted through an incision in an eye of a patient, and (iii) a needle slidably disposed in the cannula; (c) an injector driver, wherein the injector driver is operable to drive the needle longitudinally relative to the flexible cannula;
and (d) a fluid source assembly in fluid communication with the needle.

Example 2

The apparatus of Example 1, wherein the injector driver is integrated into the body.

Example 3

The apparatus of any one or more of Example 1, wherein the injector driver is remotely coupled with the injector assembly via a flexible drive cable.

Example 4

The apparatus of any one or more of Examples 1 through 3, wherein the injector assembly comprises a magnet, wherein the magnet is configured to removably secure the body to the pad.

Example 5

The apparatus of Example 4, wherein the pad comprises a plurality of ferrous elements.

Example 6

The apparatus of any one or more of Examples 1 through 5, wherein the injector assembly further includes a needle actuator positioned in the body, wherein the needle is fixedly secured to the needle actuator, wherein the needle actuator is configured to translate relative to the body to thereby drive the needle longitudinally relative to the cannula.

Example 7

The apparatus of Example 6, wherein the needle actuator further includes at least two fluid inputs in fluid communication with the needle, such that the needle actuator is configured to form a manifold.

Example 8

The apparatus of any one or more of Examples 1 through 7, wherein the injector driver comprises a rotary knob, wherein the rotary knob is rotatable to drive the needle longitudinally relative to the flexible cannula.

Example 9

The apparatus of Example 8, wherein the rotary knob includes a spiral cam feature, wherein the spiral cam feature is configured to cooperate with another needle drive element to thereby drive the needle longitudinally in response to rotary movement of the rotary actuator.

Example 10

The apparatus of any one or more of Examples 8 through 9, wherein the injector driver further comprises a translatable member having a cam follower coupled with the spiral cam feature, wherein the cam follower and the spiral cam feature are configured to cooperate to thereby convert rotary movement of the rotary knob into longitudinal movement of the needle.

Example 11

The apparatus of any one or more of Examples 1 through 10, wherein the injector driver further comprises a first user input feature, wherein the first user input feature is operable to provide delivery of a therapeutic agent via needle.

Example 12

The apparatus of Example 11, wherein the first user input feature comprises a pushbutton.

Example 13

The apparatus of any one or more of Examples 1 through 13, wherein the injector driver further comprises a bleb fluid delivery input feature, wherein the bleb fluid delivery input feature is operable to provide delivery of a bleb fluid via needle.

Example 14

The apparatus of Example 13, wherein the bleb fluid delivery feature comprises a sensor, wherein the sensor is configured to sense a position of the needle in relation to the body.

Example 15

The apparatus of Example 14, wherein the sensor comprises a linear potentiometer.

Example 16

The apparatus of any one or more of Examples 1 through 15, wherein the fluid source assembly comprises a syringe actuation cassette, wherein the syringe actuation cassette is configured to provide automatic actuation of a syringe to thereby expel contents of the syringe through the needle.

Example 17

The apparatus of any one or more of Examples 1 through 16, wherein the fluid source assembly further includes a thawing module, wherein the thawing module is operable to thaw a volume of frozen therapeutic agent.

Example 18

An apparatus, comprising: (a) a pad assembly, wherein the pad assembly is sized and configured to be placed on a forehead of a patient, wherein the pad assembly comprises at least one ferrous element; and (b) an injector assembly, wherein the injector assembly comprises: (i) a body, wherein the body is configured to be removably secured to the pad assembly, (ii) a flexible cannula extending distally from the body, wherein the cannula is sized to be inserted through an incision in an eye of a patient, (iii) a needle slidably disposed in the cannula, (iv) a needle driver slidably disposed in the body, wherein the needle driver is operable to drive the needle longitudinally relative to the cannula, and (v) at least one magnet, wherein the at least one magnet is positioned to interact with the at least one ferrous element to thereby removably couple the injector assembly with the pad assembly.

Example 19

A method comprising: (a) positioning a pad on a patient's forehead, wherein the pad includes at least one ferrous element; (b) positioning an injector assembly on the pad, wherein the injector assembly includes at least one magnet, wherein the at least one magnet removably secures the injector assembly on the pad; (c) inserting a flexible cannula of the injector assembly into a sclerotomy formed through the eye of the patient; (d) advancing a needle distally through the flexible cannula; and (e) administering a therapeutic agent through the needle into the eye of the patient.

Example 20

The method of Example 19, wherein the act of advancing the needle distally comprises rotating a knob of the injector assembly, wherein the act of administering the therapeutic agent comprises actuating a switch of the injector assembly

VIII. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an injector assembly, wherein the injector assembly comprises:
      (i) a body,
      (ii) a flexible cannula extending distally from the body, wherein the flexible cannula is sized to be inserted through an incision in an eye of a patient, and
      (iii) a needle slidably disposed in the flexible cannula;
   (b) an injector driver, wherein the injector driver is operable to drive the needle longitudinally relative to the flexible cannula;
   (c) a fluid source assembly in fluid communication with the needle; and
   (d) a magnetic pad assembly, wherein the magnetic pad assembly is sized and configured to be placed on a forehead of the patient, and the magnetic pad assembly includes an adhesive;
   wherein the body of the injector assembly is configured to be removably secured to the magnetic pad assembly;
   wherein the injector assembly further comprises a magnet, wherein the magnet is configured to removably secure the body to the magnetic pad assembly via magnetic attraction, where the magnet is held in a stationary position relative to the body;
   wherein the injector driver is operable to drive the needle longitudinally relative to the magnet.

2. The apparatus of claim 1, wherein the injector driver is integrated into the body.

3. The apparatus of claim 1, wherein the injector driver is remotely coupled with the injector assembly via a flexible drive cable.

4. The apparatus of claim 1, wherein the magnetic pad assembly comprises at least one ferrous element.

5. The apparatus of claim 1, wherein the injector assembly further includes a needle actuator positioned in the body, wherein the needle is fixedly secured to the needle actuator, wherein the needle actuator is configured to translate relative to the body to thereby drive the needle longitudinally relative to the flexible cannula.

6. The apparatus of claim 5, wherein the needle actuator further includes at least two fluid inputs in fluid communication with the needle, such that the needle actuator is configured to form a manifold.

7. The apparatus of claim 1, wherein the injector driver comprises a rotary knob, wherein the rotary knob is rotatable to drive the needle longitudinally relative to the flexible cannula.

8. The apparatus of claim 7, wherein the rotary knob includes a spiral cam feature, wherein the spiral cam feature is configured to cooperate with another needle drive element to thereby drive the needle longitudinally in response to rotary movement of the rotary knob.

9. The apparatus of claim 7, wherein the injector driver further comprises a translatable member having a cam follower coupled with the spiral cam feature, wherein the cam follower and the spiral cam feature are configured to cooperate with each other to thereby convert rotary movement of the rotary knob into longitudinal movement of the needle.

10. The apparatus of claim 1, wherein the injector driver further comprises a first user input feature, wherein the first user input feature is operable to provide delivery of a therapeutic agent via the needle.

11. The apparatus of claim 10, wherein the first user input feature comprises a pushbutton.

12. The apparatus of claim 1, wherein the injector driver further comprises a bleb fluid delivery input feature, wherein the bleb fluid delivery input feature is operable to provide delivery of a bleb fluid via the needle.

13. The apparatus of claim 12, wherein the bleb fluid delivery input feature comprises a sensor, wherein the sensor is configured to sense a position of the needle in relation to the body, wherein the sensor comprises a linear potentiometer.

14. The apparatus of claim 1, wherein the fluid source assembly comprises a syringe actuation cassette, wherein the syringe actuation cassette is configured to provide automatic actuation of a syringe to thereby expel contents of the syringe through the needle.

15. The apparatus of claim 1, wherein the fluid source assembly further includes a thawing module, wherein the thawing module is operable to thaw a volume of frozen therapeutic agent.

* * * * *